(12) United States Patent
Dar et al.

(10) Patent No.: US 10,548,897 B2
(45) Date of Patent: Feb. 4, 2020

(54) KSR ANTAGONISTS

(71) Applicant: Icahn School of Medicine at Mount Sinai, New York, NY (US)

(72) Inventors: Arvin Dar, New York, NY (US); Neil Dhawan, New York, NY (US); Alex P. Scopton, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/566,565

(22) PCT Filed: Apr. 15, 2016

(86) PCT No.: PCT/US2016/027899
§ 371 (c)(1),
(2) Date: Oct. 13, 2017

(87) PCT Pub. No.: WO2016/168704
PCT Pub. Date: Oct. 20, 2016

(65) Prior Publication Data
US 2018/0256577 A1 Sep. 13, 2018

Related U.S. Application Data

(60) Provisional application No. 62/148,591, filed on Apr. 16, 2015.

(51) Int. Cl.
| | | |
|---|---|---|
| *A61K 31/517* | (2006.01) | |
| *A61P 35/00* | (2006.01) | |
| *C07D 239/94* | (2006.01) | |
| *C07D 239/72* | (2006.01) | |
| *C07D 239/93* | (2006.01) | |
| *C07D 239/88* | (2006.01) | |
| *C07D 401/12* | (2006.01) | |
| *C07D 403/12* | (2006.01) | |
| *C07D 405/12* | (2006.01) | |
| *C07D 409/12* | (2006.01) | |
| *A61K 31/519* | (2006.01) | |

(52) U.S. Cl.
CPC .......... *A61K 31/517* (2013.01); *A61K 31/519* (2013.01); *A61P 35/00* (2018.01)

(58) Field of Classification Search
CPC ..... A61K 31/517; A61P 35/00; C07D 239/94; C07D 239/72; C07D 239/93; C07D 239/88; C07D 401/12; C07D 403/12; C07D 405/12; C07D 409/12
See application file for complete search history.

(56) References Cited

U.S. PATENT DOCUMENTS

| | | |
|---|---|---|
| 7,618,975 B2 | 1/2009 | Cai et al. |
| 7,691,853 B2 | 4/2010 | Bebbington et al. |
| 7,709,479 B1 * | 5/2010 | Mortlock ............ A61K 31/517 |
| | | 514/235.8 |

FOREIGN PATENT DOCUMENTS

| | | |
|---|---|---|
| EP | 1 447 405 | 8/2004 |
| EP | 1 548 008 | 6/2005 |
| WO | WO 95/15758 | 6/1995 |
| WO | WO 96/09294 | 3/1996 |
| WO | WO 96/15118 | 5/1996 |
| WO | WO 01/21594 | 3/2001 |
| WO | WO 2014/017659 | 1/2014 |
| WO | WO 2015/165279 | 11/2015 |

OTHER PUBLICATIONS

Neilsen et al., KSR as a Therapeutic Target for Ras-Dependent Cancers, Expert Opinion Therapuetic Targets, vol. 21, No. 5, pp. 499-509, May 2017.*
Pubchem: SID 128743093 (Dec. 4, 2011).
Pubchem: SID 242086847 (Mar. 11, 2015).
Pubchem: SID 226737628 (Feb. 12, 2015).
International Search Report & Written Opinion issued by ISA/US for PCT/US2016/027899 (dated Sep. 21, 2016).
Adams et al, "PHENIX: a comprehensive Python-based system for macromolecular structure solution," Acta Crystallographica. Section D, Biological Crystallography, 2010, 66:213-221.
Blasco et al., "c-Raf, but Not B-Raf, Is Essential for Development of K-Ras Oncogene-Driven Non-Small Cell Lung Carcinoma," Cancer Cell, 2011, 19(5): 652-653.
Brennan et al., "A Raf-induced allosteric transition of KSR stimulates phosphorylation of MEK," Nature, 2011, 472(7343), 366-369.
Burley and Petsko, "Aromatic-aromatic interaction: a mechanism of protein structure stabilization," Science, 1985, 229:23-28.
Carver et al., "Reciprocal feedback regulation of PI3K and androgen receptor signaling in PTEN-deficient prostate cancer," Cancer Cell, 2011, 19(5): 575-586.
Chapman et al., "Combination of RAF and MEK inhibition for the treatment of BRAF-mutated melanoma: feedback is not encouraged," Cancer Cell, 2014, 26(5): 603-604.
Chou et al, "Quantitative analysis of dose-effect relationships: the combined effects of multiple drugs or enzyme inhibitors," Advances in Enzyme Regulation, 1984, 22:27-55.
Costanzo-Garvey et al., "KSR2 Is an Essential Regulator of AMP Kinase, Energy Expenditure, and Insulin Sensitivity," Cell Metab. 2009, 10(5): 366-378.
Dar, "A pickup in pseudokinase activity," Biochem Soc. Trans, 2013, 41(4): 987-994.
Downward, "KSR: A Novel Player in the RAS Pathway," Cell, 1995, 83(6): 831-834.
Emsley et al, "Features and development of Coot," Acta Crystallographica. Section D, Biological Crystallography, 2010, 66:486-501.
Extended European Search Report in Application No. 16780908.6, dated Aug. 16, 2018, 14 pages.
Farrar et al, "Activation of the Raf-1 kinase cascade by coumermycin-induced dimerization," Nature, 1996, 383:178-181.
Fernandez et al., "Kinase Suppressor of Ras-2 (KSR2) Regulates Tumor Cell Transformation via AMPK," Mol. Cell. Biol, 2012, 32(18): 3718-3731.
Glickman et al., "Converting Cancer Therapies into Cures: Lessons from Infectious Diseases," Cell, 2012, 148( 6): 1089-1098.

(Continued)

*Primary Examiner* — Brenda L Coleman
(74) *Attorney, Agent, or Firm* — Fish & Richardson P.C.

(57) ABSTRACT

This invention relates to antagonists of Kinase Suppressor of Ras (KSR). Pharmaceutical compositions comprising KSR inhibitors and methods of treating cancer are also provided.

7 Claims, 17 Drawing Sheets

(56) References Cited

OTHER PUBLICATIONS

Hu et al, "Allosteric Activation of Functionally Asymmetric RAF Kinase Dimers," Cell, 2013, 154:1036-1046.
Huang et al, "Raf-1 forms a stable complex with Mekl and activates Mekl by serine phosphorylation," PNAS, 1993, 90:10947-10951.
Kornfeld et al., "The ksr-1 Gene Encodes a Novel Protein Kinase Involved in Ras-Mediated Signaling in C. elegans," Cell, 1995, 83(6), 903-913.
Kubo et al., Synthesis and structure-activity relationship for new series of 4-Phenoxyquinoline derivatives as specific inhibitors of platelet-derived growth factor receptor tyrosine kinase, Bioorganic & Medicinal Chemistry, Nov. 2003, 11: 5117-5133.
Lavoie et al, "Inhibitors that stabilize a closed RAF kinase domain conformation induce dimerization," Nature Chemical Biology, 2013, 9:428-436.
Lozano et al., "Deficiency of Kinase Suppressor of Ras1 Prevents Oncogenic Ras Signaling in Mice," Cancer Res. 2003, 63(14): 4232-4238.
Lu et al., "Synthesis, characterization, screening and docking analysis of 4-anilinoquinazoline derivatives as tyrosine kinase inhibitors," European Journal of Medicinal Chemistry, Jul. 2012, 61: 84-94.
Michaud et al, "KSR stimulates Raf-1 activity in a kinase-independent manner," PNAS, 1997, 94:12792-12796.
Poulikakos et al, "RAF inhibitor resistance is mediated by dimerization of aberrantly spliced BRAF(V600E)," Nature, 2011, 480:387-390.
Pylayeva-Gupta et al., "RAS oncogenes: weaving a tumorigenic web," Nat. Rev. Cancer, 2011, 11(11):761-774.
Rajakulendran et al, "A dimerization-dependent mechanism drives RAF catalytic activation," Nature, 2009, 461:542-545.
Ritt et al., "KSR Regulation of the Raf☐MEK☐ERK Cascade," Methods Enzymol. 2006, 407: 224-237.
Roy et al, "KSR is a scaffold required for activation of the ERK/MAPK module," Genes & Development, 2002, 16:427-438.
Solomon and Lee, "Quinoline as a Privileged Scaffold in Cancer Drug Discovery," Current Medicinal Chemistry, Apr. 2011, 18: 1488-1508.
Stewart et al, "Kinase Suppressor of Ras Forms a Multiprotein Signaling Complex and Modulates MEK Localization," Molecular and Cellular Biology, 1999, 19:5523-5534.
Sundaram and Han, "The C. elegans ksr-1 gene encodes a novel Raf-related kinase involved in Ras-mediated signal transduction," Cell, 1995, 83(6): 889-901.
Therrien et al., "KSR, a novel protein kinase required for RAS signal transduction," Cell, 1995, 83(6): 879-888.
Tsai et al, "Discovery of a selective inhibitor of oncogenic B-Raf kinase with potent antimelanoma activity," PNAS, 2008, 105:3041-3046.
Vora et al., "CDK 4/6 inhibitors sensitize PIK3CA mutant breast cancer to PI3K inhibitors," Cancer Cell, 2014, 26(1): 136-149.
Zhao et al, "A New Bliss Independence Model to Analyze Drug Combination Data," Journal of Biomolecular Screening, 2014, 19:817-821.
'cen.wilcipedia.org' [online]. "MEK inhibitor," last edited on Feb. 22, 2019. Retrieved from the Internet: URL https://en.wikipedia.org/w/index.php?title=MEK_inhibitor&oldid=884547502. 3 pages.
McDermott and Qin, "Allosteric MEK1/2 Inhibitors for the Treatment of Cancer: an Overview," J Drug Res Dev, 2015, 1(1): http://dx.doi.org/10.16966/2470-1009.101, 9 pages.
Zhao and Adjei, "The clinical development of MEK inhibitors," Nat Rev Clin Oncol, 2014, 11: 385-400.

* cited by examiner

KSR ANTAGONISTS

CROSS REFERENCE TO RELATED APPLICATIONS

This application claims the benefit of U.S. Provisional Application Ser. No. 62/148,591, filed Apr. 16, 2015, the disclosure of which is incorporated herein by reference in its entirety.

FEDERALLY SPONSORED RESEARCH OR DEVELOPMENT

This invention was made with Government support under Grant No. 1 DP2 CA186570-01 awarded by the National Institutes of Health. The Government has certain rights in the invention.

TECHNICAL FIELD

This invention relates to antagonists of Kinase Suppressor of Ras (KSR) and more particularly to KSR inhibitors that are useful for the treatment of cancer.

BACKGROUND

In Ras-mutant cancers, unlike RAF-mutant cancers, it has thus far not been possible to inhibit the MAPK pathway sufficiently using therapeutically safe doses of RAF and MEK inhibitors partly due to the limited therapeutic window offered by these drug targets. One in four of all human cancers contain mutant forms of Ras and Ras is the one of the most frequently mutated oncogenes (see e.g., Pylayeva-Gupta, et al., *Nat. Rev. Cancer,* 2011, 11(11), 761-774). In particular, K-Ras and N-Ras substitutions are frequently observed in pancreatic (95% K-Ras), colon (47% K-Ras), lung (35% K-Ras) and melanoma (28% N-Ras).

SUMMARY

The present application provides, inter alia, a compound of Formula I:

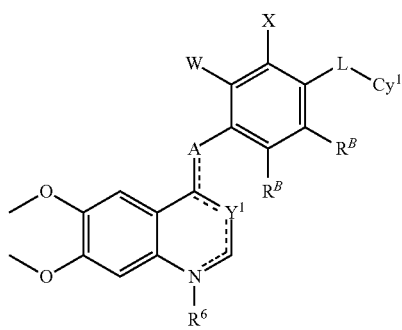

or a pharmaceutically acceptable salt thereof, wherein:
- - - - - indicates a single or double bond;

$Y^1$ is N or CH;

A is selected from the group consisting of N, NH, N($C_{1-4}$ alkyl), S, O, C(=O), and $C_{1-3}$ alkylene, wherein the $C_{1-3}$ alkylene is optionally substituted by a substituent selected from the group consisting of OH, $NH_2$, NH($C_{1-4}$ alkyl), and NH($C_{2-4}$ alkenyl);

L is selected from the group consisting of O, NH, S, C(=O), and $C_{1-3}$ alkylene, wherein the $C_{1-3}$ alkylene is optionally substituted by a substituent selected from the group consisting of OH, $NH_2$, NH($C_{1-4}$ alkyl), and NH($C_{2-4}$ alkenyl);

W and X are each independently selected from the group consisting of H, halo, and $C_{1-4}$ alkyl;

each $R^B$ is H; or alternatively, two $R^B$ groups come together, in combination with the carbon atoms to which they are attached, to form a $C_{3-6}$ carbocyclic group or a 3-6 membered heterocyclic group;

$Cy^1$ is selected from the group consisting of:

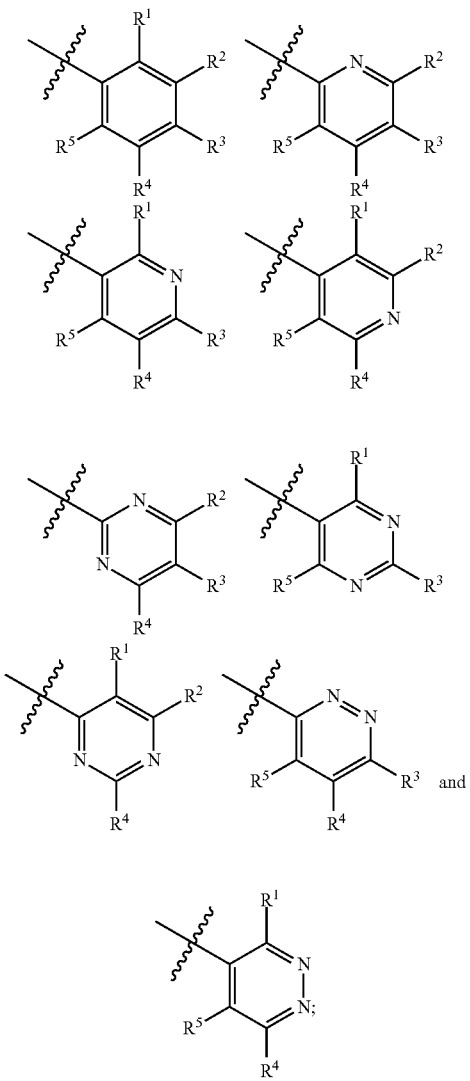

$R^1$ and $R^5$ are each independently selected from the group consisting of H, halo, OH, $C_{1-4}$ alkyl, and $C_{1-4}$ haloalkyl;

$R^3$ is selected from the group consisting of H and halo;

$R^2$ and $R^4$ are each independently selected from the group consisting of H and halo; and $R^6$ is absent or selected from the group consisting of H and $C_{1-4}$ alkyl;

with the proviso that when A is NH, $Y^1$ is N, L is O, and $Cy^1$ is

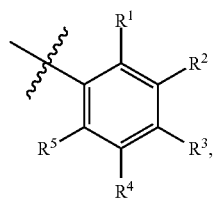

then at least one of W, X, $R^B$, $R^1$, $R^2$, $R^4$, $R^5$, and $R^6$ is not H.

In some embodiments, the compound is a compound of Formula Ia:

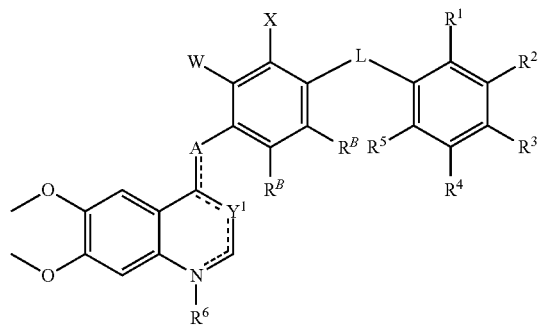

or a pharmaceutically acceptable salt thereof.

In some embodiments, $Y^1$ is N.

In some embodiments, A is selected from the group consisting of N, NH, N(CH$_3$), S, O, (C=O), CH(OH), CH$_2$, CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH(CH$_3$)$_2$), CH(NHC(CH$_3$)$_3$), and CH(NHCH$_2$CH=CH$_2$). In some embodiments, A is NH.

In some embodiments, L is selected from the group consisting of O, NH, S, C(=O), CH(OH), CH$_2$, CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH(CH$_3$)$_2$), CH(NHC(CH$_3$)$_3$), and CH(NHCH$_2$CH=CH$_2$). In some embodiments, L is O.

In some embodiments, W is selected from the group consisting of H, F, Cl, Br, and CH$_3$. In some embodiments, X is selected from the group consisting of H, F, Cl, Br, and CH$_3$. In some embodiments, X is F.

In some embodiments, each $R^B$ is H. In some embodiments, two $R^B$ groups come together, in combination with the carbon atoms to which they are attached, to form a $C_{3-6}$ carbocyclic group. In some embodiments, two $R^B$ groups come together, in combination with the carbon atoms to which they are attached, to form a $C_{3-6}$ carbocyclic group selected from:

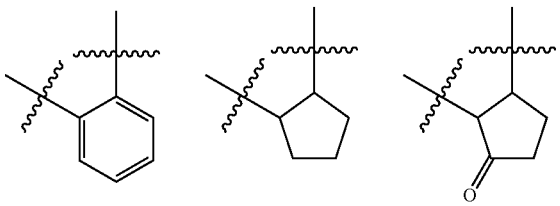

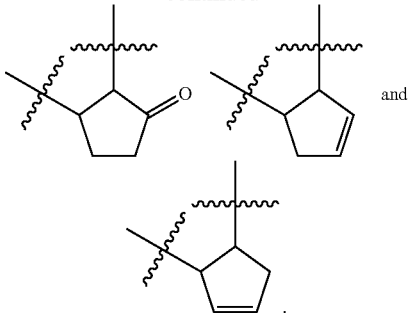

In some embodiments, two $R^B$ groups come together, in combination with the carbon atoms to which they are attached, to form a phenyl group. In some embodiments, two $R^B$ groups come together, in combination with the carbon atoms to which they are attached, to form a 3-6 membered heterocyclic group. In some embodiments, two $R^B$ groups come together, in combination with the carbon atoms to which they are attached, to form a 3-6 membered heterocyclic group selected from:

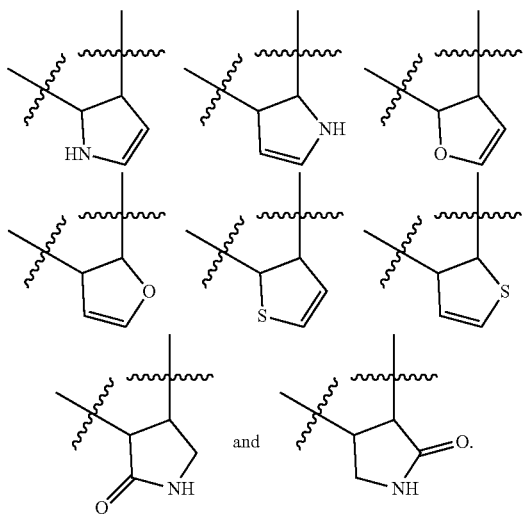

In some embodiments, $R^1$ is selected from the group consisting of H, F, OH, and CF$_3$.

In some embodiments, $R^2$ is selected from the group consisting of H, F and Cl.

In some embodiments, $R^3$ is H or Cl. In some embodiments, $R^3$ is H.

In some embodiments, $R^4$ is selected from the group consisting of H and F.

In some embodiments, $R^5$ is selected from the group consisting of H, F, OH, and CF$_3$.

In some embodiments, $R^6$ is absent. In some embodiments, $R^6$ is H or CH$_3$.

In some embodiments:
$Y^1$ is N;
A is selected from the group consisting of N, NH, N(CH$_3$), S, O, (C=O), CH(OH), CH(NH$_2$), and CH$_2$;
L is selected from the group consisting of O, NH, S, C(=O), CH$_2$, CH(OH), and CH(NH$_2$);
W and X are each independently selected from the group consisting of H, halo, and CH$_3$;

each $R^B$ is H; or alternatively, two $R^B$ groups come together, in combination with the carbon atoms to which they are attached, to form a $C_{3-6}$ carbocyclic group or a 3-6 membered heterocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo; and $R^6$ is absent or $CH_3$.

In some embodiments:

$Y^1$ is N;

A is selected from the group consisting of N, NH, $N(CH_3)$, S, O, and $CH_2$;

L is selected from the group consisting of O, NH, S, and $CH_2$;

W is selected from the group consisting of H, Cl, Br, and $CH_3$;

X is selected from the group consisting of H, F, Cl, Br, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^3$ is H;

$R^2$ and $R^4$ are each independently selected from the group consisting of H and halo; and $R^6$ is absent or $CH_3$.

In some embodiments:

$Y^1$ is N;

L is O;

A is NH;

W is selected from the group consisting of H, Cl, Br, and $CH_3$;

X is selected from the group consisting of H, F, Cl, Br, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^3$ is H; and $R^2$ and $R^4$ are each independently selected from the group consisting of H and halo; and $R^6$ is absent.

In some embodiments, the compound is a compound of Formula Ib:

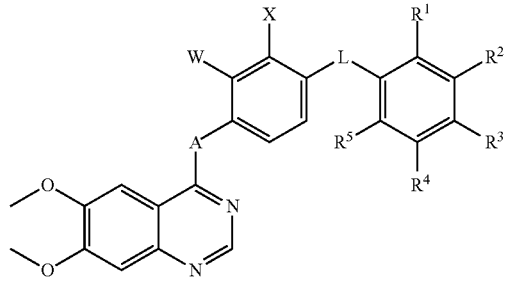

or a pharmaceutically acceptable salt thereof.

In some embodiments, the compound is a compound of Formula Ic:

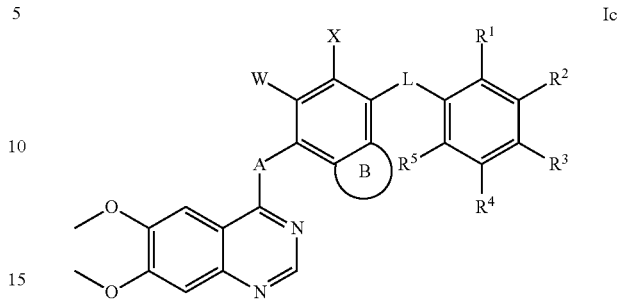

or a pharmaceutically acceptable salt thereof, wherein B is a $C_{3-6}$ carbocyclic group or a 3-6 membered heterocyclic group.

In some embodiments, the compound is a compound of Formula Id:

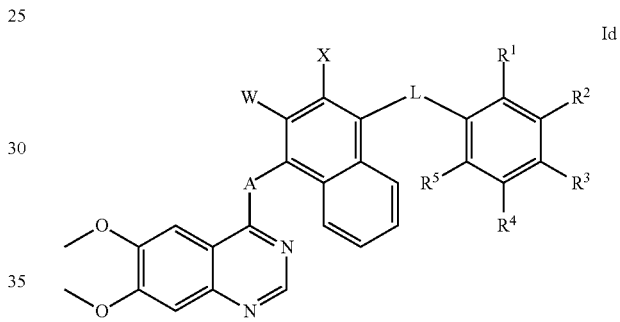

or a pharmaceutically acceptable salt thereof.

In some embodiments, the compound is selected from the group consisting of:

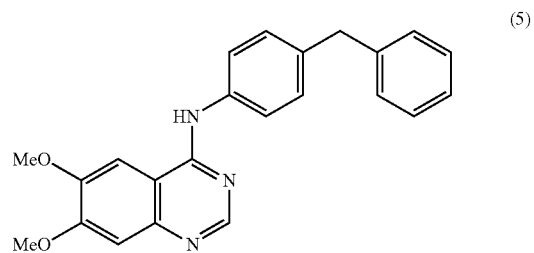

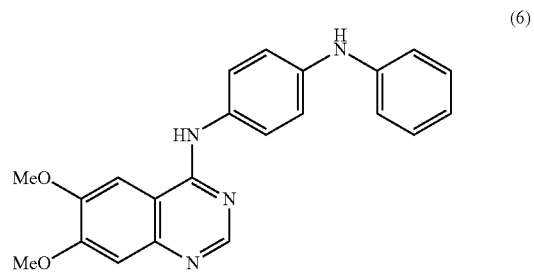

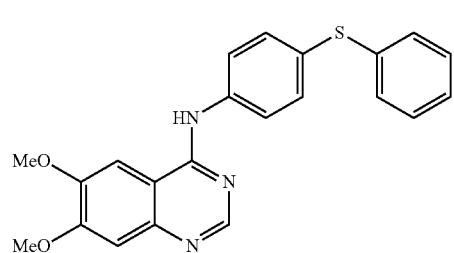 (9)
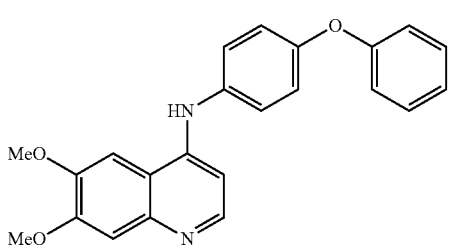 (11)
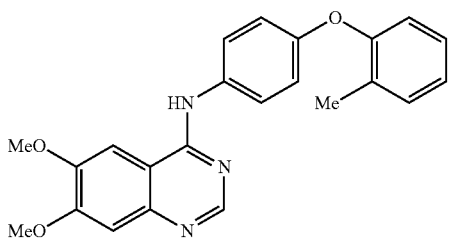 (12)
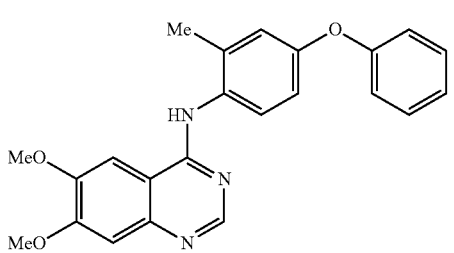 (21)
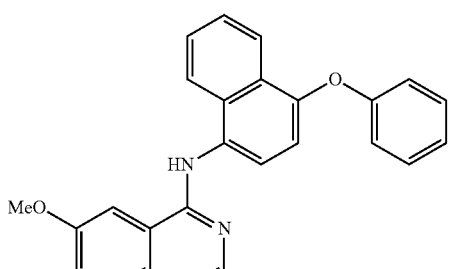 (23)
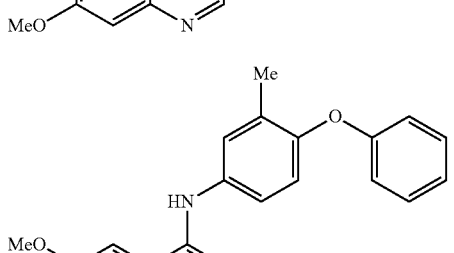 (24)
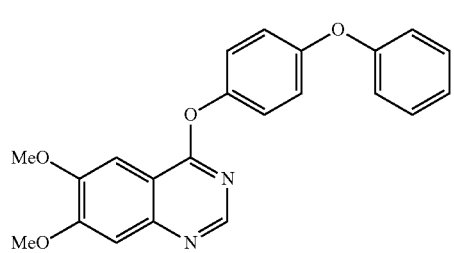 (28)
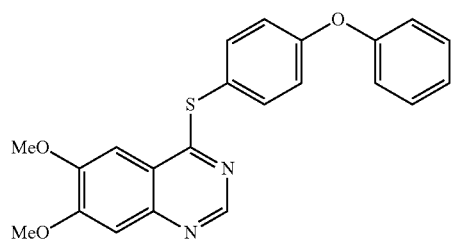 (31)
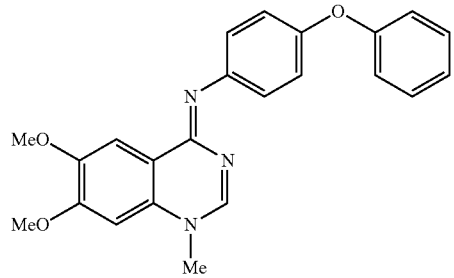 (32)
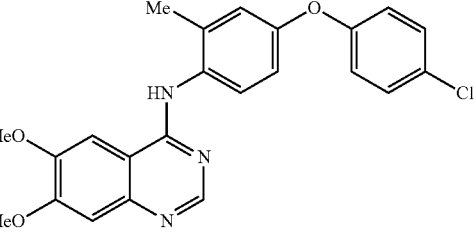 (37)
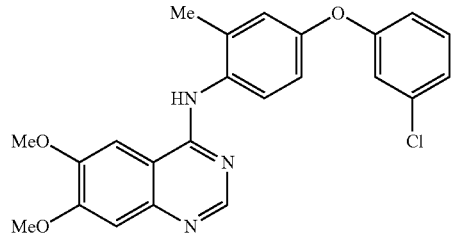 (38)
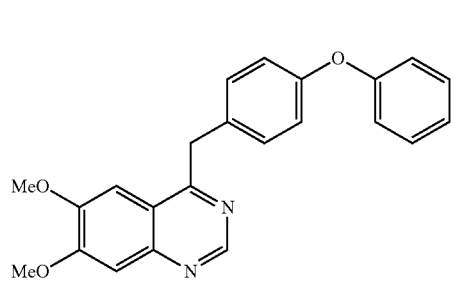 (43)

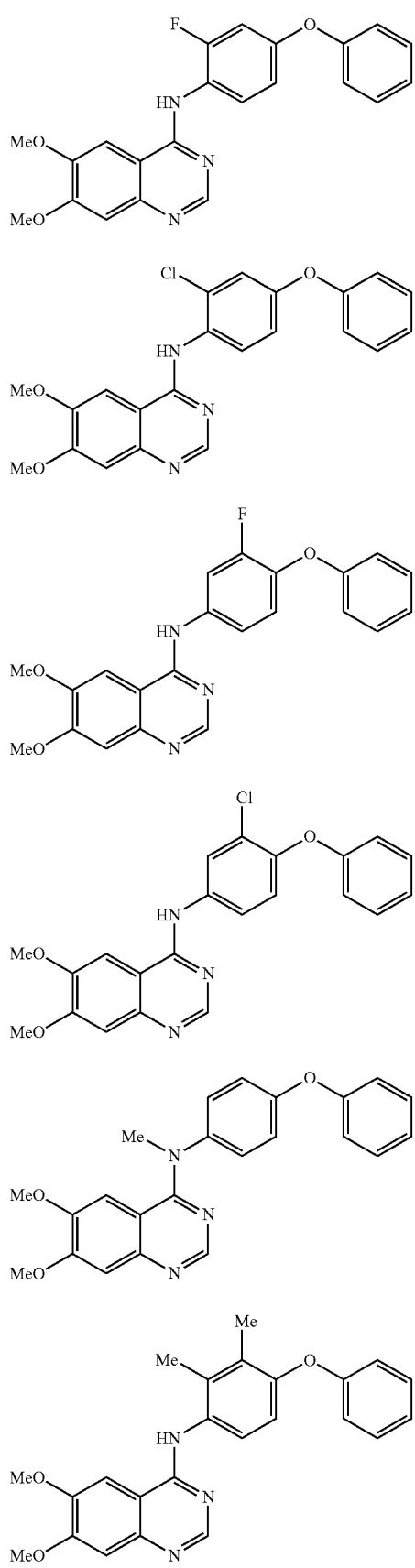
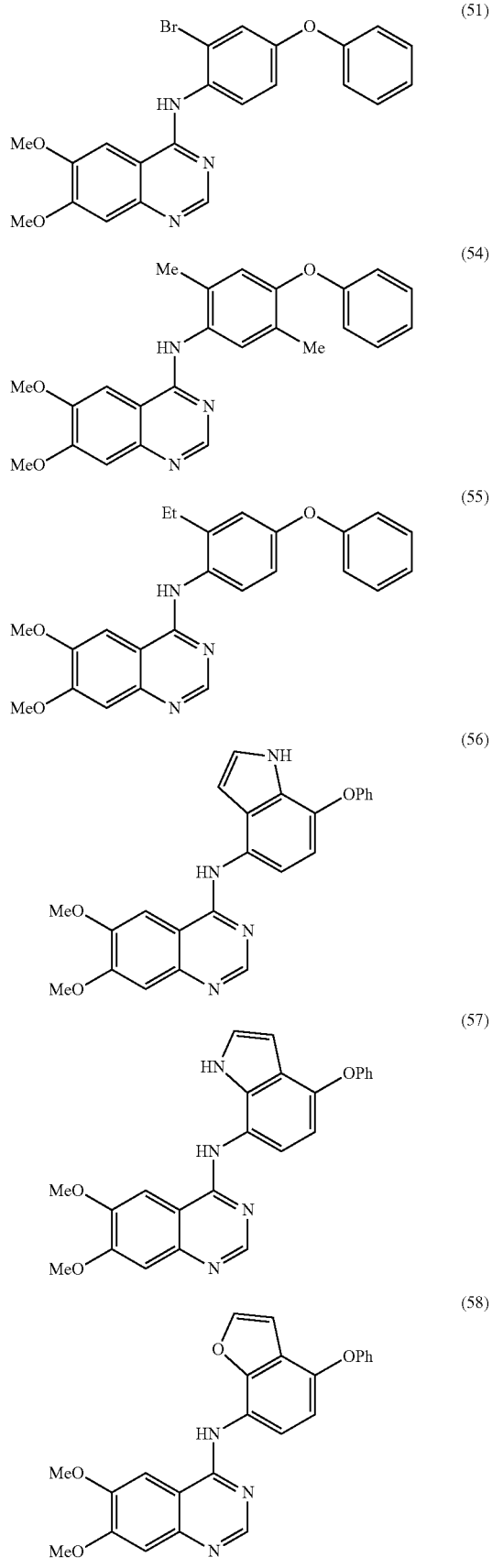

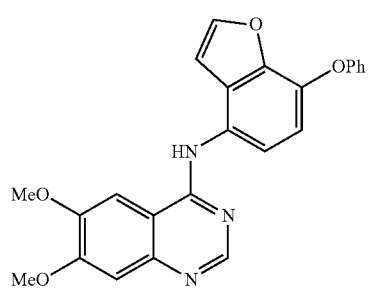
(59)
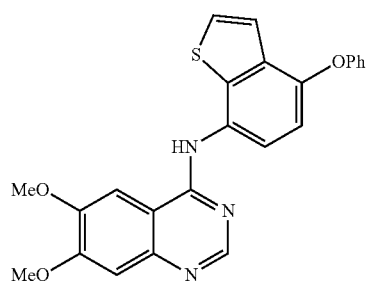
(60)
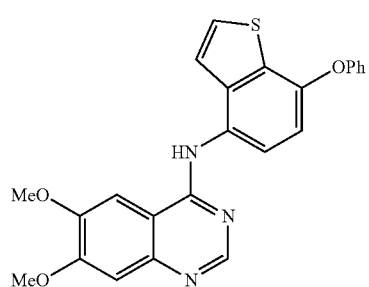
(61)
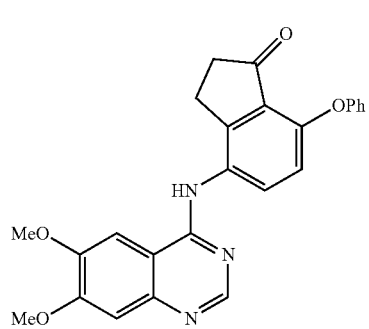
(62)
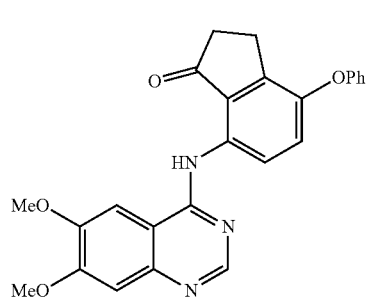
(63)
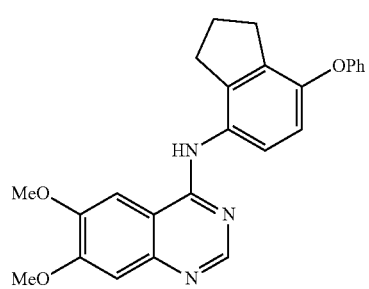
(64)
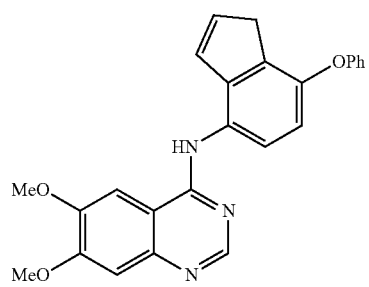
(65)
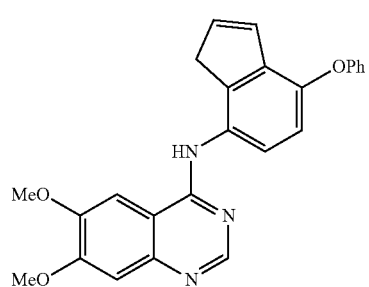
(66)
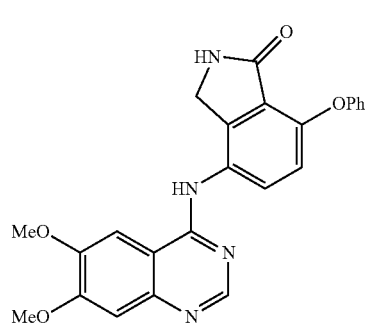
(67)
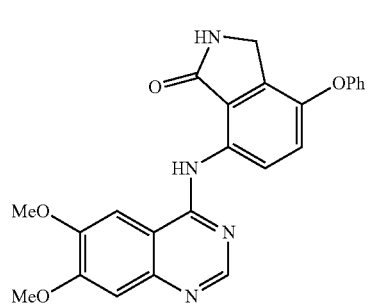
(68)

(69)
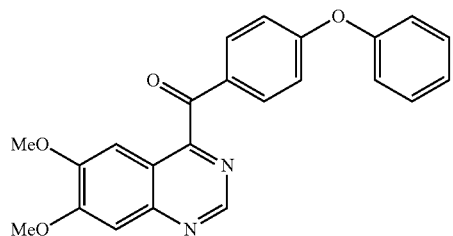
(70)
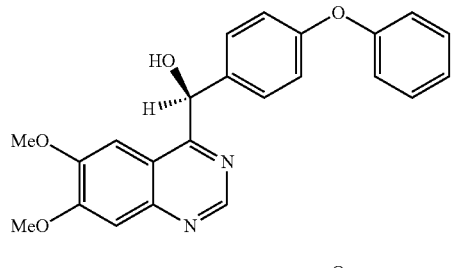
(71)
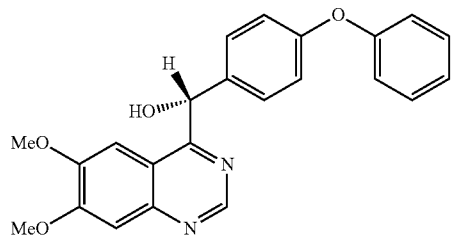
(72)
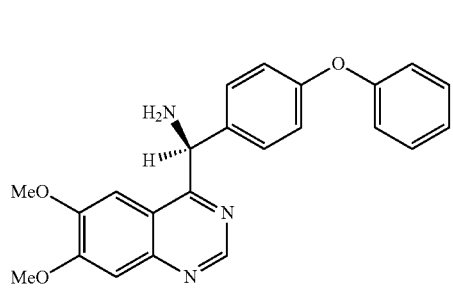
(73)
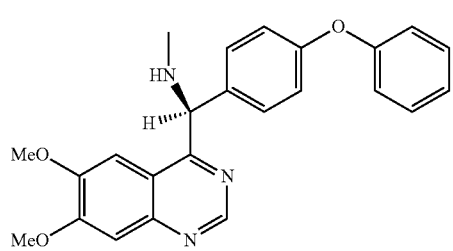
(74)
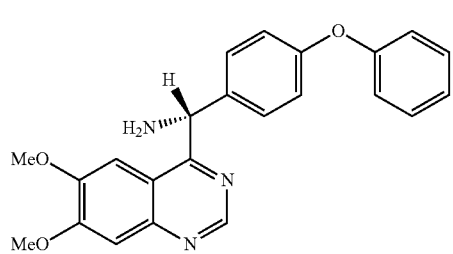
(75)
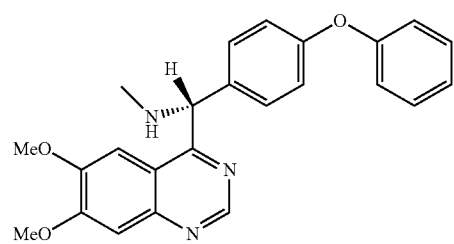
(76)
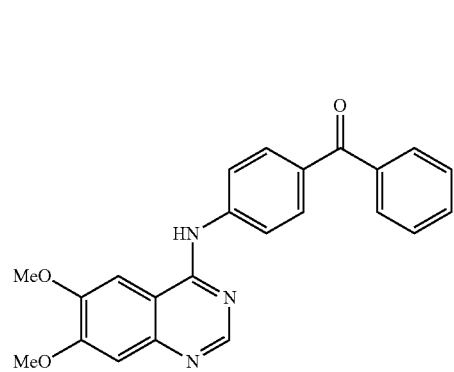
(77)
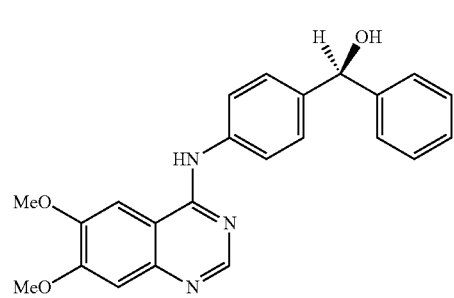
(78)
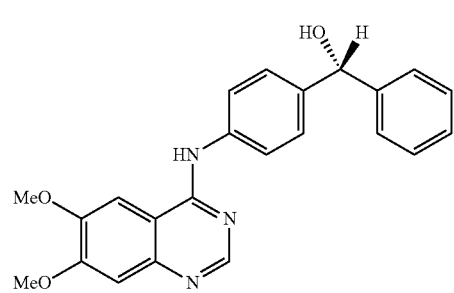
(79)
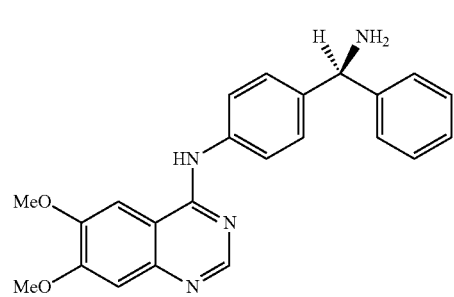

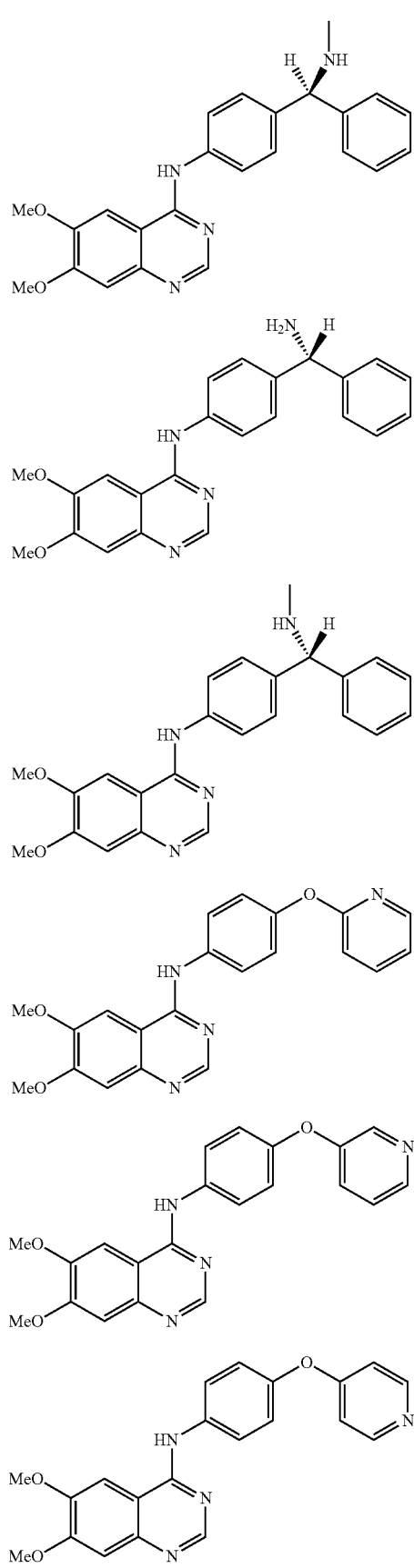
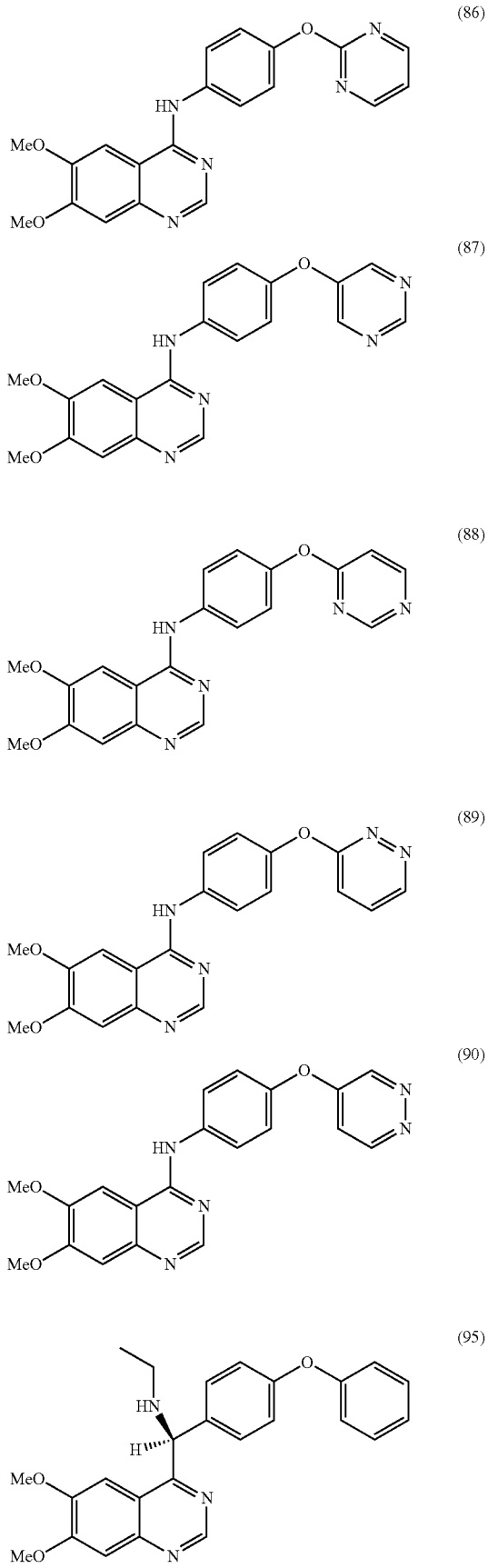

(96)
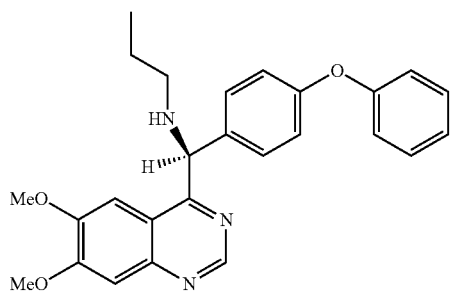
(97)
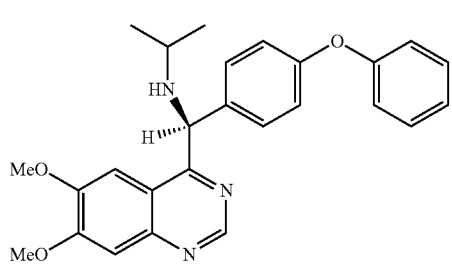
(98)
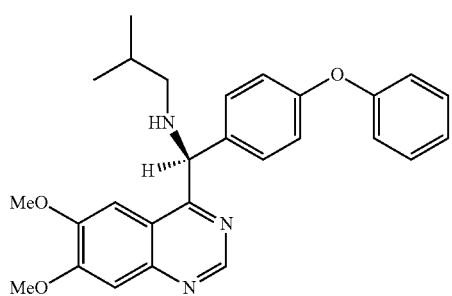
(99)
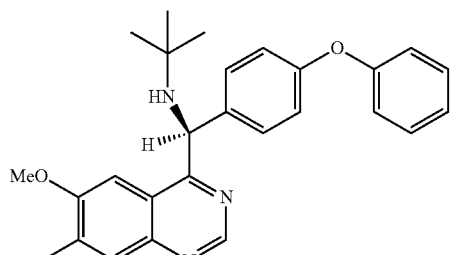
(100)
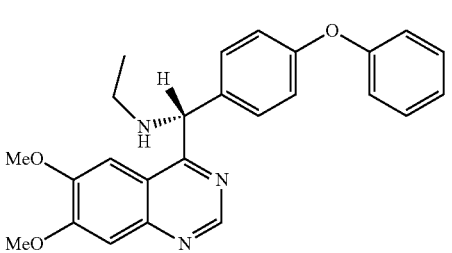
(101)
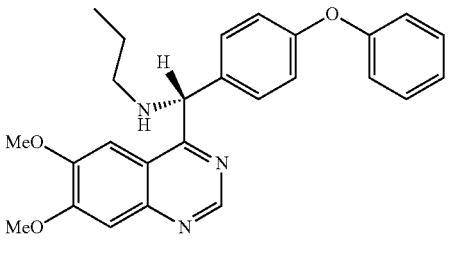
(102)
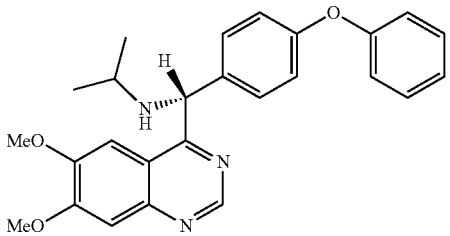
(103)
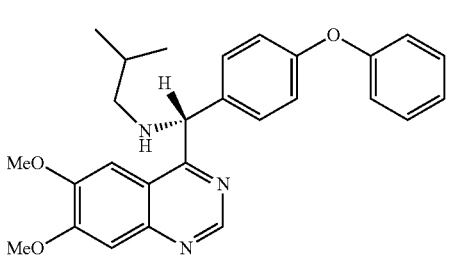
(104)
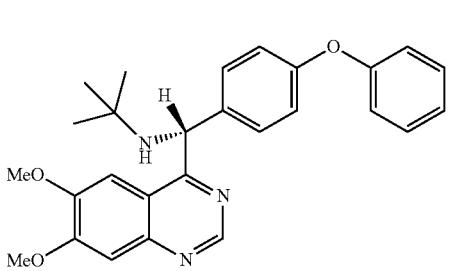
(105)
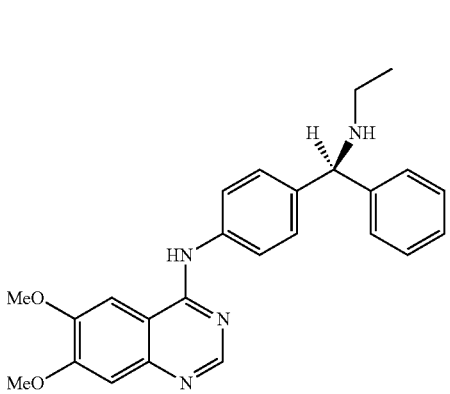
(106)
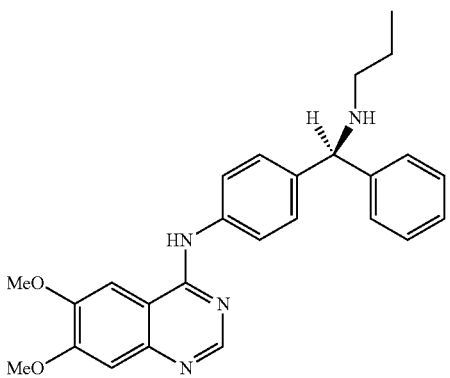

(107)
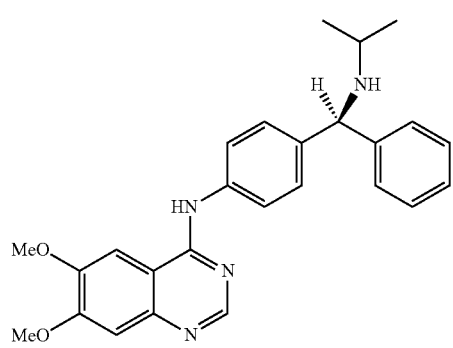
(108)
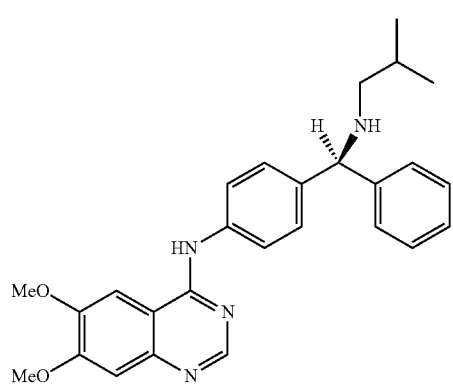
(109)
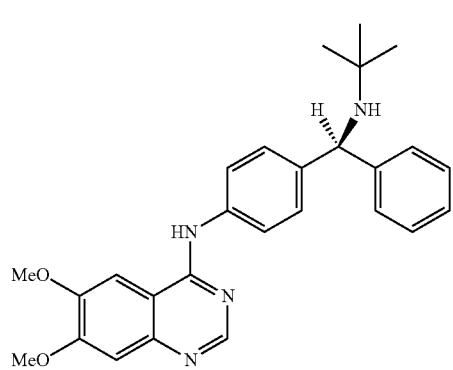
(110)
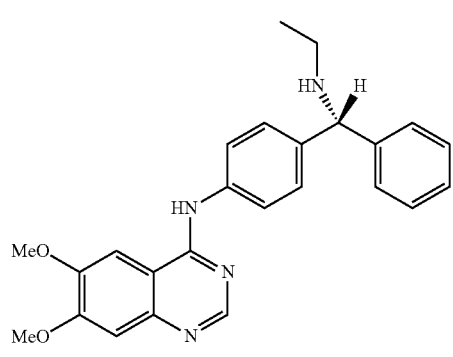
(111)
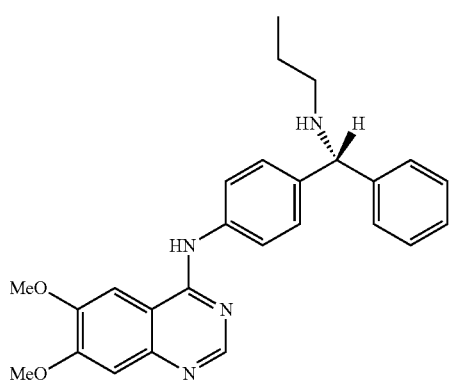
(112)
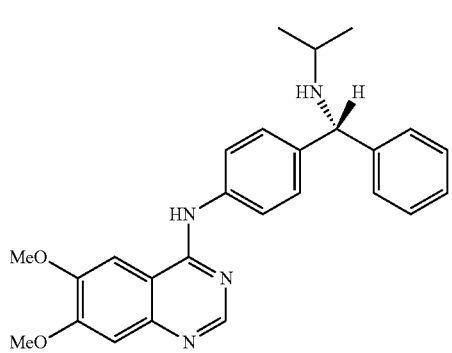
(113)
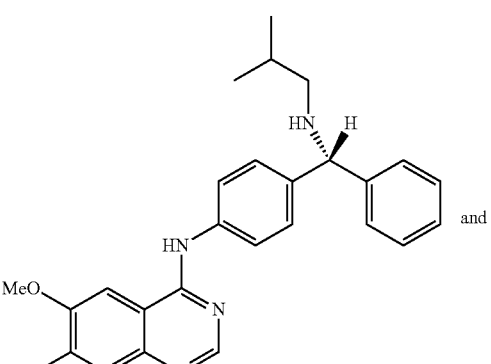
and
(114)
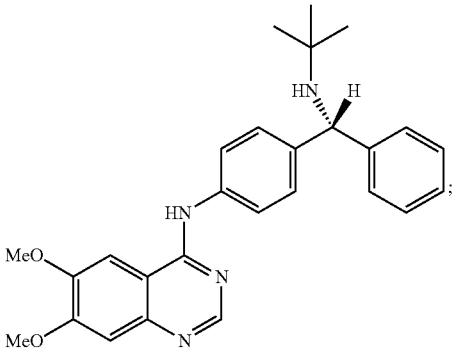
;
or a pharmaceutically acceptable salt thereof.
In some embodiments, the compound is 6,7-dimethoxy-N-(2-methyl-4-phenoxyphenyl)quinazolin-4-amine, or a pharmaceutically acceptable salt thereof. In some embodiments, the compound is 6,7-dimethoxy-N-(2-methyl-4-phenoxyphenyl)quinazolin-4-amine 2,2,2-trifluoroacetate. In some embodiments, the compound is 6,7-dimethoxy-N-(2-methyl-4-phenoxyphenyl)quinazolin-4-amine hydrochloride.

The present application further provides a compound of Formula II:

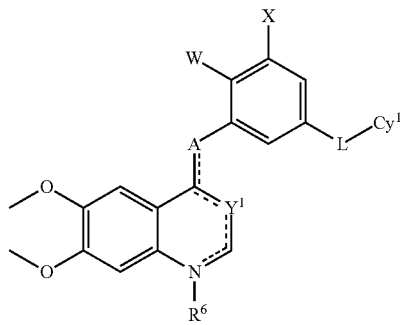

II or a pharmaceutically acceptable salt thereof, wherein:

----- indicates a single or double bond;

$Y^1$ is N or CH;

A is selected from the group consisting of N, NH, N(C$_{1-4}$ alkyl), S, O, C(=O), and C$_{1-3}$ alkylene, wherein the C$_{1-3}$ alkylene is optionally substituted by a substituent selected from the group consisting of OH, NH$_2$, NH(C$_{1-4}$ alkyl), and NH(C$_{2-4}$ alkenyl);

L is selected from the group consisting of O, NH, S, C(=O), and C$_{1-3}$ alkylene; wherein the C$_{1-3}$ alkylene is optionally substituted by a substituent selected from the group consisting of OH, NH$_2$, NH(C$_{1-4}$ alkyl), and NH(C$_{2-4}$ alkenyl);

W and X are each independently selected from the group consisting of H, halo, and C$_{1-4}$ alkyl;

Cy$^1$ is selected from the group consisting of:

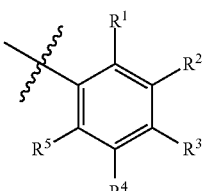
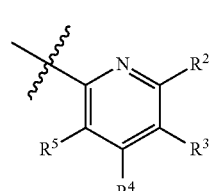
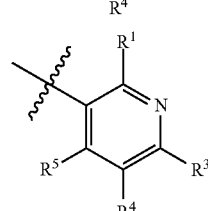
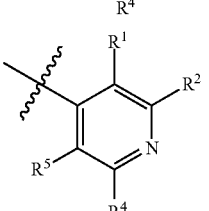
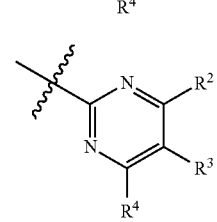
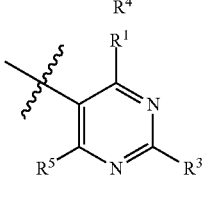

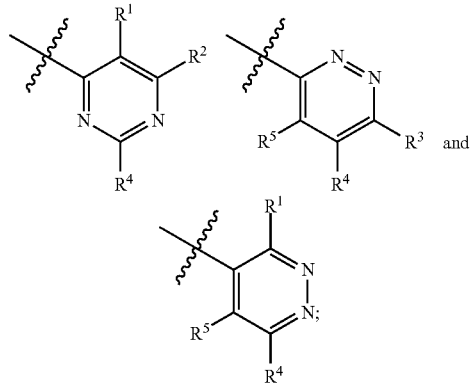

and $R^1$ and $R^5$ are each independently selected from the group consisting of H, halo, OH, C$_{1-4}$ alkyl, and C$_{1-4}$ haloalkyl;

$R^3$ is selected from the group consisting of H and halo; and $R^2$ and $R^4$ are each independently selected from the group consisting of H and halo; or alternatively, $R^4$ and $R^5$ come together, in combination with the carbon atoms to which they are attached, to form a C$_{3-6}$ carbocyclic group or a 3-6 membered heterocyclic group; and $R^6$ is absent or selected from the group consisting of H and C$_{1-4}$ alkyl.

In some embodiments, the compound is a compound of Formula IIa:

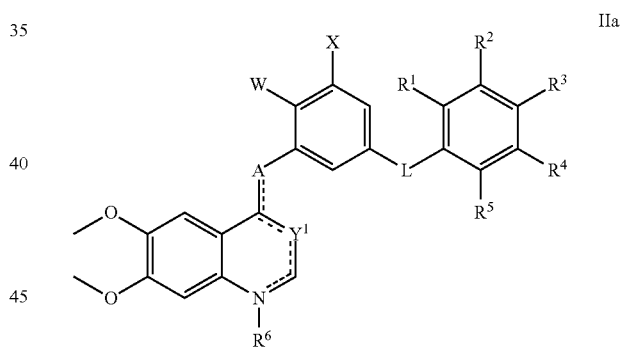

IIa or a pharmaceutically acceptable salt thereof.

In some embodiments, $Y^1$ is N.

In some embodiments, A is selected from the group consisting of N, NH, N(CH$_3$), S, O, (C=O), CH(OH), CH$_2$, CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH (CH$_3$)$_2$), CH(NHC(CH$_3$)$_3$), and CH(NHCH$_2$CH=CH$_2$). In some embodiments, A is NH.

In some embodiments, L is selected from the group consisting of O, NH, S, C(=O), CH(OH), CH$_2$, CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH(CH$_3$)$_2$), CH(NHC (CH$_3$)$_3$), and CH(NHCH$_2$CH=CH$_2$). In some embodiments, L is O.

In some embodiments, W is selected from the group consisting of H, Cl, Br, and CH$_3$.

In some embodiments, X is selected from the group consisting of H, F, Cl, Br, and CH$_3$. In some embodiments, X is F.

In some embodiments, $R^1$ is selected from the group consisting of H, F, OH, and $CF_3$.

In some embodiments, $R^2$ is selected from the group consisting of H and F.

In some embodiments, $R^3$ is selected from the group consisting of H and Cl. In some embodiments, $R^3$ is H.

In some embodiments, $R^4$ is selected from the group consisting of H and F.

In some embodiments, $R^5$ is selected from the group consisting of H, F, OH, and $CF_3$.

In some embodiments, $R^4$ and $R^5$ are each H. In some embodiments, $R^4$ and $R^5$ come together, in combination with the carbon atoms to which they are attached, to form a $C_{3-6}$ carbocyclic group. In some embodiments, $R^4$ and $R^5$ come together, in combination with the carbon atoms to which they are attached, to form a $C_{3-6}$ carbocyclic group selected from:

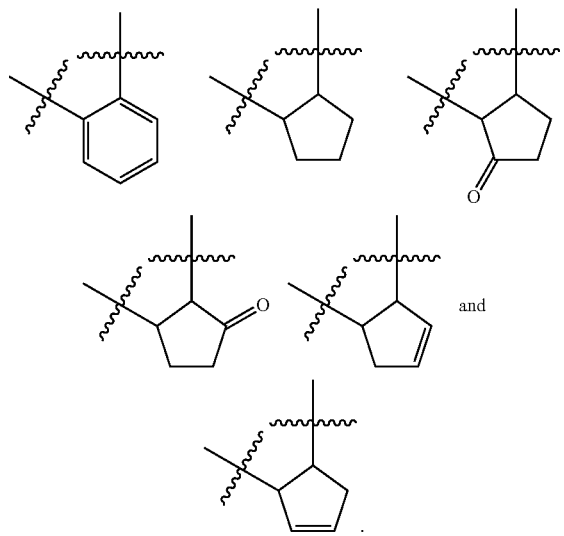

In some embodiments, $R^4$ and $R^5$ come together, in combination with the carbon atoms to which they are attached, to form a phenyl group. In some embodiments, $R^4$ and $R^5$ come together, in combination with the carbon atoms to which they are attached, to form 3-6 membered heterocyclic group. In some embodiments, $R^4$ and $R^5$ come together, in combination with the carbon atoms to which they are attached, to form 3-6 membered heterocyclic group selected from:

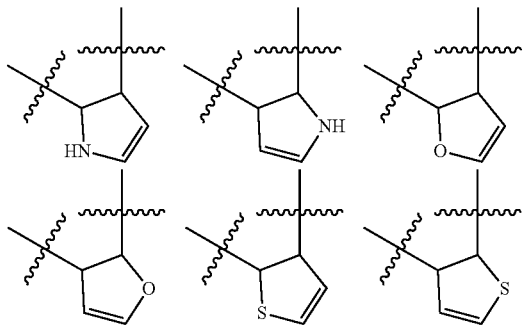

-continued

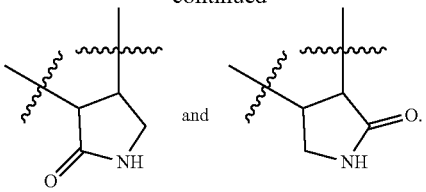

and

In some embodiments, $R^6$ is absent. In some embodiments, $R^6$ is selected from the group consisting of H and $CH_3$.

In some embodiments:
$Y^1$ is N;
A is selected from the group consisting of N, NH, $N(CH_3)$, S, O, and $CH_2$;
L is selected from the group consisting of O, NH, S, and $CH_2$;
W and X are each independently selected from the group consisting of H, halo, and $CH_3$;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl;
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group or a 3-6 membered heterocyclic group; and
$R^6$ is absent or $CH_3$.

In some embodiments:
$Y^1$ is N;
A is selected from the group consisting of N, NH, $N(CH_3)$, S, O, and $CH_2$;
L is selected from the group consisting of O, NH, S, and $CH_2$;
W is selected from the group consisting of H, Cl, Br, and $CH_3$;
X is selected from the group consisting of H, F, Cl, Br, and $CH_3$;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl;
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group or a 3-6 membered heterocyclic group; and
$R^6$ is absent or $CH_3$.

In some embodiments:
$Y^1$ is N;
L is O;
A is NH;
W is selected from the group consisting of H, Cl, Br, and $CH_3$;
X is selected from the group consisting of H, F, Cl, Br, and $CH_3$;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl;
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group or a 3-6 membered heterocyclic group; and
$R^6$ is absent.

In some embodiments:

$Y^1$ is N;

L is O;

A is NH;

W is selected from the group consisting of H, Cl, Br, and $CH_3$;

X is selected from the group consisting of H, F, Cl, Br, and $CH_3$;

$R^1$ is selected from the group consisting of H, halo, OH, $C_{1-4}$ alkyl, and $C_{1-4}$ haloalkyl;

$R^2$ is selected from the group consisting of H and halo;

$R^3$ is selected from the group consisting of H and Cl;

$R^4$ and $R^5$ are each H; and $R^6$ is absent.

In some embodiments, the compound is a compound of Formula IIb:

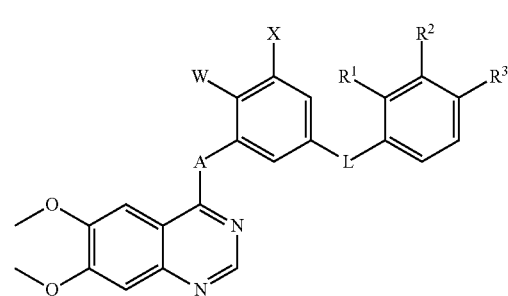

IIb or a pharmaceutically acceptable salt thereof.

In some embodiments, the compound is a compound of Formula IIc:

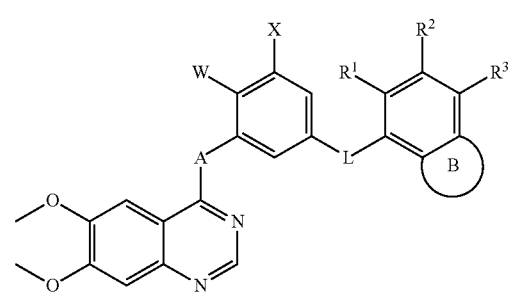

IIc or a pharmaceutically acceptable salt thereof, wherein B is a $C_{3-6}$ carbocyclic group or a 3-6 membered heterocyclic group.

In some embodiments, the compound is a compound of Formula IId:

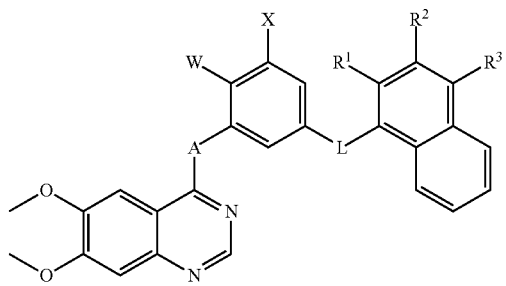

IId or a pharmaceutically acceptable salt thereof.

In some embodiments, the compound is selected from the group consisting of:

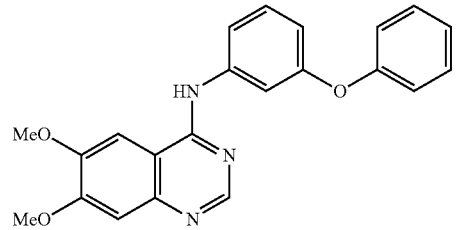

(4)

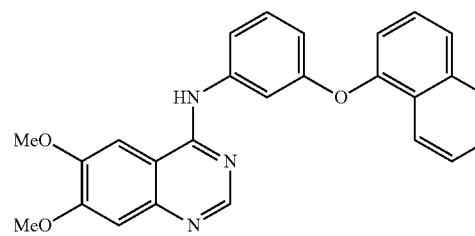

(13)

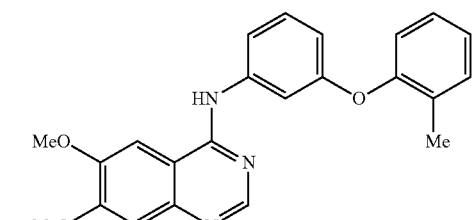

(14)

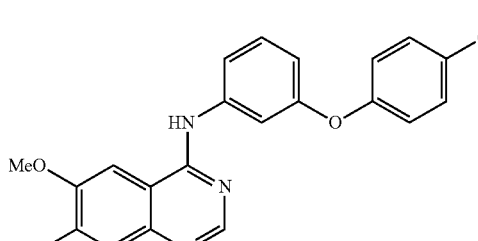

(15)

-continued
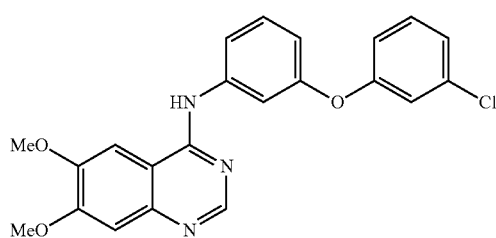
(16)
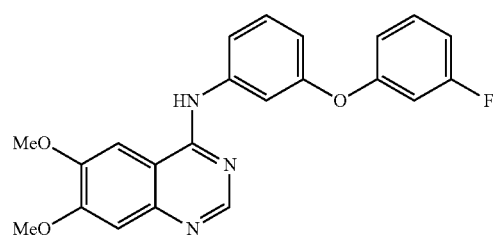
(17)
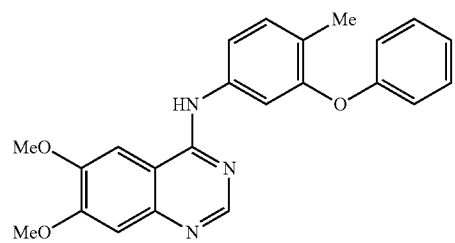
(34)
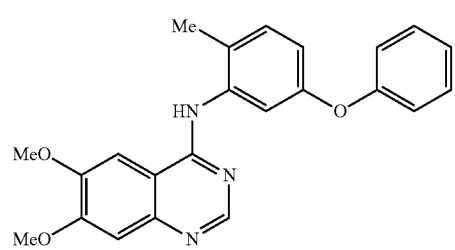
(35)
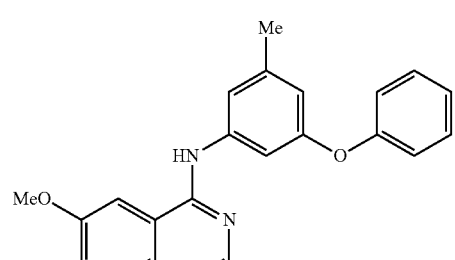
(36)
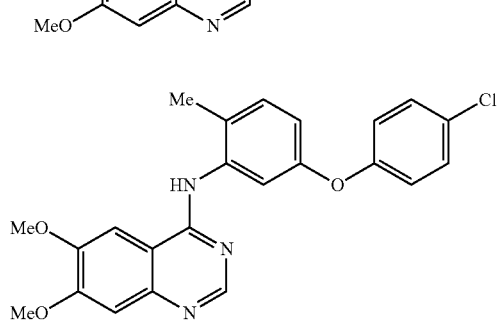
(39)
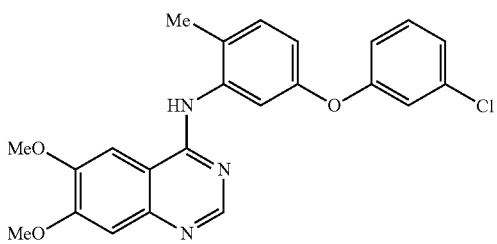
(40)
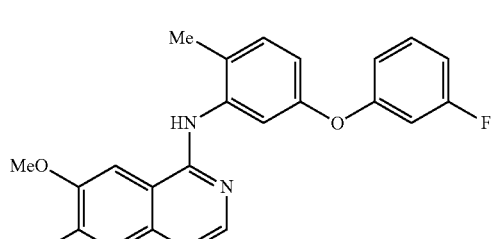
(41)
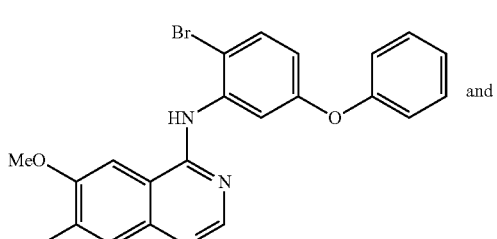
(42)
and
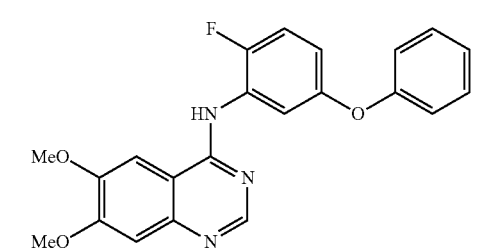
(48)
or a pharmaceutically acceptable salt thereof.
The present application further provides a compound of Formula III:
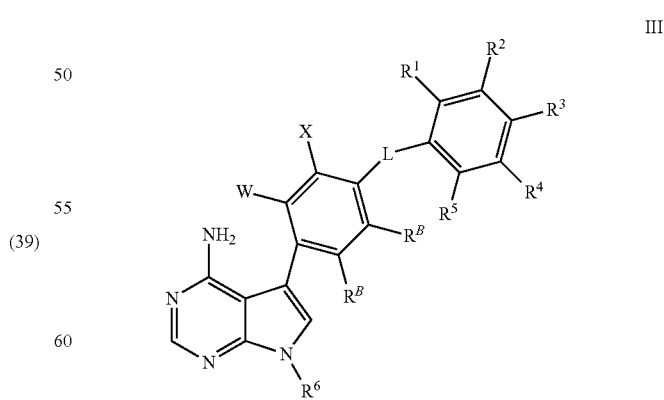
III
or a pharmaceutically acceptable salt thereof, wherein:
L is selected from the group consisting of O, NH, S, and $C_{1-3}$ alkylene;

W and X are each independently selected from the group consisting of H, halo, and $C_{1-4}$ alkyl;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and halo; and $R^6$ is selected from the group consisting of H, $C_{1-3}$ alkyl, $C_{3-6}$ cycloalkyl and $C_{3-6}$ heterocycloalkyl.

In some embodiments, L is selected from the group consisting of O, NH, S, and $CH_2$. In some embodiments, L is O.

In some embodiments, W is selected from the group consisting of H, Cl, Br, and $CH_3$.

In some embodiments, X is selected from the group consisting of H, F, Cl, Br, and $CH_3$. In some embodiments, X is F.

In some embodiments, each $R^B$ is H. In some embodiments, two $R^B$ groups come together, in combination with the carbon atoms to which they are attached, to form a $C_{3-6}$ carbocyclic group. In some embodiments, two $R^B$ groups come together, in combination with the carbon atoms to which they are attached, to form a phenyl group.

In some embodiments, $R^1$ is selected from the group consisting of H, F, OH, and $CF_3$.

In some embodiments, $R^2$ is selected from the group consisting of H and F.

In some embodiments, $R^3$ is selected from the group consisting of H and Cl. In some embodiments, $R^3$ is H.

In some embodiments, $R^4$ is selected from the group consisting of H and F.

In some embodiments, $R^5$ is selected from the group consisting of H, F, OH, and $CF_3$.

In some embodiments, $R^6$ is selected from the group consisting of H, $C_{1-3}$ alkyl, and $C_{5-6}$ cycloalkyl and 5-6 membered heterocycloalkyl. In some embodiments, $R^6$ is selected from the group consisting of H, $CH_3$, cyclopentyl, 3-piperidinyl, 4-piperidinyl, and 3-pyrrolidinyl.

In some embodiments:

L is selected from the group consisting of O, NH, S, and $CH_2$;

W and X are each independently selected from the group consisting of H, halo, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and Cl; and $R^6$ is selected from the group consisting of H, $C_{1-3}$ alkyl, $C_{3-6}$ cycloalkyl and 3-6 membered heterocycloalkyl.

In some embodiments:

L is selected from the group consisting of O, NH, S, and $CH_2$;

W is selected from the group consisting of H, Cl, Br, and $CH_3$;

X is selected from the group consisting of H, F, Cl, Br, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and Cl; and $R^6$ is selected from the group consisting of H, $C_{1-3}$ alkyl, $C_{5-6}$ cycloalkyl, and 5-6 membered heterocycloalkyl.

In some embodiments:

L is O;

W is selected from the group consisting of H, Cl, Br, and $CH_3$;

X is selected from the group consisting of H, F, Cl, Br, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and Cl; and $R^6$ is selected from the group consisting of H, $CH_3$, $C_{5-6}$ membered cycloalkyl, and 5-6 membered heterocycloalkyl.

In some embodiments, the compound is a compound of Formula IIIa:

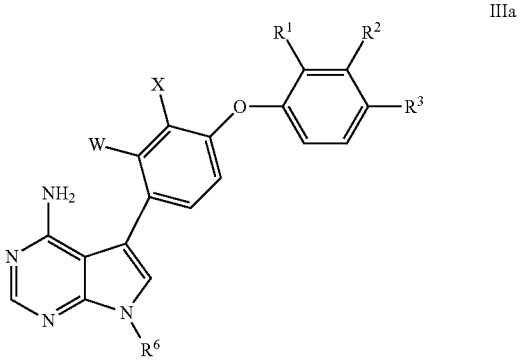

or a pharmaceutically acceptable salt thereof.

In some embodiments, the compound is a compound of Formula IIIb:

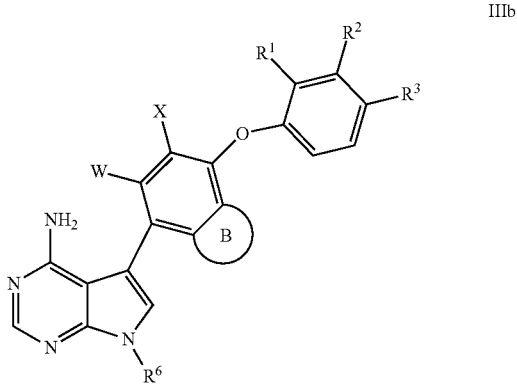

or a pharmaceutically acceptable salt thereof, wherein B is a $C_{3-6}$ carbocyclic group or a 3-6 membered heterocycloalkyl group.

In some embodiments, the compound is a compound of Formula IIIc:

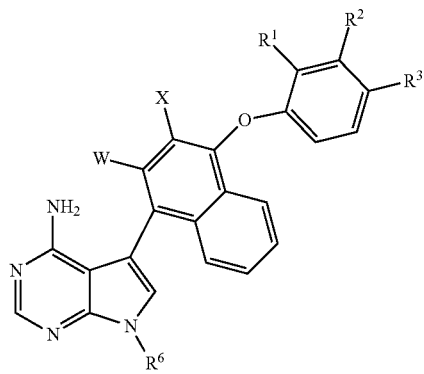

IIIc or a pharmaceutically acceptable salt thereof.

In some embodiments, the compound is selected from the group consisting of:

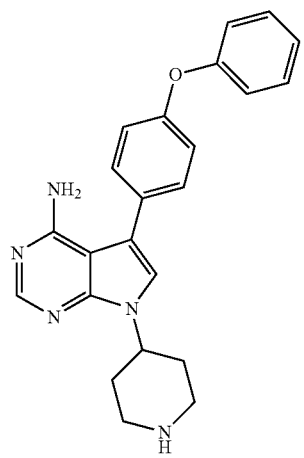

(91)

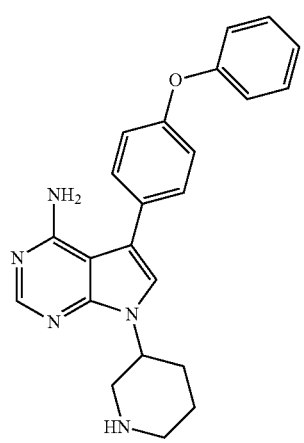

(92)

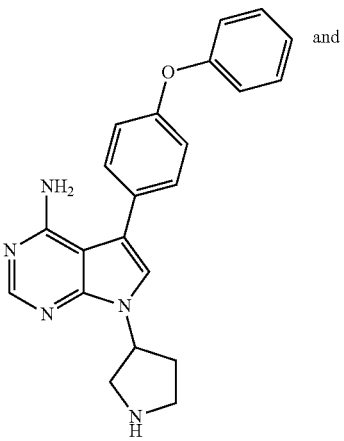

(93)

and

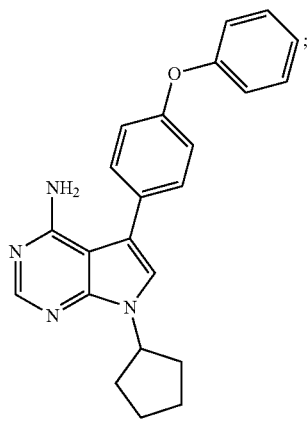

(94)

or a pharmaceutically acceptable salt thereof.

In some embodiments, the compound is 7-cyclopentyl-5-(4-phenoxyphenyl)-7H-pyrrolo[2,3-d]pyrimidin-4-amine, or a pharmaceutically acceptable salt thereof.

The present application further provides a pharmaceutical composition comprising a compound provided herein, or a pharmaceutically acceptable salt thereof, and at least one pharmaceutically acceptable carrier.

The present application further provides a method of treating cancer in a patient in need thereof, comprising administering to the patient a therapeutically effective amount of a compound provided herein.

The present application further provides a method of treating cancer in a patient in need thereof, comprising:
(i) determining if the cancer is associated with KSR; and
(ii) if the cancer is determined to be associated with KSR, administering to the patient a therapeutically effective amount of a compound provided herein, or a pharmaceutically acceptable salt thereof.

In some embodiments, the cancer is selected from the group consisting of breast cancer, prostate cancer, esophageal cancer, colon cancer, endometrial cancer, brain cancer, bladder cancer, skin cancer, cancer of the uterus, cancer of the ovary, lung cancer, pancreatic cancer, renal cancer, prostate cancer, gastric cancer, stomach cancer, and hematological cancer.

In some embodiments, the lung cancer is selected from the group consisting of non-small cell lung cancer, small cell lung cancer, and lung carcinoid tumor.

In some embodiments, the non-small cell lung cancer comprises an adenocarcinoma of the lung or squamous cell cancer of the lung.

In some embodiments, the hematological cancer is selected from the group consisting of leukemia, lymphoma, and multiple myeloma.

In some embodiments, the leukemia is selected from the group consisting of acute lymphoblastic leukemia (ALL), chronic lymphocytic leukemia (CLL), acute myelogenous leukemia (AML), chronic myeloid leukemia (CML), hairy cell leukemia, T-cell prolymphocytic leukemia, juvenile myelomonocytic leukemia, and follicular lymphoma.

In some embodiments, the lymphoma is Hodgkin's lymphoma or non-Hodgkin's lymphoma.

In some embodiments, the method further comprises administering an additional therapeutic agent. In some embodiments, the additional therapeutic agent is a chemotherapeutic agent. In some embodiments, the additional therapeutic agent is a KSR inhibitor or a MEK inhibitor. In some embodiments, the additional therapeutic agent is a MEK inhibitor. In some embodiments, the MEK inhibitor is selected from the group consisting of trametinib, selumetinib, binimetinib, refametinib, pimasertib, cobimetinib, AZD8330, RO4987655, RO5126766, WX-554, E6201, MSC1936369B, PD-325901, CI-1040, RDEA119, CH5126766, GDC-0623, G-573, TAK-733, TAK-133, CI-1 040/PD1 84352, AZD6244, PD318088, PD98059, PD334581, RDEA1 19, 6-methoxy-7-(3-morpholin-4-yl-propoxy)-4-(4-phenoxy-phenylamino)quinoline-3-carbonitrile, and 4-[3-Chloro-4-(1-methyl-1H-imidazol-2-ylsulfanyl)phenylamino]-6-methoxy-7-(3-morpholin-4-yl-propoxy)-quinoline-3-carbonitrile, and PD035901.

The present application further provides a method of inhibiting a KSR in a cell, comprising contacting the cell with an effective amount of a compound provided herein, or a pharmaceutically acceptable salt thereof.

The present application further provides a method of inhibiting a KSR and a MEK in a cell, comprising contacting the cell with an effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

In FIG. 10A, HEK293 cells were serum starved for 24 hours and simultaneously treated with two independent siRNAs against KSR1. siNTC was used as a scrambled control. After induction with 5% FBS, cells were harvested at 0, 30, 60, and 120 seconds. In FIG. 10B, HEK293 cells were similarly serum starved and pre-treated with Compound 21 for 2 h before induction. The cells were then induced with FBS as in FIG. 10A.

FIG. 13A shows a BLISS score analysis of HCT-116, A549, A375, and SK-MEL-239 cells treated with Compound 21, sarcatinib, or lapatinib (range: 100-3000 in three-fold dilutions) in combination with trametinib (range: 0.01-100 in three-fold dilution). BLISS scores were calculated based on combination assays as shown in FIG. 4A. FIG. 13B. shows absolute BLISS score of the indicated drugs in combination with trametinib in Ras-mutant relative to RAF-mutant cell lines demonstrates selective synergy in Ras-mutant cell lines for Compound 21 compared to sarcatinib and lapatinib. FIGS. 13C-13D show log of the combination index (CI) graphs of Compound 21 in combination with trametinib in HCT-116 vs. SK-MEL-239 cells as compared to the fractional effect (Fa). Negative CI over a broad Fa range within HCT-116, but not SK-MEL-239, indicates strong synergy.

DETAILED DESCRIPTION

Figure 1:
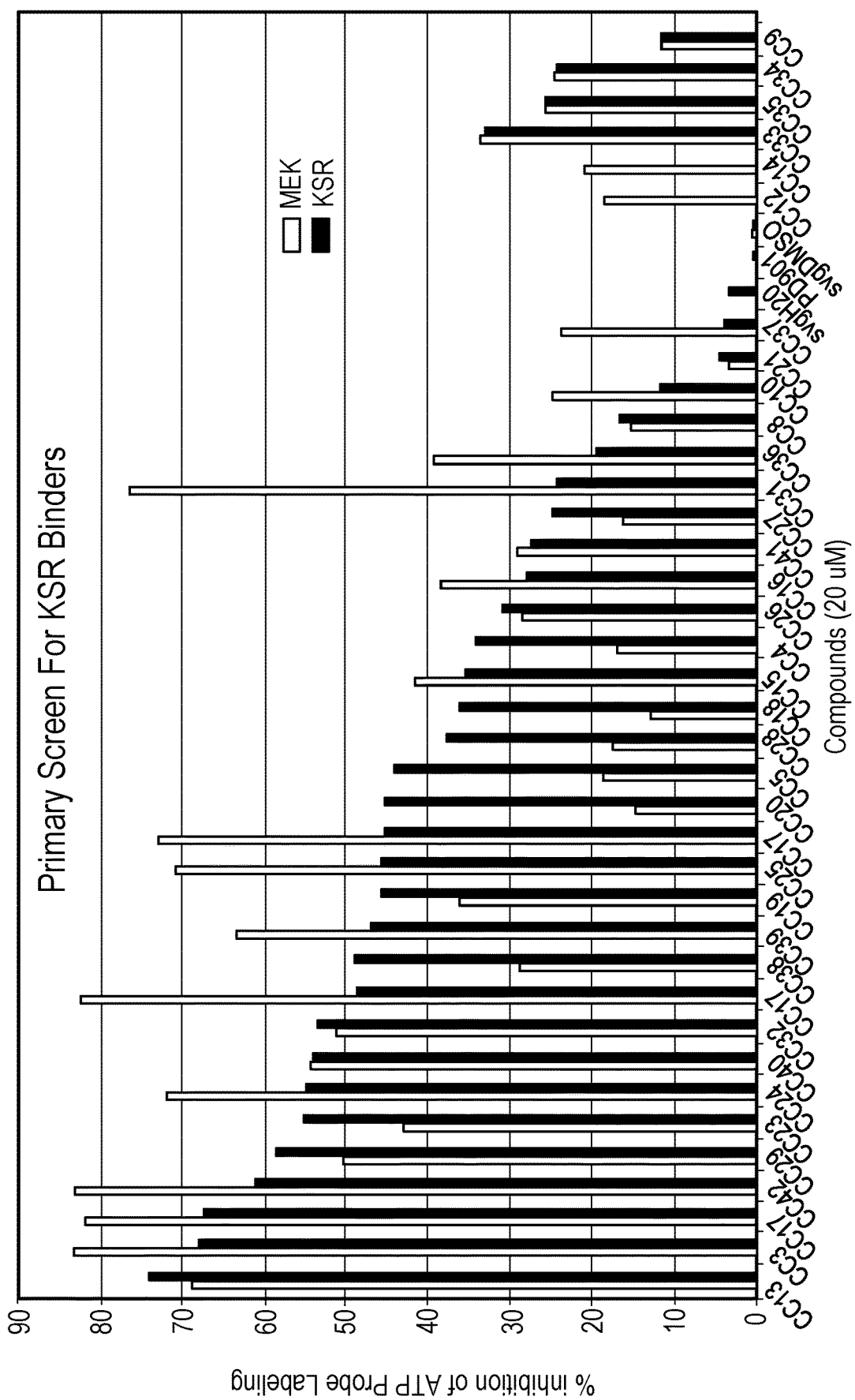
FIG. 1 shows results of a screening assay measuring % inhibition of ATP probe labeling. Left grey bars=MEK; Right grey bars=KSR.

Combination drugs are increasingly recognized as a therapeutic modality for a variety of complex diseases including cancer (see, e.g., Glickman et al., Cell, 2012, 148(6), 1089-1098). In particular, in areas where rapid development of resistance to monotherapy is a major concern, drug combinations may be required to improve treatment responses, minimize adverse events, or minimize development of resistance. In the setting of cancer, combination approaches have primarily focused on three strategies including co-targeting of a single pathway (see e.g., Chapman et al., Cancer Cell, 2014, 26(5), 603-604), different pathways (see e.g., Vora et al., Cancer Cell, 2014, 26(1), 136-149), or compensatory pathways (see e.g., Carver et al., Cancer Cell, 2011, 19(5), 575-586).

Genetic screens conducted in Drosophila and C. Elegans suggested KSR as selectively essential for Ras driven tumors (see e.g., Downward, Cell, 1995, 83(6), 831-834; Kornfeld et al., Cell, 1995, 83(6), 903-913; Sundaram et al., Cell, 1995, 83(6), 889-901; and Therrien et al., Cell, 1995, 83(6), 879-888). This phenotype, where point mutations in KSR disable Ras-driven tumors but not other aspects of Ras related biology such as normal growth and division, likely stems from KSR's function as a scaffold for core enzymes in multiple Ras pathways. For example, KSR controls Ras-dependent proliferation via direct interactions with several kinases in the MAPK cascade and also metabolism via AMP-activated protein kinase signaling (see e.g., Costanzo-Garvey et al., Cell Metab. 2009, 10(5), 366-378; Roy et al., Genes Dev. 2002, 16(4), 427-438; and Ritt et al., Methods Enzymol. 2006, 407, 224-237).

KSR belongs to a family of highly related kinases, including KSR1 and KSR2, and the human RAF kinases (A-RAF, B-RAF, C-RAF). KSR1 and KSR2 share 61% overall amino acid identity, and 71% amino acid identity between kinase domains. While both KSR1 and KSR2 can interact with RAF, MEK, and ERK, KSR1 has been shown to be prominently involved in MAPK signaling, while KSR2 was shown to impact cell growth through its interaction and functional impact on AMPK (see e.g., Fernandez et al., Mol. Cell. Biol. 2012, 32(18), 3718-3731). This has been further supported by the fact that KSR1 knockout mice exhibit a rough hair phenotype, while KSR2 knockout mice display a severe obese phenotype (see e.g., Costanzo-Garvey et al., Cell Metab. 2009, 10(5), 366-378; Fernandez et al., Mol. Cell. Biol. 2012, 32(18), 3718-3731; and Lozano et al., Cancer Res. 2003, 63(14), 4232-4238). Knockout of KSR1 in RAS-driven tumor mouse models completely blocks tumorigenesis. Therefore, unlike MEK1/2 and ERK1/2, in which knockdown is lethal in adult mice, KSR1 appears to be essential for RAS-driven tumorigenesis but not required for normal homeostasis (see e.g., Blasco et al., Cancer Cell, 2011, 19(5), 652-653).

The non-conventional role of KSR as a catalytically compromised kinase (i.e. pseudokinase) has slowed drug development projects (see e.g., Dar, Biochem Soc. Trans. 2013, 41(4), 987-994 and Brennan et al., Nature, 2011, 472(7343), 366-369). Current models suggest that KSR functions as a scaffold to potentiate Ras signaling through the formation of macromolecular signaling complexes that include the Ras effector kinases RAF and MEK. In one state, KSR likely forms a high affinity complex with inactive forms of MEK but once engaged by active RasGTP-RAF complexes, KSR adopts a distinct state where it can instead drive MEK phosphorylation by RAF. Small molecules that could antagonize KSR dependent activities would be valuable tools that could be used to functionally annotate the pharmacology of this class of protein in Ras or RAF dependent cancers. Accordingly, the present application provides compounds that are useful as KSR antagonists and methods of using same.

The following abbreviations may be used herein: calc. (calculated); d (doublet); dd (doublet of doublets); DMSO (dimethylsulfoxide); Et (ethyl); EtOAc (ethyl acetate); g (gram(s)); h (hour(s)); Hz (hertz); J (coupling constant); KSR (Kinase Suppressor of Ras); KSR2(KD) (human KSR2 kinase domain); KSRi (KSR inactive state); $K_3PO_4$ (tripotassium phosphate); LCMS (liquid chromatography-mass spectrometry); m (multiple); M (molar); mM (millimolar); Me (methyl); mg (milligram(s)); $MgCl_2$ (magnesium chloride); min. (minutes(s)); mL (milliliter(s)); mmol (millimole(s)); mol % (mole percent); MS (Mass spectrometry); NaCl (sodium chloride); NMR (nuclear magnetic resonance spectroscopy); ppm (parts per million); t (triplet or tertiary); μg (microgram(s)); μL (microliter(s)); μM (micromolar); M.O.I. (multiplicity of infection).

Compounds and Pharmaceutical Compositions

The present application provides, inter alia, a compound of Formula I:

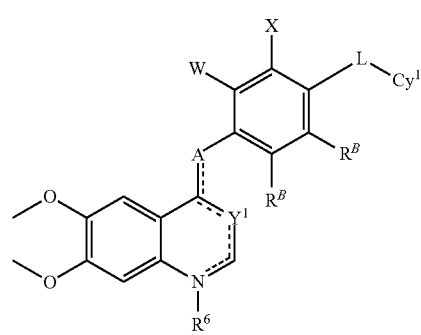

or a pharmaceutically acceptable salt thereof, wherein:
===== indicates a single or double bond;
$Y^1$ is N or CH;
A is selected from the group consisting of N, NH, N(C$_{1-4}$ alkyl), S, O, C(=O), and C$_{1-3}$ alkylene, wherein the C$_{1-3}$ alkylene is optionally substituted by a substituent selected from the group consisting of OH, NH$_2$, NH(C$_{1-4}$ alkyl), and NH(C$_{2-4}$ alkenyl);
L is selected from the group consisting of O, NH, S, C(=O), and C$_{1-3}$ alkylene, wherein the C$_{1-3}$ alkylene is optionally substituted by a substituent selected from the group consisting of OH, NH$_2$, NH(C$_{1-4}$ alkyl), and NH(C$_{2-4}$ alkenyl);

W and X are each independently selected from the group consisting of H, halo, and C$_{1-4}$ alkyl;

each R$^B$ is H; or alternatively, two R$^B$ groups come together, in combination with the carbon atoms to which they are attached, to form a C$_{3-6}$ carbocyclic group or a 3-6 membered heterocyclic group;

Cy$^1$ is selected from the group consisting of:

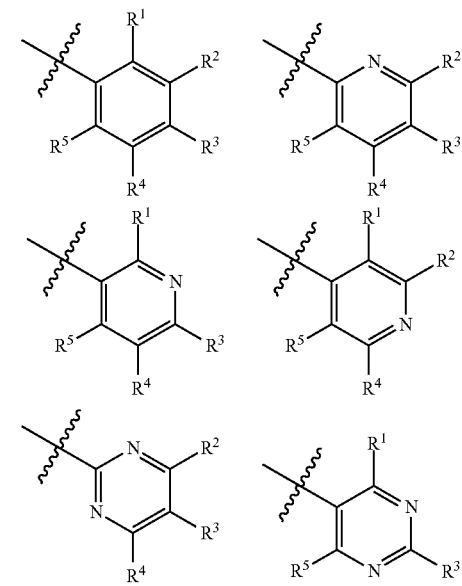

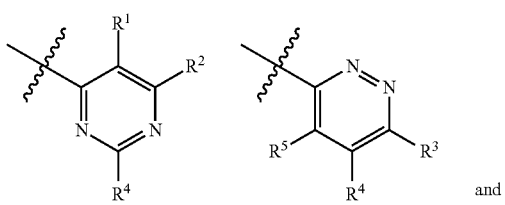

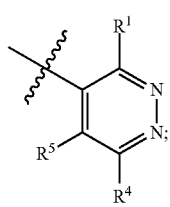

R$^1$ and R$^5$ are each independently selected from the group consisting of H, halo, OH, C$_{1-4}$ alkyl, and C$_{1-4}$ haloalkyl;

R$^3$ is selected from the group consisting of H and halo; and

R$^2$ and R$^4$ are each independently selected from the group consisting of H and halo; and R$^6$ is absent or selected from the group consisting of H and C$_{1-4}$ alkyl.

In some embodiments, when A is NH, Y$^1$ is N, L is O, and Cy$^1$ is

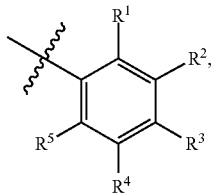

then at least one of W, X, R$^B$, R$^1$, R$^2$, R$^4$, R$^5$, and R$^6$ is not H.

In some embodiments, Cy$^1$ is selected from the group consisting of:

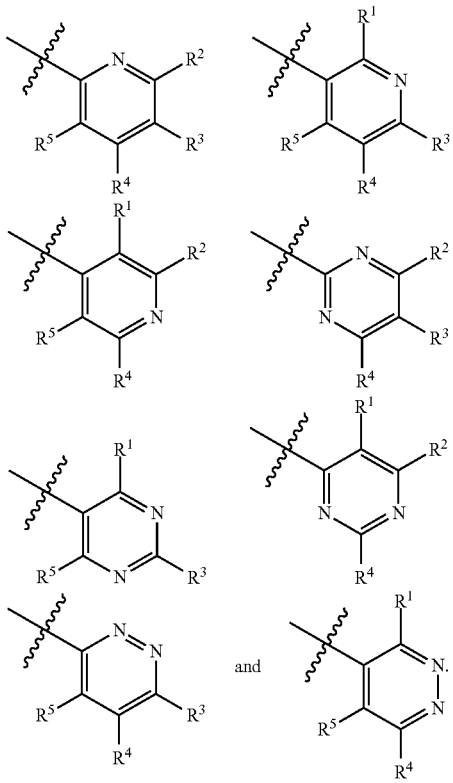

In some embodiments, the compound of Formula I is a compound of Formula Ia:

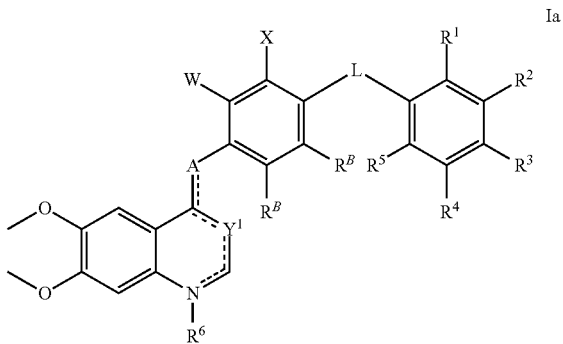

Ia or a pharmaceutically acceptable salt thereof, wherein $Y^1$, A, W, X, $R^B$, L, $R^1$, $R^2$, $R^3$, $R^4$, $R^5$, and $R^6$ are as defined above for compounds of Formula I.

In some embodiments, $Y^1$ is N. In some embodiments, $Y^1$ is CH.

In some embodiments, A is selected from the group consisting of N, NH, N(CH$_3$), S, O, (C=O), CH(OH), CH$_2$, CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH(CH$_3$)$_2$), CH(NHC(CH$_3$)$_3$), and CH(NHCH$_2$CH=CH$_2$). In some embodiments, A is selected from the group consisting of N, NH, N(CH$_3$), S, O, and CH$_2$. In some embodiments, A is NH. In some embodiments, A is N(CH$_3$). In some embodiments, A is S. In some embodiments, A is O. In some embodiments, A is CH$_2$. In some embodiments, A is C(=O). In some embodiments, A is CH(OH). In some embodiments, A is CH(NH$_2$). In some embodiments, A is selected from the group consisting of CH(OH), CH(NH$_2$), CH(NHCH$_3$), CH(NHCH$_2$CH$_3$), CH(NHCH$_2$CH$_2$CH$_3$), CH(NHCH (CH$_3$)$_2$), CH(NHCH$_2$CH(CH$_3$)$_2$), CH(NHC(CH$_3$)$_3$), and CH(NHCH$_2$CH=CH$_2$).

In some embodiments, L is selected from the group consisting of O, NH, S, C(=O), CH(OH), CH$_2$, CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH(CH$_3$)$_2$), CH(NHC (CH$_3$)$_3$), and CH(NHCH$_2$CH=CH$_2$). In some embodiments, L is selected from the group consisting of O, NH, S, and CH$_2$. In some embodiments, L is O. In some embodiments, L is NH. In some embodiments, L is S. In some embodiments, L is CH$_2$. In some embodiments, L is CH(OH). In some embodiments, L is CH(NH$_2$). In some embodiments, L is selected from the group consisting of CH(OH), CH(NH$_2$), CH(NHCH$_3$), CH(NHCH$_2$CH$_3$), CH(NHCH$_2$CH$_2$CH$_3$), CH(NHCH(CH$_3$)$_2$), CH(NHCH$_2$CH (CH$_3$)$_2$), CH(NHC(CH$_3$)$_3$), and CH(NHCH$_2$CH=CH$_2$).

In some embodiments, W is selected from the group consisting of H, halo, and CH$_3$. In some embodiments, W is selected from the group consisting of H, F, Cl, Br, and C$_{1-4}$ alkyl. In some embodiments, W is selected from the group consisting of H, F, Cl, Br, and CH$_3$. In some embodiments, W is selected from the group consisting of H, Cl, Br, and CH$_3$. In some embodiments, W is H. In some embodiments, W is halo. In some embodiments, W is Cl or Br. In some embodiments, W is C$_{1-4}$ alkyl. In some embodiments, W is CH$_3$.

In some embodiments, X is selected from the group consisting of H, halo, and CH$_3$. In some embodiments, X is selected from the group consisting of H, F, Cl, Br, and C$_{1-4}$ alkyl. In some embodiments, X is selected from the group consisting of H, F, Cl, Br, and CH$_3$. In some embodiments, X is H. In some embodiments, X is halo. In some embodiments, X is selected from the group consisting of F, Cl, and Br. In some embodiments, X is F. In some embodiments, X is C$_{1-4}$ alkyl. In some embodiments, X is CH$_3$.

In some embodiments, each $R^B$ is H. In some embodiments, two $R^B$ groups come together, in combination with the carbon atoms to which they are attached, to form a C$_{3-6}$ carbocyclic group. In some embodiments, two $R^B$ groups come together, in combination with the carbon atoms to which they are attached, to form a C$_{3-6}$ carbocyclic group selected from:

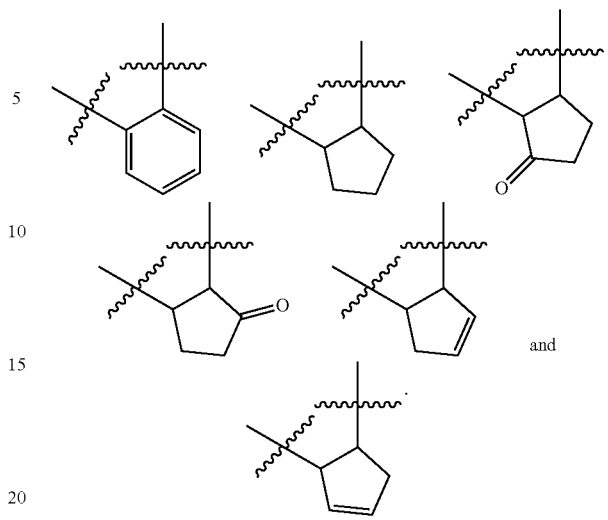

In some embodiments, two $R^B$ groups come together, in combination with the carbon atoms to which they are attached, to form a phenyl group.

In some embodiments, two $R^B$ groups come together, in combination with the carbon atoms to which they are attached, to form a 3-6 membered heterocyclic group. In some embodiments, two $R^B$ groups come together, in combination with the carbon atoms to which they are attached, to form a 3-6 membered heterocyclic group selected from:

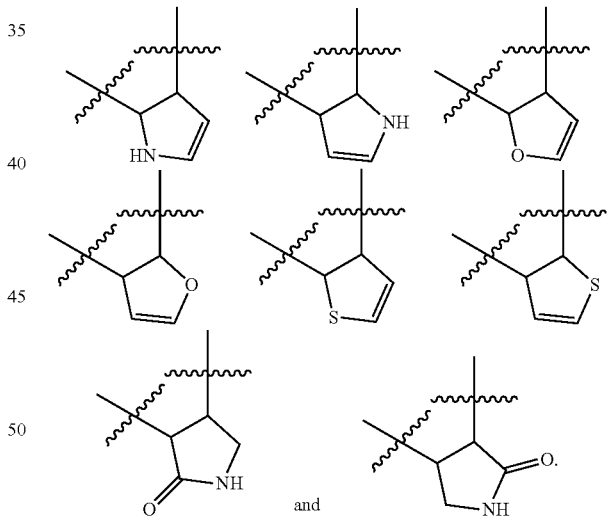

In some embodiments, $R^1$ is selected from the group consisting of H, halo, OH, and C$_{1-4}$ haloalkyl. In some embodiments, $R^1$ is selected from the group consisting of H, halo, OH, and CF$_3$. In some embodiments, $R^1$ is selected from the group consisting of H, F, Cl, Br, OH, and C$_{1-4}$ haloalkyl. In some embodiments, $R^1$ is selected from the group consisting of H, F, Cl, Br, OH, and CF$_3$. In some embodiments, $R^1$ is selected from the group consisting of H, F, OH, and CF$_3$.

In some embodiments, $R^2$ is selected from the group consisting of H, F, Cl, and Br. In some embodiments, $R^2$ is selected from the group consisting of H, F, and Cl. In some embodiments, $R^2$ is selected from the group consisting of H and F. In some embodiments, $R^2$ is H. In some embodiments, $R^2$ is F.

In some embodiments, $R^3$ is H. In some embodiments, $R^3$ is halo. In some embodiments, $R^3$ is selected from the group consisting of F, Cl, and Br. In some embodiments, $R^3$ is Cl. In some embodiments, $R^3$ is selected from the group consisting of H and Cl.

In some embodiments, $R^4$ is selected from the group consisting of H, F, Cl, and Br. In some embodiments, $R^4$ is selected from the group consisting of H and F. In some embodiments, $R^4$ is H. In some embodiments, $R^4$ is F.

In some embodiments, $R^5$ is selected from the group consisting of H, halo, OH, and $C_{1-4}$ haloalkyl. In some embodiments, $R^5$ is selected from the group consisting of H, halo, OH, and $CF_3$. In some embodiments, $R^5$ is selected from the group consisting of H, F, Cl, Br, OH, and $C_{1-4}$ haloalkyl. In some embodiments, $R^5$ is selected from the group consisting of H, F, Cl, Br, OH, and $CF_3$. In some embodiments, $R^5$ is selected from the group consisting of H, F, OH, and $CF_3$. In some embodiments, $R^5$ is H. In some embodiments, $R^5$ is F. In some embodiments, $R^5$ is OH. In some embodiments, $R^5$ is $CF_3$.

In some embodiments, $R^6$ is absent. In some embodiments, $R^6$ is selected from the group consisting of H and $C_{1-4}$ alkyl. In some embodiments, $R^6$ is selected from the group consisting of H and $CH_3$. In some embodiments, $R^6$ is H. In some embodiments, $R^6$ is $CH_3$.

In some embodiments:
$Y^1$ is N;
A is selected from the group consisting of N, NH, $N(CH_3)$, S, O, and $CH_2$;
L is selected from the group consisting of O, NH, S, and $CH_2$;
W and X are each independently selected from the group consisting of H, halo, and $CH_3$;
each $R^B$ is H; or
alternatively, two $R^B$ groups come together, in combination with the carbon atoms to which they are attached, to form a $C_{3-6}$ carbocyclic group;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl;
$R^2$ and $R^4$ are each independently selected from the group consisting of H and halo; and
$R^6$ is absent or $CH_3$.

In some embodiments:
$Y^1$ is N;
A is selected from the group consisting of N, NH, $N(CH_3)$, S, O, and $CH_2$;
L is selected from the group consisting of O, NH, S, and $CH_2$;
W is selected from the group consisting of H, Cl, Br, and $CH_3$;
X is selected from the group consisting of H, F, Cl, Br, and $CH_3$;
each $R^B$ is H; or
alternatively, two $R^B$ groups come together, in combination with the carbon atoms to which they are attached, to form a $C_{3-6}$ carbocyclic group;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl;
$R^2$ and $R^4$ are each independently selected from the group consisting of H and halo; and
$R^6$ is absent or $CH_3$.

In some embodiments:
$Y^1$ is N;
L is O;
A is NH;
W is selected from the group consisting of H, Cl, Br, and $CH_3$;
X is selected from the group consisting of H, F, Cl, Br, and $CH_3$;
each $R^B$ is H; or
alternatively, two $R^B$ groups come together, in combination with the carbon atoms to which they are attached, to form a $C_{3-6}$ carbocyclic group;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl; and
$R^2$ and $R^4$ are each independently selected from the group consisting of H and halo; and
$R^6$ is absent.

In some embodiments, the compound of Formula I is a compound of Formula Ia:

Ia or a pharmaceutically acceptable salt thereof, wherein:
------ indicates a single or double bond;
$Y^1$ is N or CH;
A is selected from the group consisting of N, NH, $N(C_{1-4}$ alkyl), S, O, and $C_{1-3}$ alkylene;
L is selected from the group consisting of O, NH, S, and $C_{1-3}$ alkylene;
W and X are each independently selected from the group consisting of H, halo, and $C_{1-4}$ alkyl;
each $R^B$ is H; or
alternatively, two $R^B$ groups come together, in combination with the carbon atoms to which they are attached, to form a $C_{3-6}$ carbocyclic group;
$R^1$ and $R^5$ are each independently selected from the group consisting of H, halo, OH, $C_{1-4}$ alkyl, and $C_{1-4}$ haloalkyl;
$R^3$ is selected from the group consisting of H and halo; and
$R^2$ and $R^4$ are each independently selected from the group consisting of H and halo; and
$R^6$ is absent or selected from the group consisting of H and $C_{1-4}$ alkyl.

In some embodiments, when A is NH, $Y^1$ is N, and L is O, then at least one of W, X, $R^B$, $R^1$, $R^2$, $R^4$, $R^5$, and $R^6$ is not H.

In some embodiments, the compound of Formula I is a compound of Formula Ib:

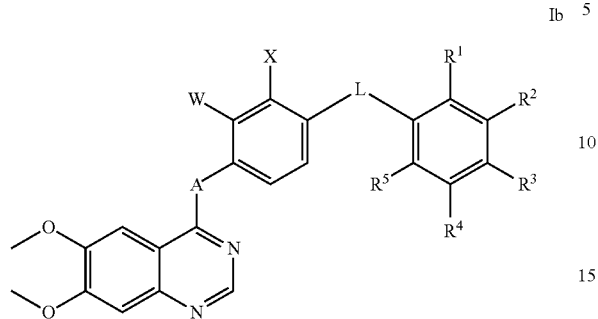

Ib or a pharmaceutically acceptable salt thereof, wherein A, W, X, L, $R^1$, $R^2$, $R^3$, $R^4$, and $R^5$ are as defined above for compounds of Formula I.

In some embodiments, the compound of Formula I is a compound of Formula Ic:

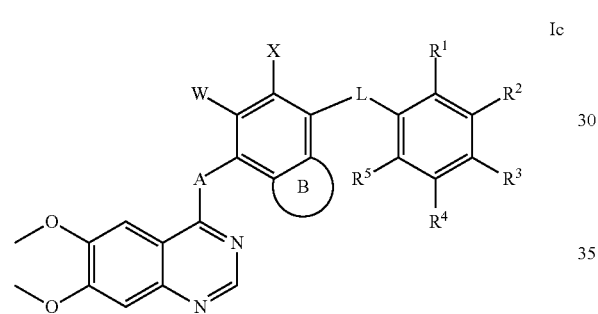

Ic or a pharmaceutically acceptable salt thereof, wherein B is a $C_{3-6}$ carbocyclic group or a 3-6 membered heterocyclic group, and A, W, X, L, $R^1$, $R^2$, $R^3$, $R^4$, and $R^5$ are as defined above for compounds of Formula I.

In some embodiments, the compound of Formula I is a compound of Formula Id:

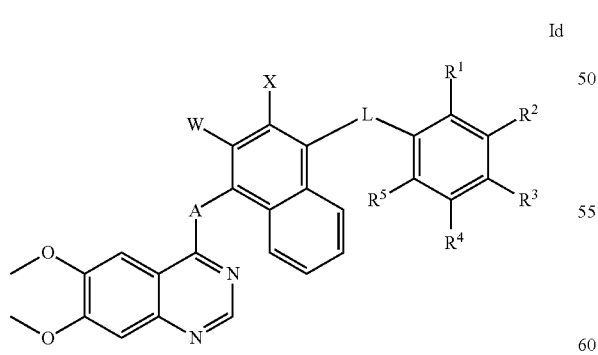

Id or a pharmaceutically acceptable salt thereof, wherein A, W, X, L, $R^1$, $R^2$, $R^3$, $R^4$, and $R^5$ are as defined above for compounds of Formula I.

In some embodiments, the compound of Formula I is selected from the group consisting of:

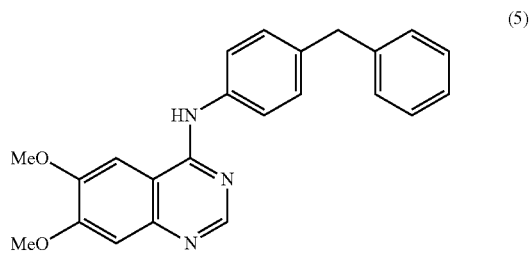

(5)

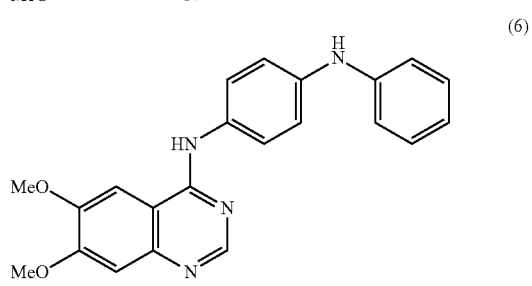

(6)

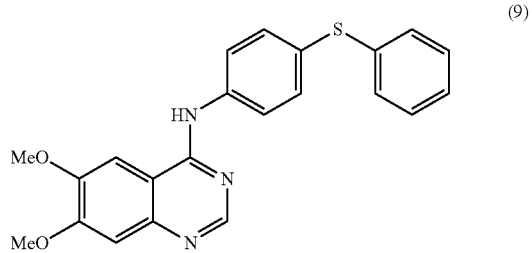

(9)

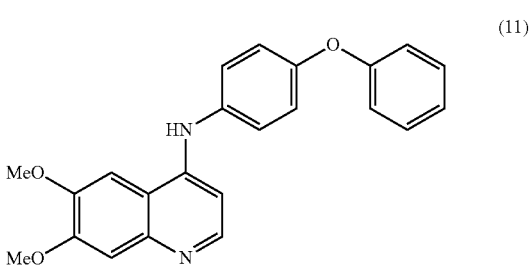

(11)

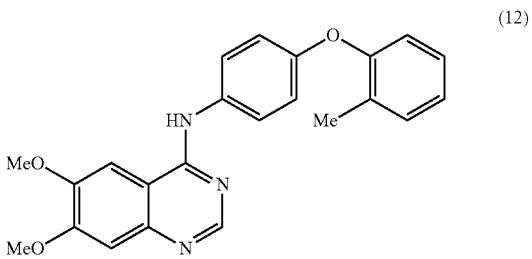

(12)

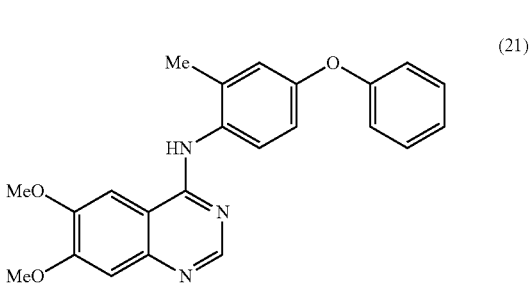

(21)

-continued
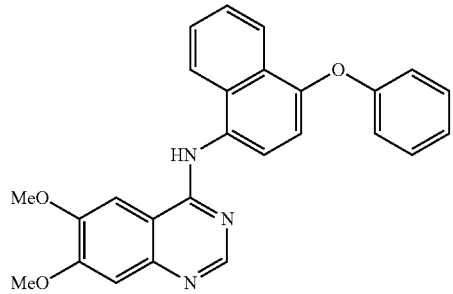
(23)
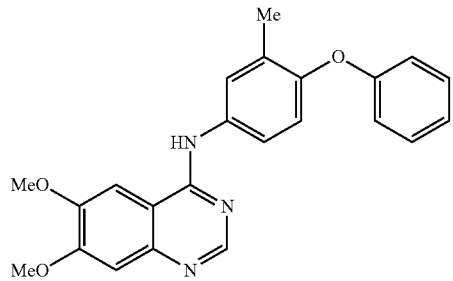
(24)
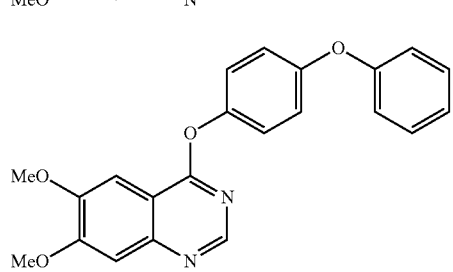
(28)
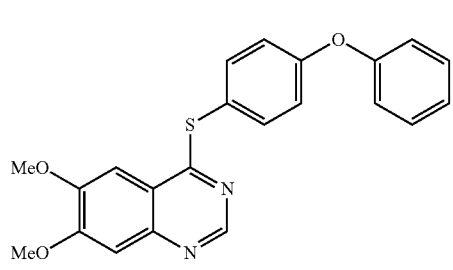
(31)
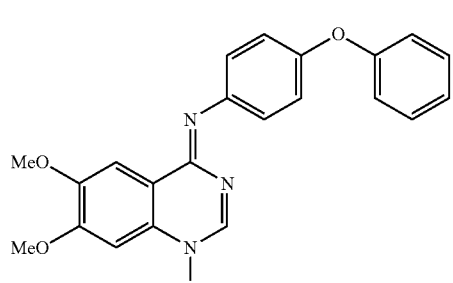
(32)
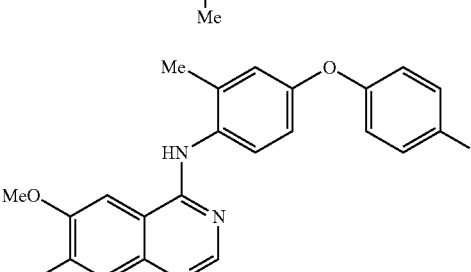
(37)
-continued
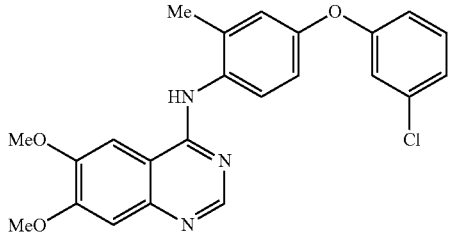
(38)
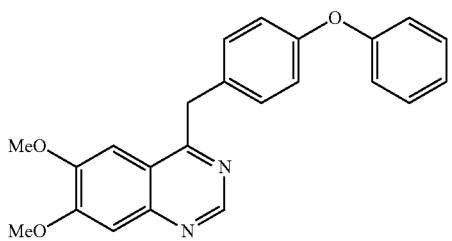
(43)
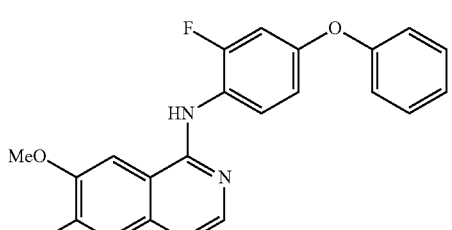
(44)
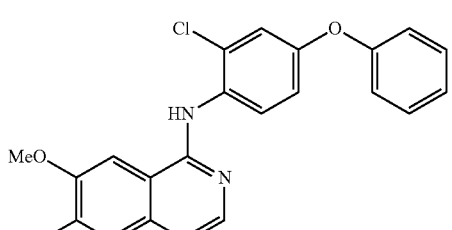
(45)
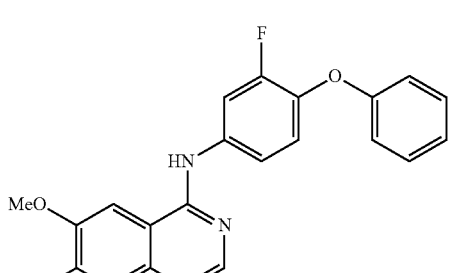
(46)
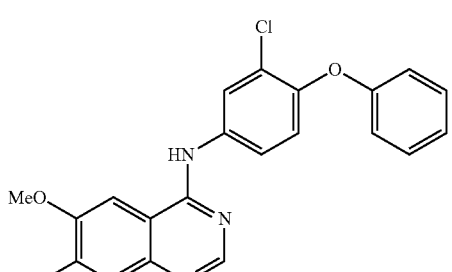
(47)

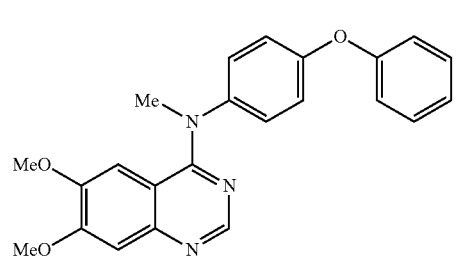
(49)
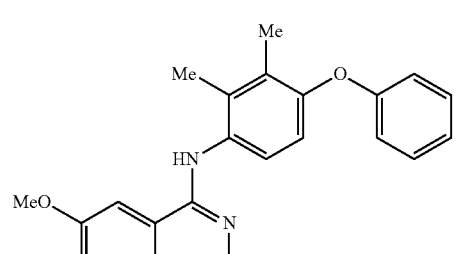
(50)
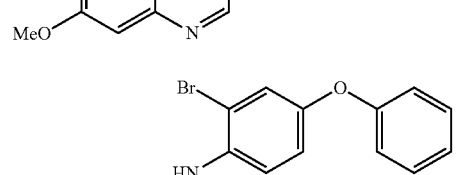
(51)
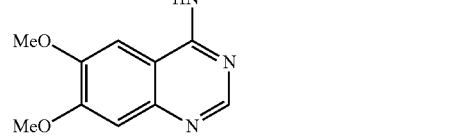
(54)
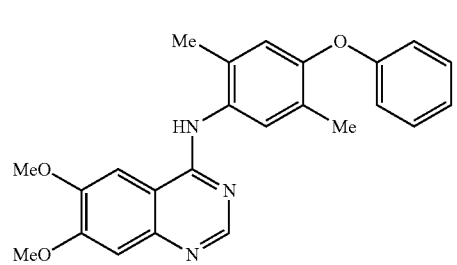
(55)
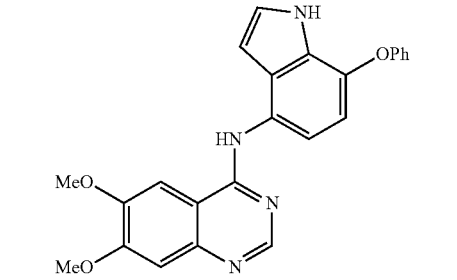
(56)
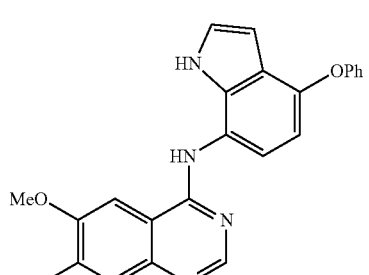
(57)
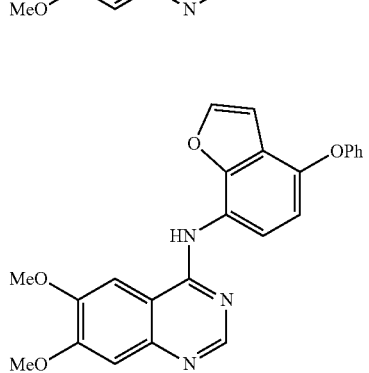
(58)
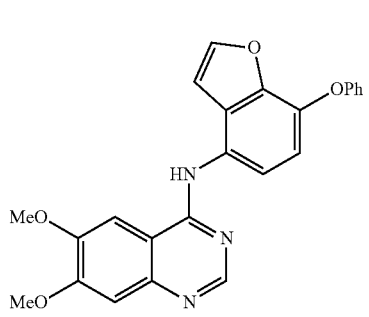
(59)
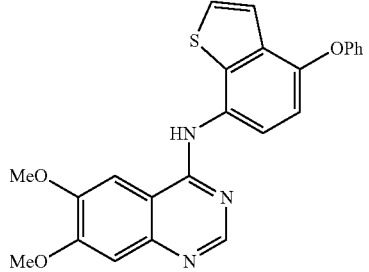
(60)
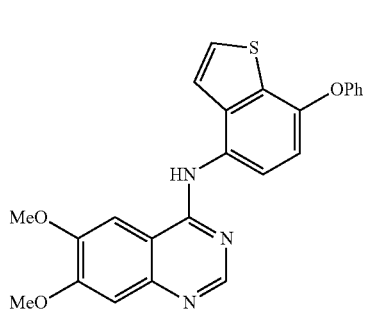
(61)

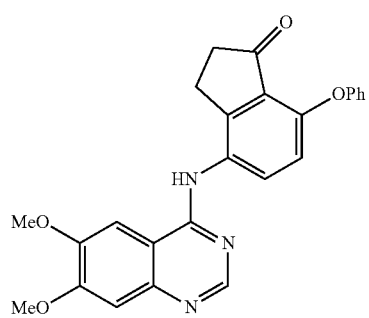
(62)
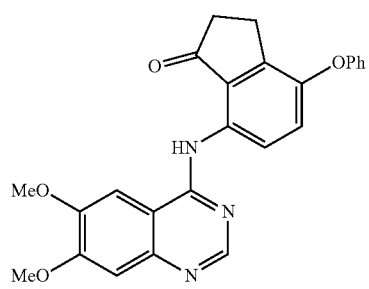
(63)
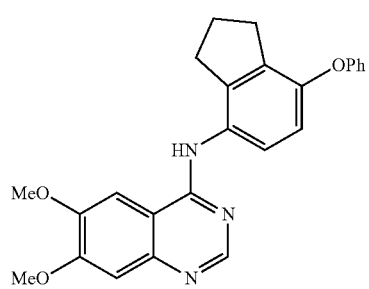
(64)
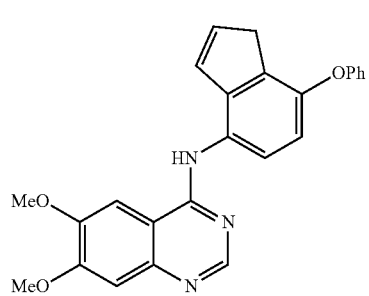
(65)
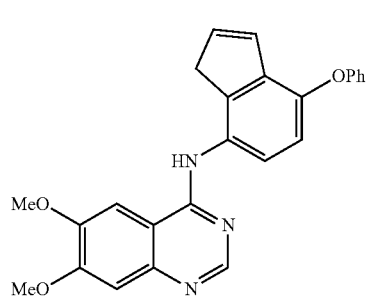
(66)
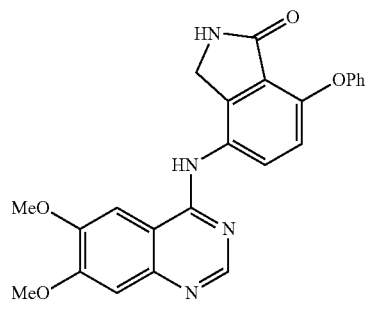
(67)
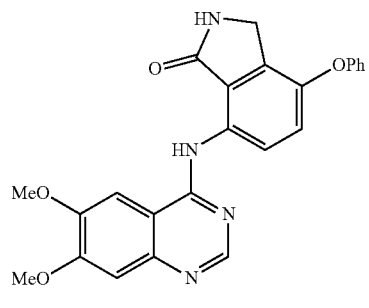
(68)
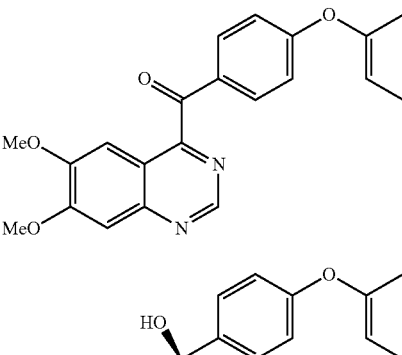
(69)
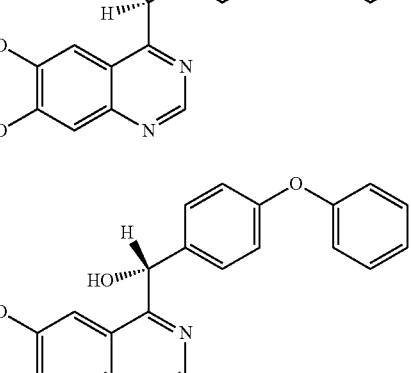
(70)
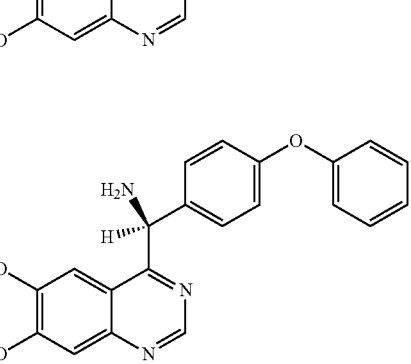
(71)
(72)

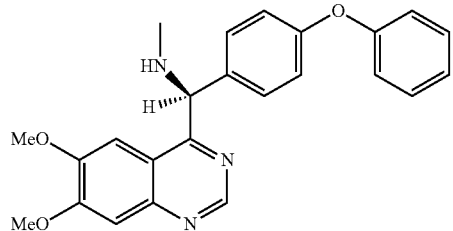
(73)
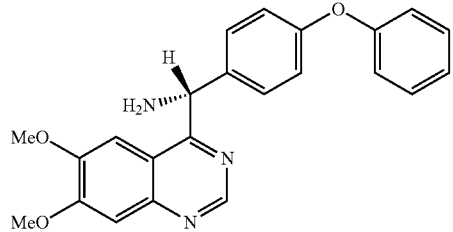
(74)
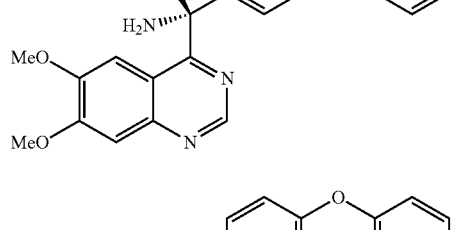
(75)
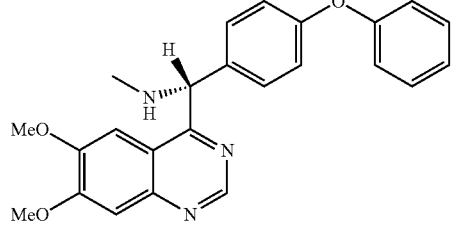
(76)
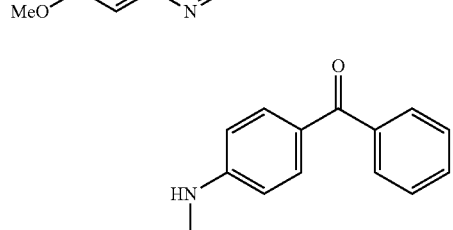
(77)
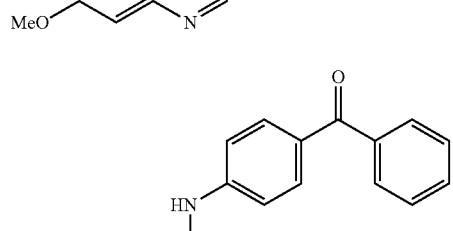
(78)
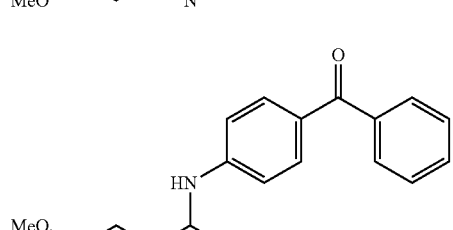
(79)
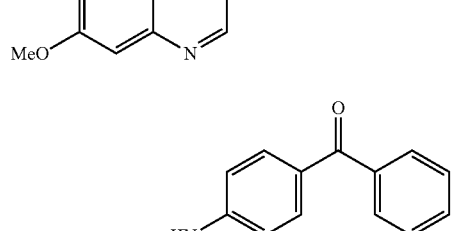
(80)
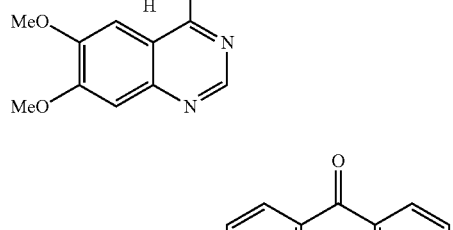
(81)
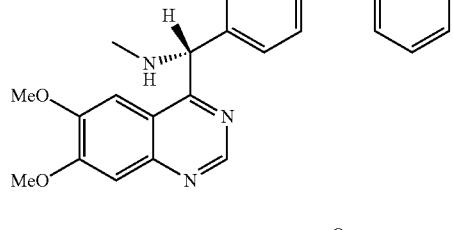
(82)
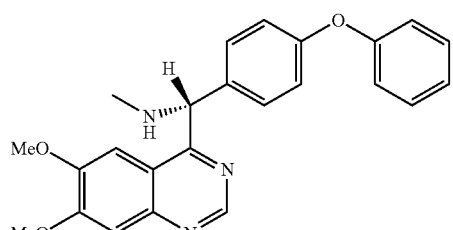
(83)

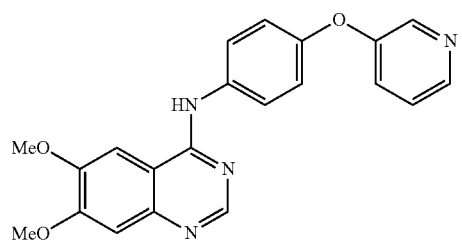
(84)
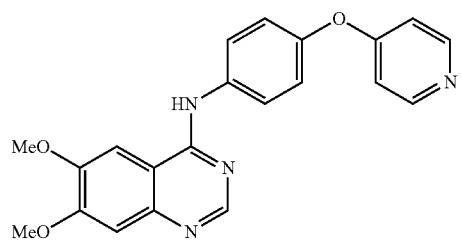
(85)
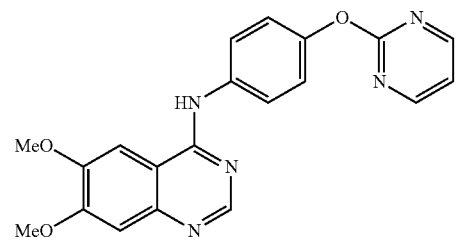
(86)
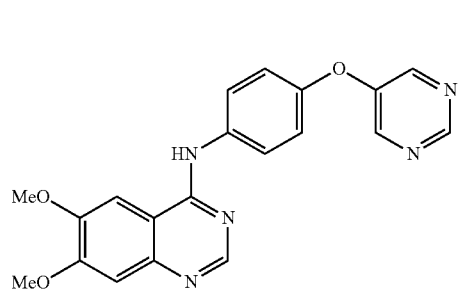
(87)
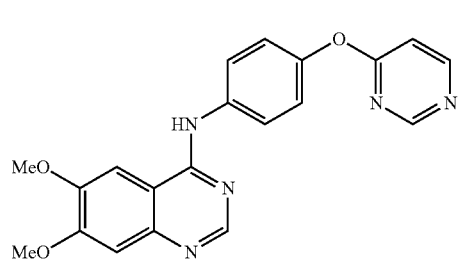
(88)
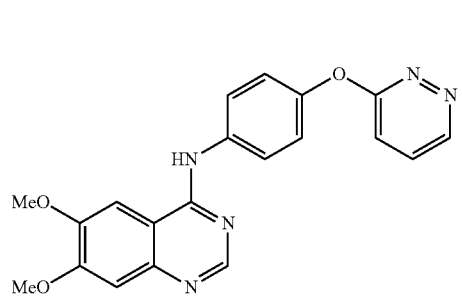
(89)
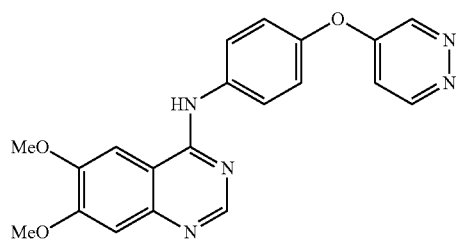
(90)
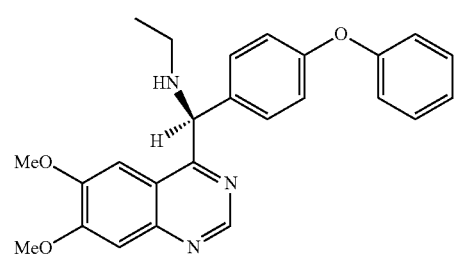
(95)
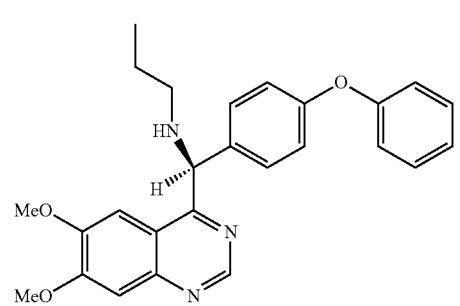
(96)
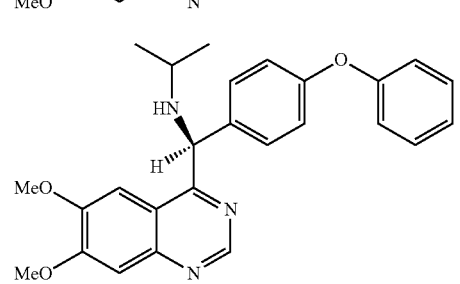
(97)
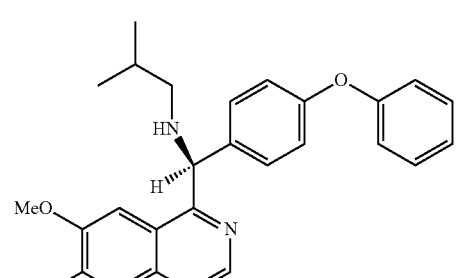
(98)
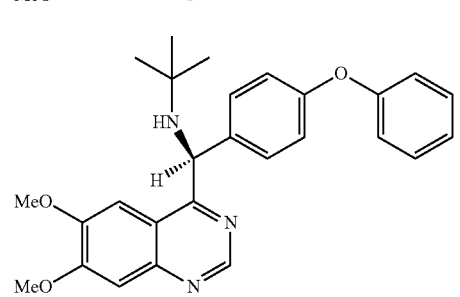
(99)

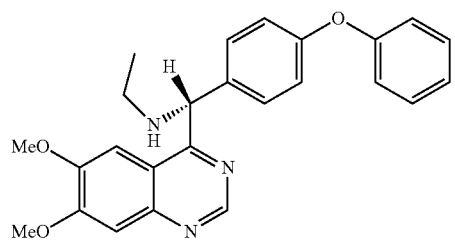
(100)
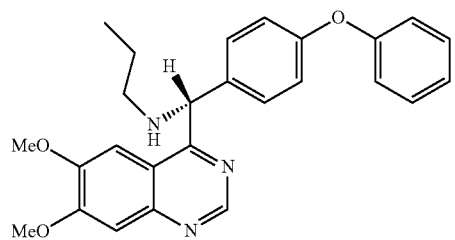
(101)
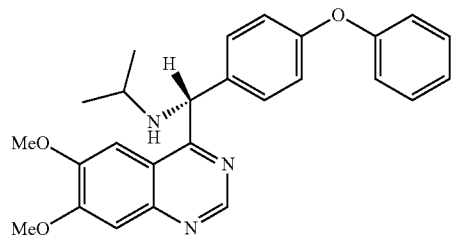
(102)
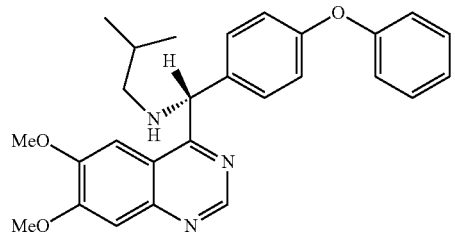
(103)
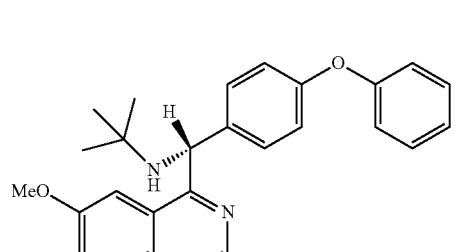
(104)
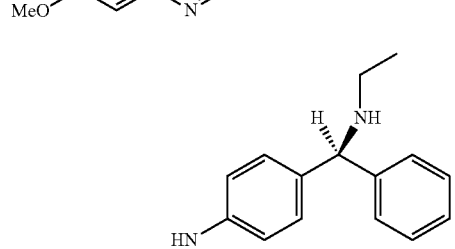
(105)
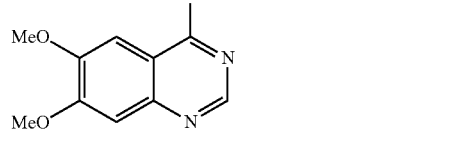
(106)
(107)
(108)
(109)

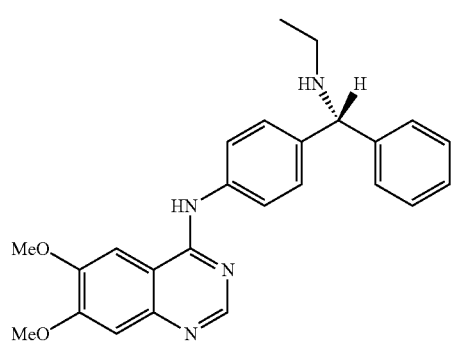
(110)
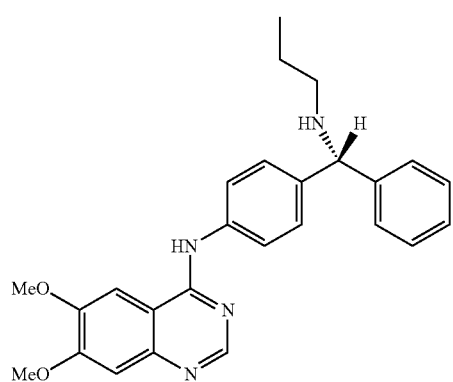
(111)
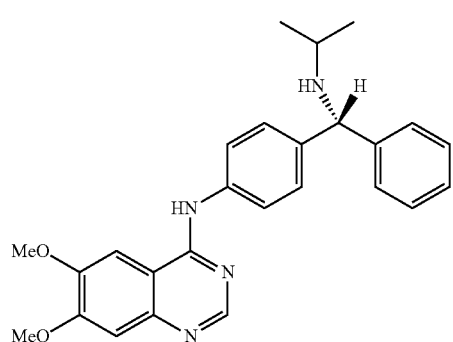
(112)
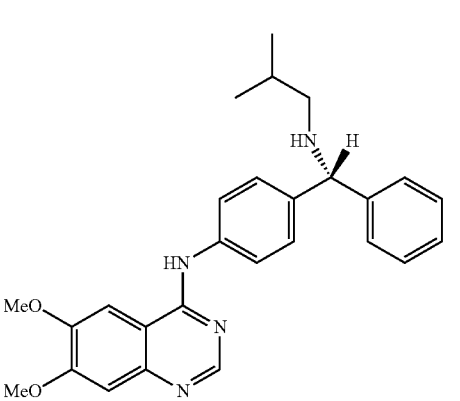
(113)
and
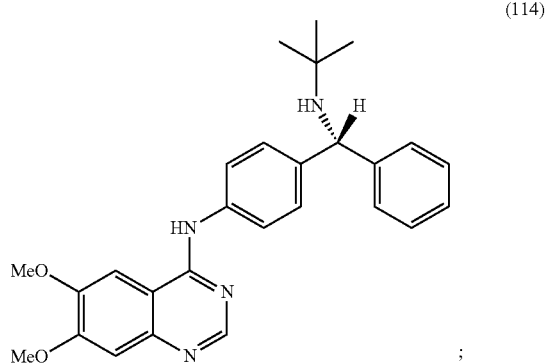
(114)
or a pharmaceutically acceptable salt thereof.
In some embodiments, the compound of Formula I is selected from the group consisting of:
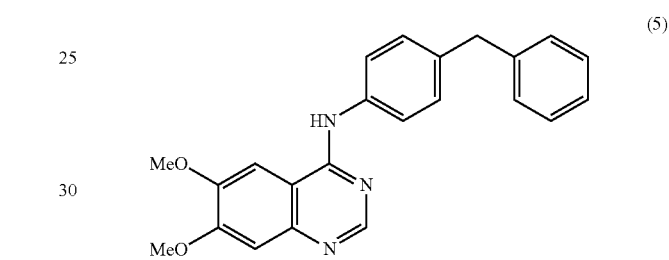
(5)
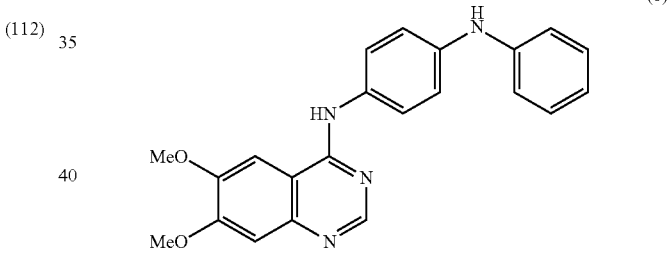
(6)
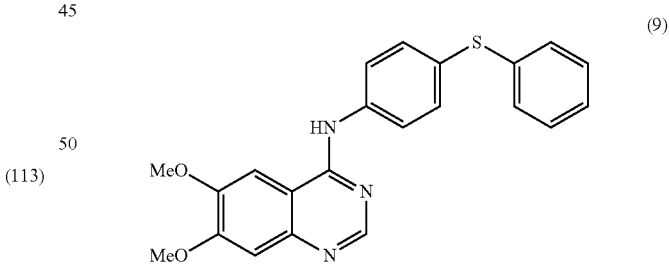
(9)
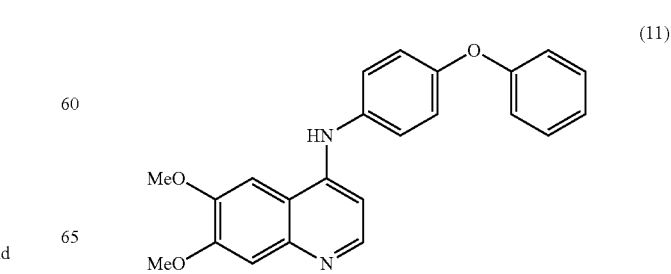
(11)

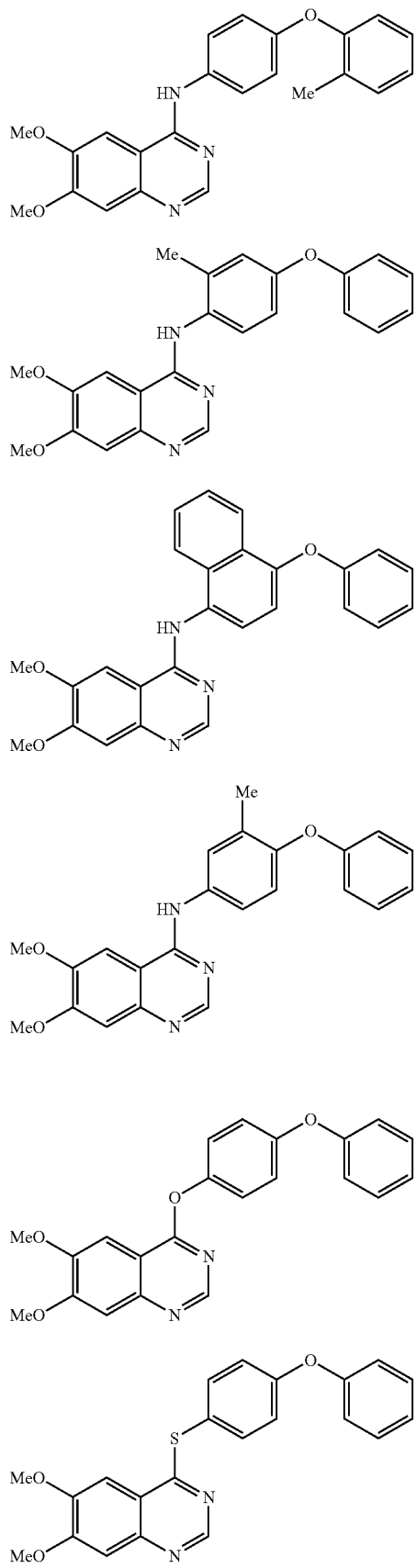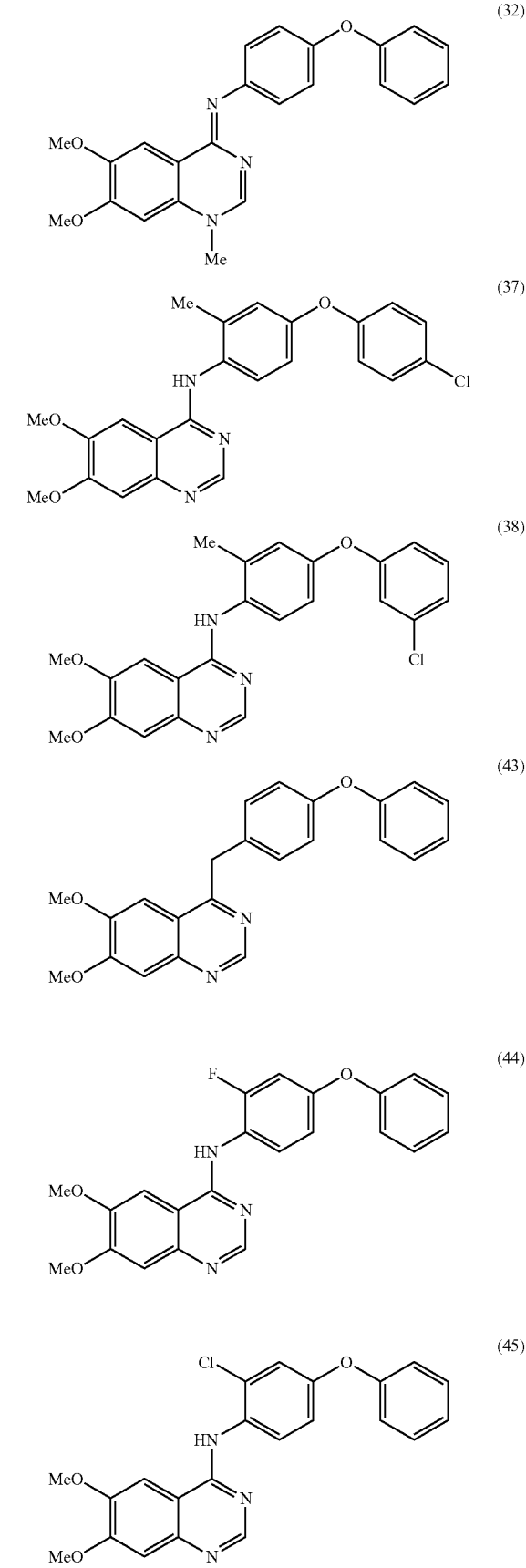

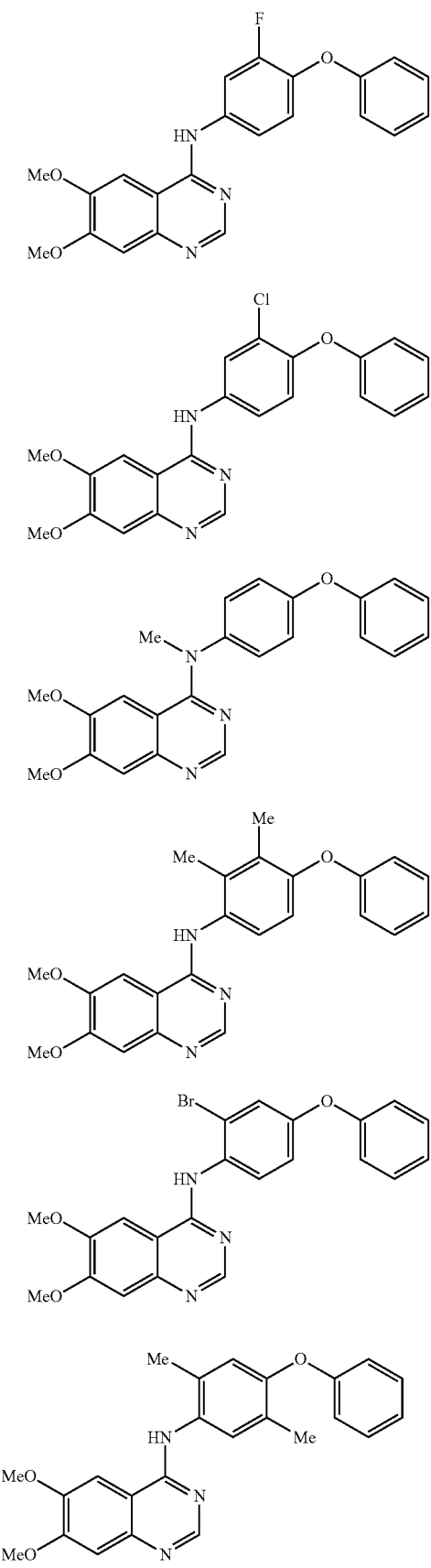

(46)

(47)

(49)

(50)

(51)

(54)

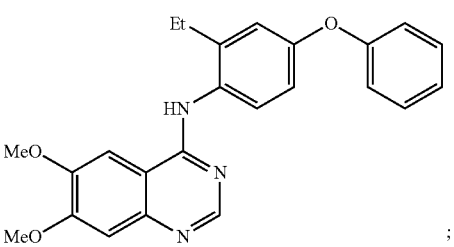

(55)

or a pharmaceutically acceptable salt thereof.

In some embodiments, the compound of Formula I is a pharmaceutically acceptable salt. In some embodiments, the compound of Formula I is a hydrochloride (i.e. HCl) salt. In some embodiments, the compound of Formula I is a 2,2,2-trifluoroacetic acid (i.e., TFA) salt.

In some embodiments, the compound is 6,7-dimethoxy-N-(2-methyl-4-phenoxyphenyl)quinazolin-4-amine (21), or a pharmaceutically acceptable salt thereof. In some embodiments, the compound is 6,7-dimethoxy-N-(2-methyl-4-phenoxyphenyl)quinazolin-4-amine 2,2,2-trifluoroacetate (21.TFA). In some embodiments, the compound is 6,7-dimethoxy-N-(2-methyl-4-phenoxyphenyl)quinazolin-4-amine hydrochloride (21.HCl).

The present application further provides a compound of Formula II:

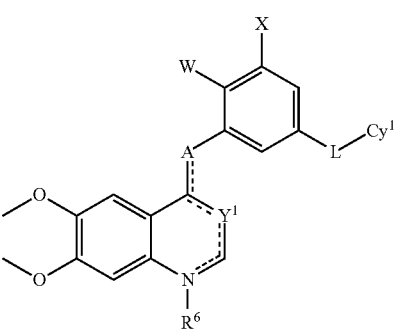

II or a pharmaceutically acceptable salt thereof, wherein:

===== indicates a single or double bond;

$Y^1$ is N or CH;

A is selected from the group consisting of N, NH, N($C_{1-4}$ alkyl), S, O, C(=O), and $C_{1-3}$ alkylene, wherein the $C_{1-3}$ alkylene is optionally substituted by a substituent selected from the group consisting of OH, $NH_2$, NH($C_{1-4}$ alkyl), and NH($C_{2-4}$ alkenyl);

L is selected from the group consisting of O, NH, S, C(=O), and $C_{1-3}$ alkylene, wherein the $C_{1-3}$ alkylene is optionally substituted by a substituent selected from the group consisting of OH, $NH_2$, NH($C_{1-3}$ alkyl), and NH($C_{2-4}$ alkenyl);

W and X are each independently selected from the group consisting of H, halo, and $C_{1-4}$ alkyl;

and

Cy¹ is selected from the group consisting of:

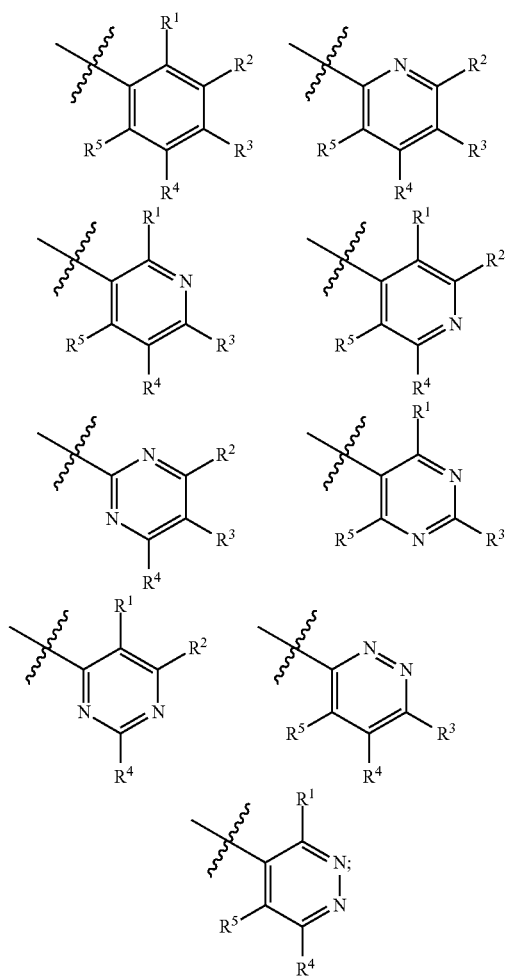

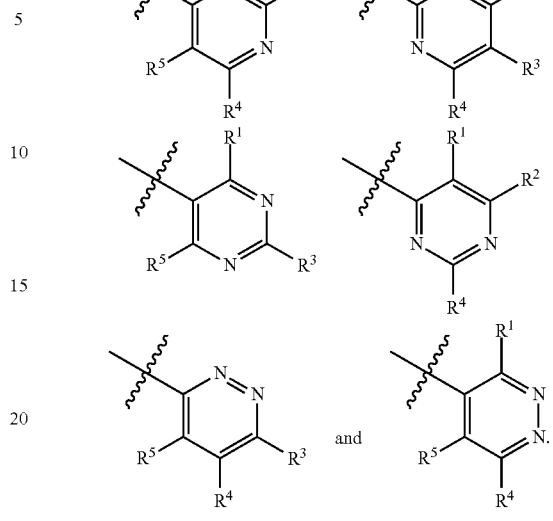

and

R¹ and R⁵ are each independently selected from the group consisting of H, halo, OH, $C_{1-4}$ alkyl, and $C_{1-4}$ haloalkyl;

R³ is selected from the group consisting of H and halo; and

R² and R⁴ are each independently selected from the group consisting of H and halo; or alternatively, R⁴ and R⁵ come together, in combination with the carbon atoms to which they are attached, to form a $C_{3-6}$ carbocyclic group or a 3-6 membered heterocyclic group; and R⁶ is absent or selected from the group consisting of H and $C_{1-4}$ alkyl.

In some embodiments, Cy¹ is selected from the group consisting of:

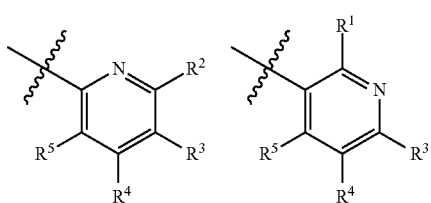

In some embodiments, the compound of Formula II is a compound of Formula IIa:

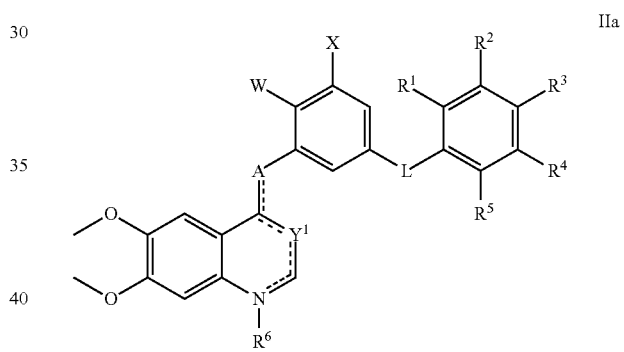

IIa or a pharmaceutically acceptable salt thereof, wherein Y¹, A, W, X, L, R¹, R², R³, R⁴, R⁵, and R⁶ are as defined above for compounds of Formula II.

In some embodiments, Y¹ is N. In some embodiments, Y¹ is CH.

In some embodiments, A is selected from the group consisting of N, NH, N(CH₃), S, O, (C=O), CH(OH), CH₂, CH(NH₂), CH(NHCH₃), CH(NHCH₂CH₃), CH(NHCH₂CH₂CH₃), CH(NHCH(CH₃)₂), CH(NHCH₂CH(CH₃)₂), CH(NHC(CH₃)₃), and CH(NHCH₂CH=CH₂). In some embodiments, A is selected from the group consisting of N, NH, N(CH₃), S, O, and CH₂. In some embodiments, A is NH. In some embodiments, A is N(CH₃). In some embodiments, A is S. In some embodiments, A is O. In some embodiments, A is CH₂. In some embodiments, A is selected from the group consisting of CH(OH), CH(NH₂), CH(NHCH₃), CH(NHCH₂CH₃), CH(NHCH₂CH₂CH₃), CH(NHCH(CH₃)₂), CH(NHCH₂CH(CH₃)₂), CH(NHC(CH₃)₃), and CH(NHCH₂CH=CH₂).

In some embodiments, L is selected from the group consisting of O, NH, S, C(=O), CH(OH), CH₂, CH(NH₂), CH(NHCH₃), CH(NHCH₂CH₃), CH(NHCH₂CH₂CH₃), CH(NHCH(CH₃)₂), CH(NHCH₂CH(CH₃)₂), CH(NHC(CH₃)₃), and CH(NHCH₂CH=CH₂). In some embodiments, L is selected from the group consisting of O, NH, S, and $CH_2$. In some embodiments, L is O. In some embodiments, L is NH. In some embodiments, L is S. In some embodiments, L is $CH_2$. In some embodiments, L is selected from the group consisting of CH(OH), $CH(NH_2)$, CH(N-$HCH_3$), $CH(NHCH_2CH_3)$, $CH(NHCH_2CH_2CH_3)$, CH(N-$HCH(CH_3)_2)$, $CH(NHCH_2CH(CH_3)_2)$, $CH(NHC(CH_3)_3)$, and $CH(NHCH_2CH=CH_2)$.

In some embodiments, W is selected from the group consisting of H, halo, and $CH_3$. In some embodiments, W is selected from the group consisting of H, F, Cl, Br, and $C_{1-4}$ alkyl. In some embodiments, W is selected from the group consisting of H, F, Cl, Br, and $CH_3$. In some embodiments, W is selected from the group consisting of H, Cl, Br, and $CH_3$. In some embodiments, W is H. In some embodiments, W is halo. In some embodiments, W is Cl or Br. In some embodiments, W is $C_{1-4}$ alkyl. In some embodiments, W is $CH_3$.

In some embodiments, X is selected from the group consisting of H, halo, and $CH_3$. In some embodiments, X is selected from the group consisting of H, F, Cl, Br, and $C_{1-4}$ alkyl. In some embodiments, X is selected from the group consisting of H, F, Cl, Br, and $CH_3$. In some embodiments, X is H. In some embodiments, X is halo. In some embodiments, X is selected from the group consisting of F, Cl, and Br. In some embodiments, X is F. In some embodiments, X is $C_{1-4}$ alkyl. In some embodiments, X is $CH_3$.

In some embodiments, $R^1$ is selected from the group consisting of H, halo, OH, and $C_{1-4}$ haloalkyl. In some embodiments, $R^1$ is selected from the group consisting of H, halo, OH, and $CF_3$. In some embodiments, $R^1$ is selected from the group consisting of H, F, Cl, Br, OH, and $C_{1-4}$ haloalkyl. In some embodiments, $R^1$ is selected from the group consisting of H, F, Cl, Br, OH, and $CF_3$. In some embodiments, $R^1$ is selected from the group consisting of H, F, OH, and $CF_3$.

In some embodiments, $R^2$ is selected from the group consisting of H, F, Cl, and Br. In some embodiments, $R^2$ is selected from the group consisting of H, F, and Cl. In some embodiments, $R^2$ is selected from the group consisting of H and F. In some embodiments, $R^2$ is H. In some embodiments, $R^2$ is F.

In some embodiments, $R^3$ is H. In some embodiments, $R^3$ is halo. In some embodiments, $R^3$ is selected from the group consisting of F, Cl, and Br. In some embodiments, $R^3$ is Cl. In some embodiments, $R^3$ is selected from the group consisting of H and Cl.

In some embodiments, $R^4$ is selected from the group consisting of H, F, Cl, and Br. In some embodiments, $R^4$ is selected from the group consisting of H, F, and Cl. In some embodiments, $R^4$ is selected from the group consisting of H and F. In some embodiments, $R^4$ is H. In some embodiments, $R^4$ is F.

In some embodiments, $R^5$ is selected from the group consisting of H, halo, OH, and $C_{1-4}$ haloalkyl. In some embodiments, $R^5$ is selected from the group consisting of H, halo, OH, and $CF_3$. In some embodiments, $R^5$ is selected from the group consisting of H, F, Cl, Br, OH, and $C_{1-4}$ haloalkyl. In some embodiments, $R^5$ is selected from the group consisting of H, F, Cl, Br, OH, and $CF_3$. In some embodiments, $R^5$ is selected from the group consisting of H, F, OH, and $CF_3$. In some embodiments, $R^5$ is H. In some embodiments, $R^5$ is F. In some embodiments, $R^5$ is OH. In some embodiments, $R^5$ is $CF_3$.

In some embodiments, $R^4$ and $R^5$ are each H. In some embodiments, $R^4$ and $R^5$ come together, in combination with the carbon atoms to which they are attached, to form a $C_{3-6}$ carbocyclic group. In some embodiments, $R^4$ and $R^5$ come together, in combination with the carbon atoms to which they are attached, to form a $C_{3-6}$ carbocyclic group selected from:

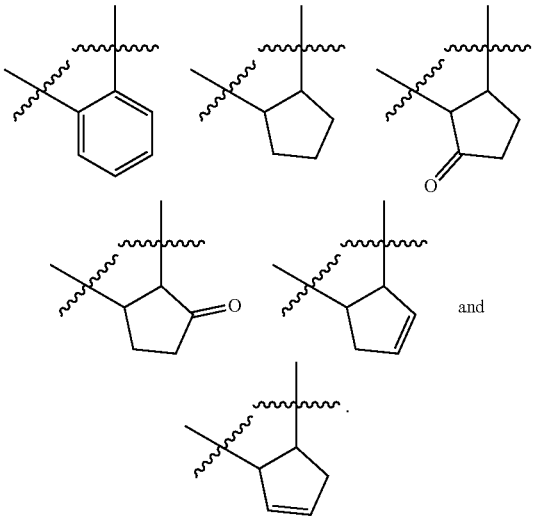

In some embodiments, $R^4$ and $R^5$ come together, in combination with the carbon atoms to which they are attached, to form a phenyl group.

In some embodiments, $R^4$ and $R^5$ come together, in combination with the carbon atoms to which they are attached, to form 3-6 membered heterocyclic group. In some embodiments, $R^4$ and $R^5$ come together, in combination with the carbon atoms to which they are attached, to form 5-6 membered heteroaryl group. In some embodiments, $R^4$ and $R^5$ come together, in combination with the carbon atoms to which they are attached, to form 3-6 membered heterocycloalkyl group. In some embodiments, $R^4$ and $R^5$ come together, in combination with the carbon atoms to which they are attached, to form 3-6 membered heterocyclic group selected from:

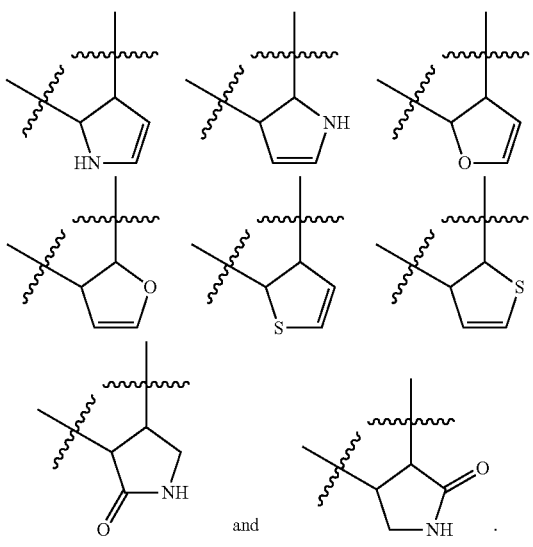

In some embodiments, $R^6$ is absent. In some embodiments, $R^6$ is selected from the group consisting of H and $C_{1-4}$ alkyl. In some embodiments, $R^6$ is selected from the group consisting of H and $CH_3$. In some embodiments, $R^6$ is H. In some embodiments, $R^6$ is $CH_3$.

In some embodiments:
$Y^1$ is N;
A is selected from the group consisting of N, NH, $N(CH_3)$, S, O, and $CH_2$;
L is selected from the group consisting of O, NH, S, and $CH_2$;
W and X are each independently selected from the group consisting of H, halo, and $CH_3$;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl; and
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group; and
$R^6$ is absent or $CH_3$.

In some embodiments:
$Y^1$ is N;
A is selected from the group consisting of N, NH, $N(CH_3)$, S, O, and $CH_2$;
L is selected from the group consisting of O, NH, S, and $CH_2$;
W is selected from the group consisting of H, Cl, Br, and $CH_3$;
X is selected from the group consisting of H, F, Cl, Br, and $CH_3$;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl; and
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group; and
$R^6$ is absent or $CH_3$.

In some embodiments:
$Y^1$ is N;
L is O;
A is NH;
W is selected from the group consisting of H, Cl, Br, and $CH_3$;
X is selected from the group consisting of H, F, Cl, Br, and $CH_3$;
$R^1$ and $R^5$ are each independently selected from the group consisting of H, halo, OH, $C_{1-4}$ alkyl, and $C_{1-4}$ haloalkyl;
$R^3$ is selected from the group consisting of H and Cl; and
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group; and
$R^6$ is absent.

In some embodiments:
$Y^1$ is N;
L is O;
A is NH;
W is selected from the group consisting of H, Cl, Br, and $CH_3$;
X is selected from the group consisting of H, F, Cl, Br, and $CH_3$;
$R^1$ is selected from the group consisting of H, halo, OH, $C_{1-4}$ alkyl, and $C_{1-4}$ haloalkyl;

$R^2$ is selected from the group consisting of H and halo;
$R^3$ is selected from the group consisting of H and Cl;
$R^4$ and $R^5$ are each H; and
$R^6$ is absent.

In some embodiments, the compound of Formula II is a compound of Formula IIa:

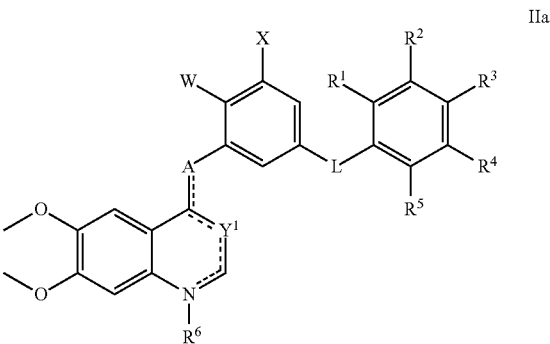

or a pharmaceutically acceptable salt thereof, wherein:
----- indicates a single or double bond;
$Y^1$ is N or CH;
$Y^2$ is selected from the group consisting of N, NH, and $N(C_{1-4}$ alkyl);
A is selected from the group consisting of N, NH, $N(C_{1-4}$ alkyl), S, O, and $C_{1-3}$ alkylene;
L is selected from the group consisting of O, NH, S, and $C_{1-3}$ alkylene;
W and X are each independently selected from the group consisting of H, halo, and $C_{1-4}$ alkyl;
$R^1$ and $R^5$ are each independently selected from the group consisting of H, halo, OH, $C_{1-4}$ alkyl, and $C_{1-4}$ haloalkyl;
$R^3$ is selected from the group consisting of H and halo; and
$R^2$ and $R^4$ are each independently selected from the group consisting of H and halo; or
alternatively, $R^4$ and $R^5$ come together, in combination with the carbon atoms to which they are attached, to form a $C_{3-6}$ carbocyclic group.

In some embodiments, the compound of Formula II is a compound of Formula IIb:

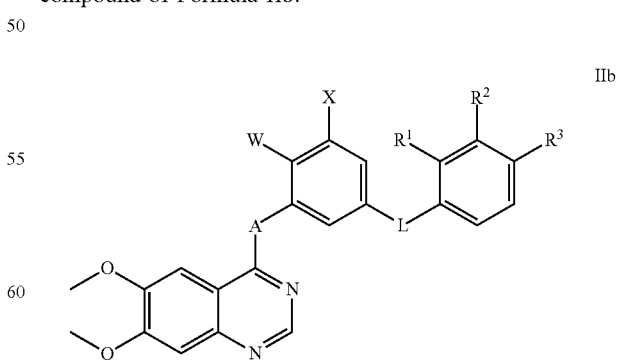

or a pharmaceutically acceptable salt thereof, wherein A, W, X, L, $R^1$, $R^2$, and $R^3$ are as defined above for compounds of Formula II.

In some embodiments, the compound of Formula II is a compound of Formula IIc:

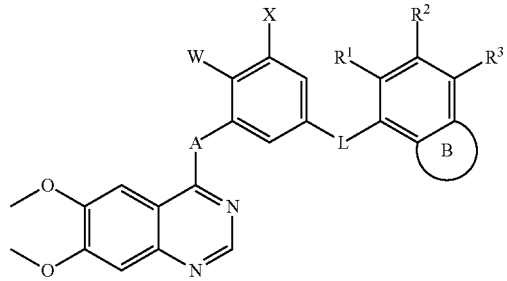

IIc or a pharmaceutically acceptable salt thereof, wherein B is a $C_{3-6}$ carbocyclic group or a 3-6 membered heterocyclic group, and A, W, X, L, $R^1$, $R^2$, and $R^3$ are as defined above for compounds of Formula II. In some embodiments, B is a $C_{3-6}$ carbocyclic group. In some embodiments, B is a 3-6 membered heterocyclic group.

In some embodiments, the compound of Formula II is a compound of Formula IId:

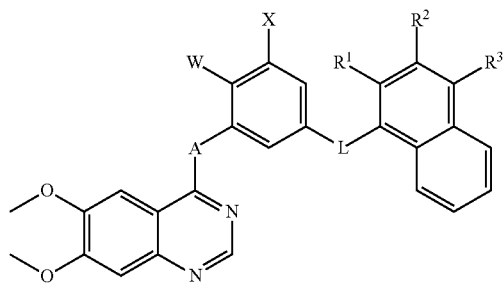

IId or a pharmaceutically acceptable salt thereof, wherein A, W, X, L, $R^1$, $R^2$, and $R^3$ are as defined above for compounds of Formula II.

In some embodiments, the compound of Formula II is selected from the group consisting of:

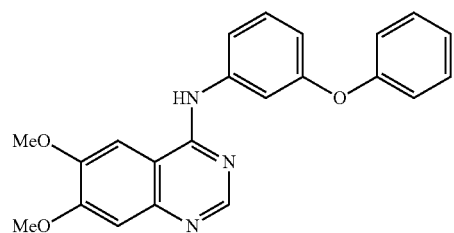

(4)

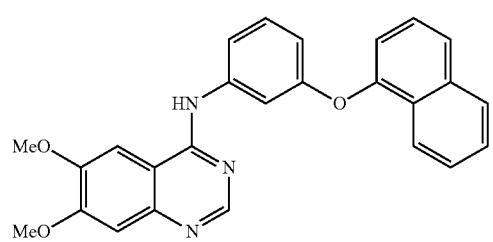

(13)

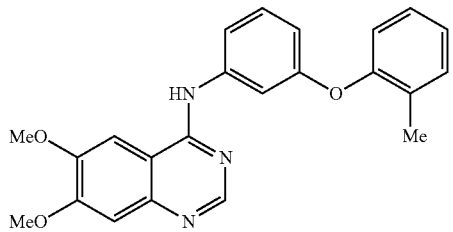

(14)

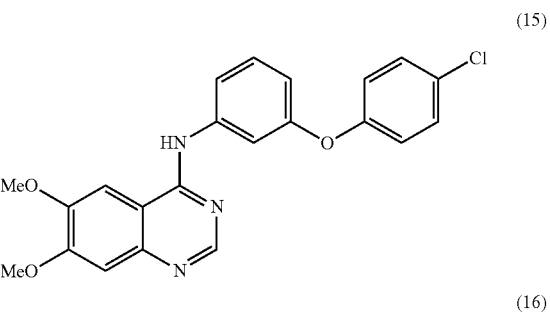

(15)

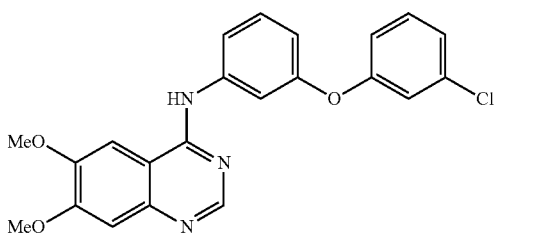

(16)

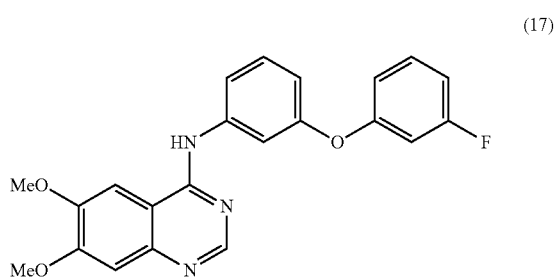

(17)

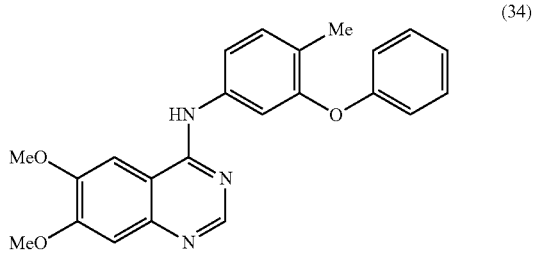

(34)

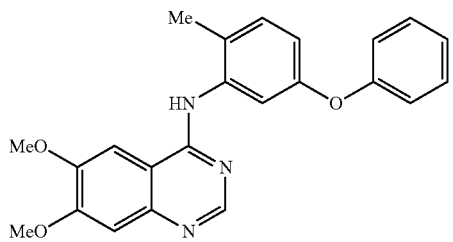

(35)

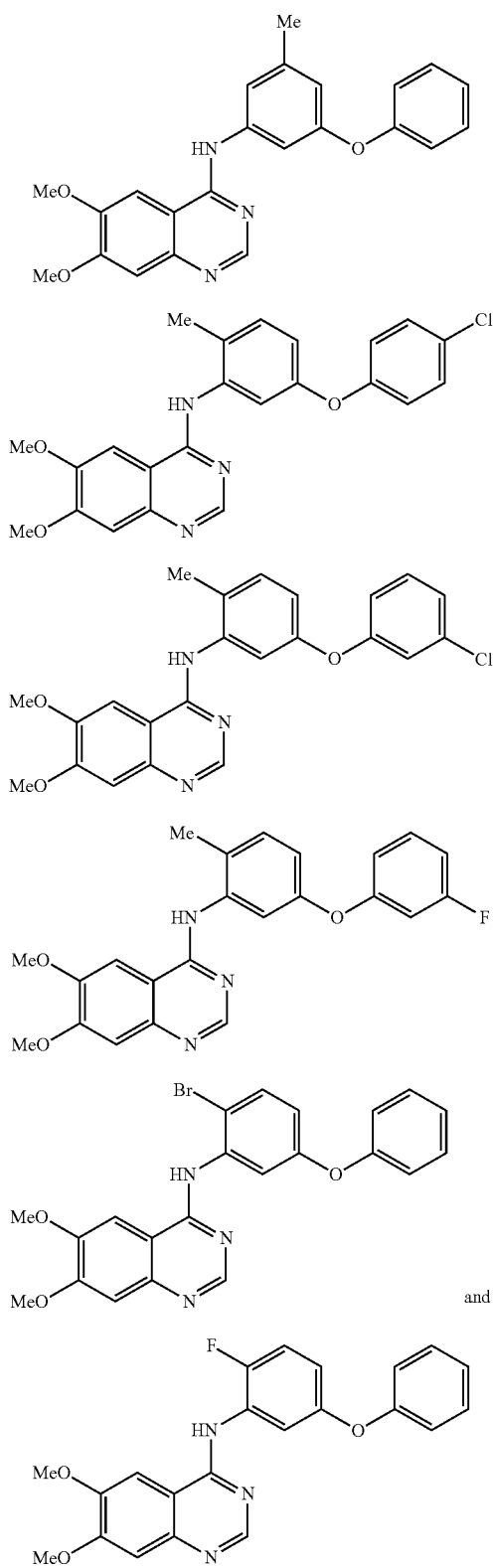

or a pharmaceutically acceptable salt thereof.

In some embodiments, the compound of Formula II is a pharmaceutically acceptable salt. In some embodiments, the compound of Formula II is a hydrochloride (i.e. HCl) salt. In some embodiments, the compound of Formula II is a 2,2,2-trifluoroacetic acid (i.e., TFA) salt.

The present application further provides a compound of Formula III:

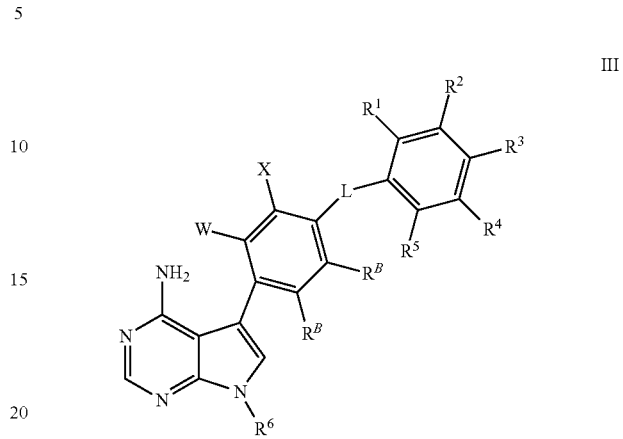

or a pharmaceutically acceptable salt thereof, wherein:

L is selected from the group consisting of O, NH, S, and $C_{1-3}$ alkylene;

W and X are each independently selected from the group consisting of H, halo, and $C_{1-4}$ alkyl;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and halo; and $R^6$ is selected from the group consisting of H, $C_{1-3}$ alkyl, $C_{3-6}$ cycloalkyl and 3-6 membered heterocycloalkyl.

In some embodiments, L is selected from the group consisting of O, NH, S, and $CH_2$. In some embodiments, L is O.

In some embodiments, W is selected from the group consisting of H, halo, and $CH_3$. In some embodiments, W is selected from the group consisting of H, F, Cl, Br, and $C_{1-4}$ alkyl. In some embodiments, W is selected from the group consisting of H, F, Cl, Br, and $CH_3$. In some embodiments, W is selected from the group consisting of H, Cl, Br, and $CH_3$. In some embodiments, W is H. In some embodiments, W is halo. In some embodiments, W is Cl or Br. In some embodiments, W is $C_{1-4}$ alkyl. In some embodiments, W is $CH_3$.

In some embodiments, X is selected from the group consisting of H, halo, and $CH_3$. In some embodiments, X is selected from the group consisting of H, F, Cl, Br, and $C_{1-4}$ alkyl. In some embodiments, X is selected from the group consisting of H, F, Cl, Br, and $CH_3$. In some embodiments, X is H. In some embodiments, X is halo. In some embodiments, X is selected from the group consisting of F, Cl, and Br. In some embodiments, X is F. In some embodiments, X is $C_{1-4}$ alkyl. In some embodiments, X is $CH_3$.

In some embodiments, each $R^B$ is H. In some embodiments, two $R^B$ groups come together, in combination with the carbon atoms to which they are attached, to form a $C_{3-6}$ carbocyclic group. In some embodiments, two $R^B$ groups come together, in combination with the carbon atoms to which they are attached, to form a phenyl group.

In some embodiments, $R^1$ is selected from the group consisting of H, halo, OH, and $C_{1-4}$ haloalkyl. In some embodiments, $R^1$ is selected from the group consisting of H, halo, OH, and $CF_3$. In some embodiments, $R^1$ is selected from the group consisting of H, F, Cl, Br, OH, and $C_{1-4}$ haloalkyl. In some embodiments, $R^1$ is selected from the group consisting of H, F, Cl, Br, OH, and $CF_3$. In some embodiments, $R^1$ is selected from the group consisting of H, F, OH, and $CF_3$.

In some embodiments, $R^2$ is selected from the group consisting of H, F, Cl, and Br. In some embodiments, $R^2$ is selected from the group consisting of H and F. In some embodiments, $R^2$ is H. In some embodiments, $R^2$ is F.

In some embodiments, $R^3$ is H. In some embodiments, $R^3$ is halo. In some embodiments, $R^3$ is selected from the group consisting of F, Cl, and Br. In some embodiments, $R^3$ is Cl. In some embodiments, $R^3$ is selected from the group consisting of H and Cl.

In some embodiments, $R^4$ is selected from the group consisting of H, F, Cl, and Br. In some embodiments, $R^4$ is selected from the group consisting of H and F. In some embodiments, $R^4$ is H. In some embodiments, $R^4$ is F.

In some embodiments, $R^5$ is selected from the group consisting of H, halo, OH, and $C_{1-4}$ haloalkyl. In some embodiments, $R^5$ is selected from the group consisting of H, halo, OH, and $CF_3$. In some embodiments, $R^5$ is selected from the group consisting of H, F, Cl, Br, OH, and $C_{1-4}$ haloalkyl. In some embodiments, $R^5$ is selected from the group consisting of H, F, Cl, Br, OH, and $CF_3$. In some embodiments, $R^5$ is selected from the group consisting of H, F, OH, and $CF_3$. In some embodiments, $R^5$ is H. In some embodiments, $R^5$ is F. In some embodiments, $R^5$ is OH. In some embodiments, $R^5$ is $CF_3$.

In some embodiments, $R^6$ is selected from the group consisting of H, $C_{1-3}$ alkyl, and $C_{3-6}$ cycloalkyl. In some embodiments, $R^6$ is selected from the group consisting of H, $C_{1-3}$ alkyl, and $C_{5-6}$ cycloalkyl. In some embodiments, $R^6$ is selected from the group consisting of H, $C_{1-3}$ alkyl, and cyclopentyl. In some embodiments, $R^6$ is selected from the group consisting of H, $CH_3$, and $C_{5-6}$ cycloalkyl. In some embodiments, $R^6$ is selected from the group consisting of H, $CH_3$, and cyclopentyl. In some embodiments, $R^6$ is selected from the group consisting of H, $C_{1-3}$ alkyl, and $C_{5-6}$ cycloalkyl and 5-6 membered heterocycloalkyl. In some embodiments, $R^6$ is selected from the group consisting of H, $CH_3$, cyclopentyl, 3-piperidinyl, 4-piperidinyl, and 3-pyrrolidinyl.

In some embodiments:

L is selected from the group consisting of O, NH, S, and $CH_2$;

W and X are each independently selected from the group consisting of H, halo, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and Cl; and $R^6$ is selected from the group consisting of H, $C_{1-3}$ alkyl, and $C_{3-6}$ cycloalkyl.

In some embodiments:

L is selected from the group consisting of O, NH, S, and $CH_2$;

W is selected from the group consisting of H, Cl, Br, and $CH_3$;

X is selected from the group consisting of H, F, Cl, Br, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and Cl; and $R^6$ is selected from the group consisting of H, $C_{1-3}$ alkyl, and $C_{5-6}$ cycloalkyl.

In some embodiments:

L is O;

W is selected from the group consisting of H, Cl, Br, and $CH_3$;

X is selected from the group consisting of H, F, Cl, Br, and $CH_3$;

each $R^B$ is H; or alternatively, two $R^B$ groups come together, in combination with the carbon atoms to which they are attached, to form a $C_{3-6}$ carbocyclic group;

$R^1$ and $R^5$ are each independently selected from the group consisting of H, halo, OH, $C_{1-4}$ alkyl, and $C_{1-4}$ haloalkyl;

$R^2$ and $R^4$ are each independently selected from the group consisting of H and halo;

$R^3$ is selected from the group consisting of H and Cl; and $R^6$ is selected from the group consisting of H, $CH_3$, and $C_{5-6}$ membered cycloalkyl.

In some embodiments, the compound of Formula III is a compound of Formula IIIc:

IIIa or a pharmaceutically acceptable salt thereof, wherein W, X, $R^1$, $R^2$, $R^3$, and $R^6$ are as defined above for compounds of Formula III.

In some embodiments, the compound of Formula III is a compound of Formula IIIb:

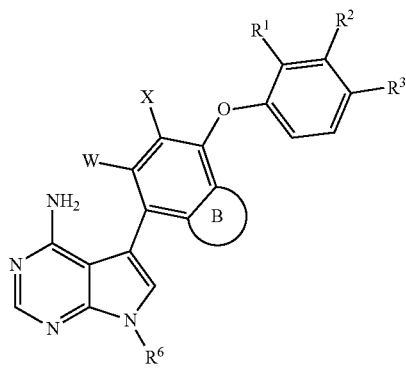

(IIIb)

or a pharmaceutically acceptable salt thereof, wherein B is a $C_{3-6}$ carbocyclic group or a 3-6 membered heterocyclic group, and W, X, $R^1$, $R^2$, $R^3$, and $R^6$ are as defined above for compounds of Formula III. In some embodiments, B is a $C_{3-6}$ carbocyclic group. In some embodiments, B is a 3-6 membered heterocyclic group.

In some embodiments, the compound of Formula III is a compound of Formula IIIc:

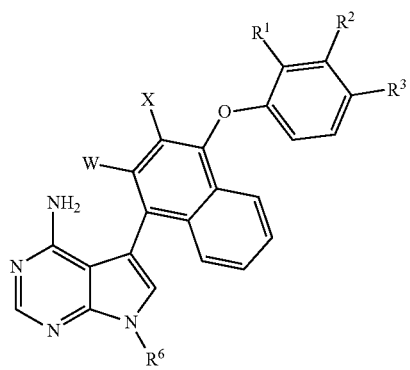

(IIIc)

or a pharmaceutically acceptable salt thereof, wherein W, X, $R^1$, $R^2$, $R^3$, and $R^6$ are as defined above for compounds of Formula III.

In some embodiments, the compound of Formula III is a pharmaceutically acceptable salt. In some embodiments, the compound of Formula III is a hydrochloride (i.e. HCl) salt. In some embodiments, the compound of Formula III is a 2,2,2-trifluoroacetic acid (i.e., TFA) salt.

In some embodiments, the compound of Formula III is selected from the group consisting of:

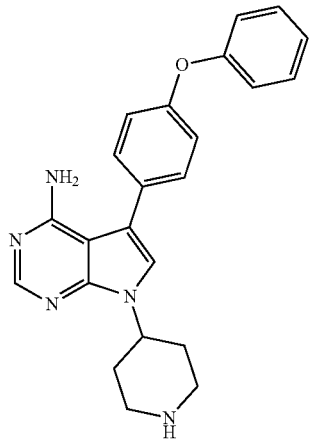

(91)

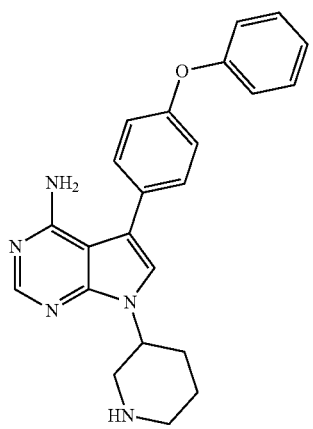

(92)

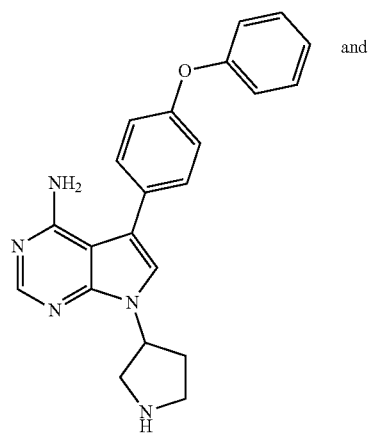

(93)

and (94)

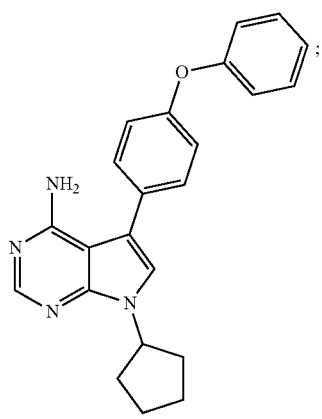

or a pharmaceutically acceptable salt thereof.

In some embodiments, the compound is 7-cyclopentyl-5-(4-phenoxyphenyl)-7H-pyrrolo[2,3-d]pyrimidin-4-amine (94), or a pharmaceutically acceptable salt thereof.

The present application further provides a pharmaceutical composition comprising a compound provided herein (e.g., a compound of Formula I, a compound of Formula II, a compound of Formula III, or a compound selected from group the consisting of compounds (1)-(114)) or a pharmaceutically acceptable salt thereof, and at least one pharmaceutically acceptable carrier.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

When employed as pharmaceuticals, the compounds provided herein can be administered in the form of pharmaceutical compositions; thus, the methods described herein can include administering pharmaceutical compositions provided herein. In some embodiments, the present application provides a pharmaceutical composition comprising a compound provided herein (e.g., a compound of Formula I, a compound of Formula II, a compound of Formula III or a compound selected from group the consisting of compounds (1)-(114)), or a pharmaceutically acceptable salt thereof and at least one pharmaceutically acceptable carrier.

These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable.

In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compounds can be effective over a wide dosage range and are generally administered in a therapeutically effective amount. It will be understood, however, that the amount of the compound actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

As will be appreciated, the compounds provided herein, including salts thereof, can be prepared using known organic synthesis techniques and can be synthesized according to any of numerous possible synthetic routes.

It will be appreciated by one skilled in the art that the processes described herein for preparing the compounds provided herein (e.g., compounds of Formula I, compounds of Formula II, compounds of Formula III), or a pharmaceutically acceptable salt thereof, are not the exclusive means by which compounds and salts provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances*

*in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency. For example, where one or more bonds are shown as optionally being a single or double bond (i.e., ═════ ), it is understood that the bonds comply with standard valency rules.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 4 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "carbocycle" refers to an aromatic (e.g., phenyl) or non-aromatic cyclic hydrocarbon including cyclized alkyl and/or alkenyl groups. Carbocycles include, for example, 3-6 ring forming carbon atoms (i.e., $C_{3-6}$ carbocycle), and can be mono- or polycyclic (e.g., having two or more fused rings). In some embodiments, the carbocycle is a $C_{5-6}$ carbocycle. Example carbocycles include, but are not limited to, cyclopropyl, cyclobutyl, cyclopentyl, cyclohexyl, and phenyl.

As used herein, "halo" refers to F, Cl, Br, or I. In some embodiments, a halo is F, Cl, or Br. In some embodiments, a halo is F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "heterocycle", employed alone or in combination with other terms, refers to a heteroaryl or heterocycloalkyl group having at least one heteroatom ring member selected from O, N, and S. In some embodiments, the heterocycle is a 3-6 membered heterocycle. In some embodiments, the heterocycle is a 5-6 membered heterocycle. In some embodiments, the heterocycle is a heteroaryl. In some embodiments, the heterocycle is a heterocycloalkyl.

As used herein, "heteroaryl" refers to an aromatic heterocycle having at least one heteroatom ring member selected from O, N, and S. In some embodiments, the heteroaryl ring has 1, 2, 3, or 4 heteroatom ring members independently selected from O, N, and S. In some embodiments, any ring-forming N in a heteroaryl moiety can be an N-oxide. In some embodiments, the heteroaryl has 4-6 ring atoms and 1, 2, 3 or 4 heteroatom ring members independently selected from O, N, and S. In some embodiments, the heteroaryl has 5-6 ring atoms and 1 or 2 heteroatom ring members independently selected from O, N, and S. In some embodiments, the heteroaryl is a five-membered or six-membered heteroaryl ring. Exemplary heteroaryl groups include, but are not limited to, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridyl, pyrazinyl, pyrimidinyl, triazinyl, and pyridazinyl.

As used herein, "heterocycloalkyl" refers to non-aromatic heterocycles having one or more ring-forming heteroatoms selected from O, N, and S. Example heterocycles include, but are not limited to, pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo (e.g., C(=O). The heterocycloalkyl group can be attached through a ring-forming carbon atom or a ring-forming heteroatom. In some embodiments, the heterocyclo alkyl is a 3-6 membered heterocycloalkyl having 1, 2, 3 or 4 heteroatom ring members independently selected from O, N, and S. In some embodiments, the heterocycloalkyl is a 5-6 membered heterocycloalkyl.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

Methods of Use and Combination Therapies

The present application further provides methods of treating a disease associated with KSR (e.g., upregulation of KSR expression) in a patient in need thereof. In some embodiments, the disease associated with KSR is a disease mediated by KSR. As used herein, the term "patient" refers to any animal, including mammals, for example, mice, rats, other rodents, rabbits, dogs, cats, swine, cattle, sheep, horses, primates, and humans. In some embodiments, the patient is a human. In some embodiments, the disease is selected from the group consisting of cancer, diabetes, obesity, a neurological disease, a skin disorder, an adverse effect associated with aging, a cardiovascular disease, organ transplant rejection, and graft versus host disease.

In some embodiments, the method comprises administering to a patient in need thereof a therapeutically effective amount of a compound provided herein (e.g., a compound of Formula I, a compound of Formula II, a compound of Formula III, or a compound selected from group the consisting of compounds (1)-(114)) or a pharmaceutically acceptable salt thereof. In some embodiments, the compound is a compound of Formula I, or a pharmaceutically acceptable salt thereof. In some embodiments, the compound is a compound of Formula II, or a pharmaceutically acceptable salt thereof. In some embodiments, the compound is a compound of Formula III, or a pharmaceutically acceptable salt thereof. In some embodiments, the compound is selected from the group consisting of compounds (1)-(114), or a pharmaceutically acceptable salt thereof. In some embodiments, the compound is 6,7-dimethoxy-N-(2-methyl-4-phenoxyphenyl)quinazolin-4-amine (21), or a pharmaceutically acceptable salt thereof. In some embodiments, the compound is 6,7-dimethoxy-N-(2-methyl-4-phenoxyphenyl)quinazolin-4-amine 2,2,2-trifluoroacetate (21.TFA). In some embodiments, the compound is 6,7-dimethoxy-N-(2-methyl-4-phenoxyphenyl)quinazolin-4-amine hydrochloride (21.HCl).

In some embodiments, the disease is cancer. In some embodiments, the cancer is selected from the group consisting of breast cancer, prostate cancer, esophageal cancer, colon cancer, endometrial cancer, brain cancer, bladder cancer, skin cancer, cancer of the uterus, cancer of the ovary, lung cancer, pancreatic cancer, renal cancer, prostate cancer, gastric cancer, stomach cancer, and hematological cancer. In some embodiments, the lung cancer is selected from the group consisting of non-small cell lung cancer, small cell lung cancer, and lung carcinoid tumor.

In some embodiments, the hematological cancer is selected from the group consisting of leukemia, lymphoma, and multiple myeloma.

In some embodiments, the hematological cancer is acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the leukemia is selected from the group consisting of acute lymphoblastic leukemia (ALL), chronic lymphocytic leukemia (CLL), acute myelogenous leukemia (AML), chronic myeloid leukemia (CML), hairy cell leukemia, T-cell prolymphocytic leukemia, juvenile myelomonocytic leukemia, and follicular lymphoma.

In some embodiments, the lymphoma is Hodgkin's lymphoma or non-Hodgkin's lymphoma (NHL).

In some embodiments, the non-Hodgkin lymphoma (NHL) is selected from relapsed NHL, refractory NHL, and recurrent follicular NHL.

In some embodiments, the disease is diabetes or obesity. In some embodiments, the disease is a neurological disease (e.g., a mood disorder, age onset proteotoxic disease (i.e., Alzheimer's disease). In some embodiments, the disease is a skin disorder (e.g., acne vulgaris). In some embodiments, the disease is an adverse effect associated with aging (e.g., cellular degradation associated with aging). In some embodiments, the disease is a cardiovascular disease (e.g., cardiac hypertrophy or cardiac disease). In some embodiments the disease is organ transplant rejection. In some embodiments, the disease is graft versus host disease.

In some embodiments, the method further comprises administering an additional therapeutic agent to the patient. Example additional therapeutic agents include, but are not limited to antibiotic agents, antiviral agents, antifungal agents, anesthetics (e.g., for use in combination with a surgical procedure), anti-inflammatory agents, anti-allergic agents, and chemotherapeutic agents. In some embodiments, the additional therapeutic agent comprises radiation therapy. In some embodiments, a compound provided herein is administered in combination with an additional therapeutic agent during a surgical procedure.

In some embodiments, the additional therapeutic agent is administered simultaneously with a compound provided herein. In some embodiments, the additional therapeutic agent is administered after administration of a compound provided herein. In some embodiments, the additional therapeutic agent is administered prior to administration of a compound provided herein.

In some embodiments, the additional therapeutic agent is selected from the group consisting of an antibiotic agent, antiviral agent, an antifungal agent, an anesthetic, or an anti-inflammatory agent (e.g., steroidal and non-steroidal anti-inflammatories), and an anti-allergic agent. Examples of suitable medicaments include, but are not limited to, coriticosteroids such as dexamethasone or prednisone, aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paromomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

In some embodiments, the additional therapeutic agent is a chemotherapeutic agent. In some embodiments, the additional therapeutic agent is a kinase inhibitor (e.g., KSR, MEK, Bcr-Abl, Flt-3, EGFR, HER2, JAK, c-MET, VEGFR, PDGFR, PI3K, cKit, IGF-1R, RAF, FAK, Akt mTOR, PIM, and AKT). For example, the additional therapeutic agent can be a MEK inhibitor or a KSR inhibitor. In some embodiments, the additional therapeutic agent is selected from the group consisting of a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib hydrochloride, antibodies to EGFR, imatinib mesylate, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, and idelalisib.

In some embodiments, the additional therapeutic agent is a MEK inhibitor. In some embodiments, the MEK inhibitor is a MEK1 and MEK2 inhibitor. In some embodiments, the MEK inhibitor is a MEK1 inhibitor. In some embodiments, the MEK inhibitor is a MEK2 inhibitor. In some embodiments, the MEK inhibitor is selected from the group consisting of trametinib, selumetinib, binimetinib, refametinib, pimasertib, cobimetinib, AZD8330, RO4987655, RO5126766, WX-554, E6201, MSC1936369B, PD-325901, CI-1040, RDEA119, CH5126766, GDC-0623, G-573, TAK-733, TAK-133, CI-1 040/PD1 84352, AZD6244, PD318088, PD98059, PD334581, RDEA1 19, 6-methoxy-7-(3-morpholin-4-yl-propoxy)-4-(4-phenoxy-phenylamino)quinoline-3-carbonitrile, and 4-[3-Chloro-4-(1-methyl-1H-imidazol-2-ylsulfanyl)phenylamino]-6-methoxy-7-(3-morpholin-4-yl-propoxy)-quinoline-3-carbonitrile, and PD035901.

The present application further provides a method of treating a disease provided herein (e.g., cancer, diabetes, obesity, an adverse effect associated with aging, a neurological disease, a skin disorder, a cardiovascular disease, organ transplant rejection, and graft versus host disease) in a patient in need thereof, comprising administering to the patient a therapeutically effective amount of a compound provided herein (e.g., a compound of Formula I, a compound of Formula II, a compound of Formula III, or a compound selected from group the consisting of compounds (1)-(114)) or a pharmaceutically acceptable salt thereof, and an additional therapeutic agent provided herein. In some embodiments, the compound is 6,7-dimethoxy-N-(2-methyl-4-phenoxyphenyl)quinazolin-4-amine (21), or a pharmaceutically acceptable salt thereof. In some embodiments, the compound is 6,7-dimethoxy-N-(2-methyl-4-phenoxyphenyl)quinazolin-4-amine 2,2,2-trifluoroacetate (21.TFA). In some embodiments, the compound is 6,7-dimethoxy-N-(2-methyl-4-phenoxyphenyl)quinazolin-4-amine hydrochloride (21.HCl). In some embodiments, the disease is cancer. In some embodiments, the disease is diabetes or obesity. In some embodiments, the disease is an adverse effect associated with aging (e.g., cellular degradation associated with aging). In some embodiments, the disease is a neurological disease (e.g., a mood disorder, age onset proteotoxic disease (i.e., Alzheimer's disease). In some embodiments, the disease is a skin disorder (e.g., acne vulgaris). In some embodiments, the disease is a cardiovascular disease (e.g., cardiac hypertrophy or cardiac disease). In some embodiments the disease is organ transplant rejection. In some embodiments, the disease is graft versus host disease.

In some embodiments, the additional therapeutic agent is a MEK inhibitor. In some embodiments, the MEK inhibitor is a MEK1 and MEK2 inhibitor. In some embodiments, the MEK inhibitor is a MEK1 inhibitor. In some embodiments, the MEK inhibitor is a MEK2 inhibitor. In some embodiments, the MEK inhibitor is selected from the group consisting of trametinib, selumetinib, binimetinib, refametinib, pimasertib, cobimetinib, AZD8330, RO4987655, RO5126766, WX-554, E6201, MSC1936369B, PD-325901, CI-1040, RDEA119, CH5126766, GDC-0623, G-573, TAK-733, TAK-133, CI-1 040/PD1 84352, AZD6244, PD318088, PD98059, PD334581, RDEA1 19, 6-methoxy-7-(3-morpholin-4-yl-propoxy)-4-(4-phenoxy-phenylamino)quinoline-3-carbonitrile, and 4-[3-Chloro-4-(1-methyl-1H-imidazol-2-ylsulfanyl)phenylamino]-6-methoxy-7-(3-morpholin-4-yl-propoxy)-quinoline-3-carbonitrile, and PD035901.

The present application further provides a method of treating a disease provided herein (e.g., cancer, diabetes, obesity, adverse effect associated with aging, a neurological disease, a skin disorder, a cardiovascular disease, organ transplant rejection, and graft versus host disease) in a patient in need thereof, comprising:
  (i) determining if the disease is associated with a KSR (e.g., mediated by a KSR); and
  (ii) if the disease is determined to be associated with a KSR, administering to the patient a therapeutically effective amount of a compound provided herein (e.g., a compound of Formula I, a compound of Formula II, a compound of Formula III, or a compound selected from group the consisting of compounds (1)-(114)) or a pharmaceutically acceptable salt thereof. In some embodiments, the compound is 6,7-dimethoxy-N-(2-methyl-4-phenoxyphenyl)quinazolin-4-amine (21), or a pharmaceutically acceptable salt thereof. In some embodiments, the compound is 6,7-dimethoxy-N-(2-methyl-4-phenoxyphenyl)quinazolin-4-amine 2,2,2-trifluoroacetate (21.TFA). In some embodiments, the compound is 6,7-dimethoxy-N-(2-methyl-4-phenoxyphenyl)quinazolin-4-amine hydrochloride (21.HCl).

In some embodiments, the disease associated with KSR is a disease mediated by KSR. In some embodiments, the disease is associated with KSR1 and KSR2. In some embodiments, the disease is associated with KSR1 or KSR2. In some embodiments, the disease is associated with KSR1. In some embodiments, the disease is associated with KSR2. In some embodiments, the disease is mediated by KSR1 and KSR2. In some embodiments, the disease is mediated by KSR1 or KSR2. In some embodiments, the disease is mediated by KSR1. In some embodiments, the disease is mediated by KSR2.

In some embodiments, the disease is cancer. In some embodiments, the disease is diabetes or obesity. In some embodiments, the disease is an adverse effect associated with aging (e.g., cellular degradation associated with aging). In some embodiments, the disease is a neurological disease (e.g., a mood disorder, age onset proteotoxic disease (i.e., Alzheimer's disease). In some embodiments, the disease is a skin disorder (e.g., acne vulgaris). In some embodiments, the disease is a cardiovascular disease (e.g., cardiac hypertrophy or cardiac disease). In some embodiments the disease is organ transplant rejection. In some embodiments, the disease is graft versus host disease.

In some embodiment, the KSR comprises KSR1. In some embodiments, the KSR comprises KSR2. In some embodiments, the KSR comprises KSR1 and KSR2. In some embodiments, the KSR is KSR1. In some embodiments, the KSR is KSR2.

In some embodiments, the method further comprises administering an additional therapeutic agent provided herein. In some embodiments, the additional therapeutic agent is a chemotherapeutic agent.

In some embodiments, the additional therapeutic agent is a MEK inhibitor. In some embodiments, the MEK inhibitor is a MEK1 and MEK2 inhibitor. In some embodiments, the MEK inhibitor is a MEK1 inhibitor. In some embodiments, the MEK inhibitor is a MEK2 inhibitor. In some embodiments, the MEK inhibitor is selected from the group consisting of trametinib, selumetinib, binimetinib, refametinib, pimasertib, cobimetinib, AZD8330, RO4987655, RO5126766, WX-554, E6201, MSC1936369B, PD-325901, CI-1040, RDEA119, CH5126766, GDC-0623, G-573, TAK-733, TAK-133, CI-1 040/PD1 84352, AZD6244, PD318088, PD98059, PD334581, RDEA1 19, 6-methoxy-7-(3-morpholin-4-yl-propoxy)-4-(4-phenoxy-phenylamino)quinoline-3-carbonitrile, and 4-[3-Chloro-4-(1-methyl-1H-imidazol-2-ylsulfanyl)phenylamino]-6-methoxy-7-(3-morpholin-4-yl-propoxy)-quinoline-3-carbonitrile, and PD035901.

The present application further provides a method of inhibiting KSR in a cell, comprising contacting the KSR with a compound provided herein (e.g., a compound of Formula I, a compound of Formula II, a compound of Formula III, or a compound selected from group the consisting of compounds (1)-(114)) or a pharmaceutically acceptable salt thereof. In some embodiments, the compound is 6,7-dimethoxy-N-(2-methyl-4-phenoxyphenyl)quinazolin-4-amine (21), or a pharmaceutically acceptable salt thereof. In some embodiments, the compound is 6,7-dimethoxy-N-(2-methyl-4-phenoxyphenyl)quinazolin-4-amine 2,2,2-trifluoroacetate (21.TFA). In some embodiments, the compound is 6,7-dimethoxy-N-(2-methyl-4-phenoxyphenyl)quinazolin-4-amine hydrochloride (21.HCl).

In some embodiments, the KSR comprises KSR1. In some embodiments, the KSR comprises KSR2. In some embodiments, the KSR comprises KSR1 and KSR2. In some embodiments, the KSR is KSR1. In some embodiments, the KSR is KSR2.

The present application further provides a method of inhibiting a KSR and a MEK in a cell, comprising contacting the cell with a compound provided herein (e.g., a compound of Formula I, a compound of Formula II, a compound of Formula III, or a compound selected from group the consisting of compounds (1)-(114)) or a pharmaceutically acceptable salt thereof. In some embodiments, the compound is 6,7-dimethoxy-N-(2-methyl-4-phenoxyphenyl) quinazolin-4-amine (21), or a pharmaceutically acceptable salt thereof. In some embodiments, the compound is 6,7-dimethoxy-N-(2-methyl-4-phenoxyphenyl)quinazolin-4-amine 2,2,2-trifluoroacetate (21.TFA). In some embodiments, the compound is 6,7-dimethoxy-N-(2-methyl-4-phenoxyphenyl)quinazolin-4-amine hydrochloride (21.HCl).

In some embodiment, the KSR comprises KSR1. In some embodiments, the KSR comprises KSR2. In some embodiments, the KSR comprises KSR1 and KSR2. In some embodiments, the KSR is KSR1. In some embodiments, the KSR is KSR2. In some embodiments, the MEK comprises MEK1. In some embodiments, the MEK comprises MEK2. In some embodiments, the MEK comprises MEK1 and MEK2. In some embodiments, the MEK is MEK1. In some embodiments, the MEK is MEK2.

In some embodiments, the method further comprises contacting the cell with a MEK inhibitor. In some embodiments, the MEK inhibitor is a MEK1 and MEK2 inhibitor. In some embodiments, the MEK inhibitor is a MEK1 inhibitor. In some embodiments, the MEK inhibitor is a MEK2 inhibitor. In some embodiments, the MEK inhibitor is selected from the group consisting of trametinib, selumetinib, binimetinib, refametinib, pimasertib, cobimetinib, AZD8330, RO4987655, RO5126766, WX-554, E6201, MSC1936369B, PD-325901, CI-1040, RDEA119, CH5126766, GDC-0623, G-573, TAK-733, TAK-133, CI-1 040/PD1 84352, AZD6244, PD318088, PD98059, PD334581, RDEA1 19, 6-methoxy-7-(3-morpholin-4-yl-propoxy)-4-(4-phenoxy-phenylamino)quinoline-3-carbonitrile, and 4-[3-Chloro-4-(1-methyl-1H-imidazol-2-ylsulfanyl)phenylamino]-6-methoxy-7-(3-morpholin-4-yl-propoxy)-quinoline-3-carbonitrile, and PD035901.

The phrase "pharmaceutically acceptable amount" or "therapeutically effective amount" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. For example, a "pharmaceutically acceptable amount" or "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Materials and Methods

All solvents were purchased from Sigma-Aldrich and were used as received; anhydrous solvents were used for reactions, and HPLC grade solvents were used for aqueous work ups, recrystallizations and chromatography. The palladium metal on solid support, used in hydrogenation reactions, was purchased from Sigma-Aldrich as 10% w/w on activated carbon (dry basis), with 50% w/w water added (Degussa type); designated in procedures as "5% w/w on activated carbon". Other reagents were purchased from various vendors and were used as received. Reactions were run as described in the individual procedures using standard double manifold and syringe techniques. Glassware was dried by baking in an oven at 130° C. for ≥12 h prior to use, or flame-dried. The pH of aqueous solutions was estimated using pH paper. Vacuum filtrations were carried out using a house vacuum line (~100 torr). In the individual procedures, the phrases "concentrated under vacuum" and "concentrated to dryness" mean that solvent was removed on a rotary evaporator using a diaphragm pump (with an automatic vacuum regulator) and then remaining traces of volatiles were removed on a high-vacuum (<1 torr) oil pump. Unless specified otherwise, the term "flask" refers to the round-bottomed variety.

Reactions were monitored by TLC using EMD silica gel 60 $F_{254}$ (250 μm) glass-backed plates (visualized by UV fluorescence quenching and stained with basic $KMnO_4$ solution) and by liquid chromatography-tandem mass spectrometry (LC-MS). Analysis by reverse-phase LC-MS was carried out on a Waters Aquity I-Class UPLC system, with a C18 column (2.1×30 mm, 1.7 μm particle size), heated at 50° C., eluting at 0.6 mL/min, using a 3 min linear gradient method with a mobile phase consisting of water/acetonitrile (0.1% v/v formic acid added to each): 95:5→1:99 (0-2.5 min), 1:99 (2.5-3 min). Sample runs were monitored using alternating positive/negative electrospray ionization (50-1000 amu) and UV detection at 254 nm. Dimensions of "plugs", "pads" and "columns" for filtration or flash chromatography are reported as: ((diameter×length) cm). The 5¾ inch pipets (4 mL) used for filtration and micro scale flash chromatography were purchased from Fisher Scientific (product number 22-378-893). Automated preparative normal- and reverse-phase chromatography was carried out on an Interchim PuriFlash 450 purification system with a diode array detector (runs were monitored at 220-400 nm) Prepacked silica gel cartridges (12, 25 and 40 g) were employed for normal-phase chromatography, eluting at 20-30 mL/min. For reverse-phase chromatography a C18 column (30×150 mm, 5 μm particle size) was used, eluting at 15-20 mL/min with a pressure limit of 50 bar. $^1$H NMR spectra were recorded at 400 MHz on a Bruker spectrometer and are reported in ppm using the residual solvent signal (dimethylsulfoxide-$d_6$=2.50 ppm) as an internal standard. Data are reported as: {(δ shift), [(s=singlet, d=doublet, dd=doublet of doublets, br=broad, m=multiplet), (J=coupling constant in Hz) and (integration)]}. Proton-decoupled $^{13}$C NMR spectra were recorded at 100 MHz on a Bruker spectrometer and are reported in ppm using the residual solvent signal (dimethylsulfoxide-$d_6$=39.5 ppm) as an internal standard.

A375, HCT-116, and A549 cells were obtained from the American Type Culture Collection. SK-MEL-239 and 293H cells were graciously provided by the Poulikakos Lab at the Icahn School of Medicine at Mount Sinai. Cell lines were maintained in Dulbecco's modified Eagle's medium with 10% fetal bovine serum supplement with penicillin/streptomycin.

Antibodies for detection of KSR1 (Product number: 4640), Flag-tag (Product number: 8146), GFP (Product number: 2555), pMEK (Product number: 9121), pERK (Product number: 9101), and MEK (Product number: 9122) were obtained from Cell Signaling. Western blotting was performed as described herein. For primary antibody detection, blots were washed several times and probed for 1 hr with anti-Mouse-HRP or anti-Rabbit-HRP (Cell Signaling) in 5% milk TBST.

KSR1-FLAG (Addgene ID:25970) and MEK1-GFP (Addgene ID:14746) plasmids were obtained from Addgene. The plasmids for expression of RAF was generated by DNA 2.0. Constructs harboring mutations were generated by site-directed mutagenesis (Agilent). DNA and siRNA transfections were carried out using Fugene 6 (Promega) and Dharmafect (GE Dharmacon) reagents in accordance with the manufacturer's recommendations.

Trametinib and dabrafenib were obtained from Selleck Chemicals. All compounds were dissolved in DMSO and subsequently diluted for biochemical and cellular experiments.

Example 1. 6,7-Dimethoxy-N-(4-phenoxyphenyl)quinazolin-4-amine hydrochloride (APS-1-68-2) (2.HCl)

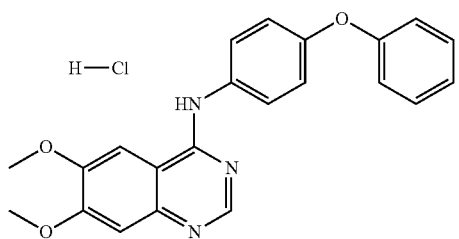 [SMILES: COc1cc2ncnc(Nc3ccc(Oc4ccccc4)cc3)c2cc1OC ; Cl]

An 8 mL vial (with screwcap) was charged with 4-chloro-6,7-dimethoxyquinazoline (56.2 mg, 0.250 mmol), 4-phenoxyaniline (55.6 mg, 0.300 mmol) and 2-propanol (5 mL). The vial was sealed and the mixture was heated at 70-75° C. with stirring for 12 h. After the reaction mixture had cooled to room temperature, the precipitate was collected by vacuum filtration and the solid was washed with 2-propanol and hexanes. Air-drying yielded 101 mg (99%) of the title compound as a light-yellow solid. $^1$H NMR (400 MHz, DMSO-$d_6$) δ 14.91 (br s, 1H), 11.50 (br s, 1H), 8.80 (s, 1H), 8.37 (s, 1H), 7.70 (d, J=8.9 Hz; 2H), 7.46-7.39 (m, 2H), 7.37 (s, 1H), 7.20-7.15 (m, 1H), 7.11 (d, J=8.9 Hz; 2H), 7.09-7.04 (m, 2H), 4.02 (s, 3H), 3.99 (s, 3H); $^{13}$C NMR (100 MHz, DMSO-$d_6$) δ 158.1, 156.6, 156.2, 154.7, 150.1, 148.7, 135.5, 132.2, 130.1, 126.6, 123.7, 118.7, 118.6, 107.2, 104.1, 99.8, 57.0, 56.4; LC-MS (ESI+) m/z: [M+H]$^+$ Calcd for $C_{22}H_{20}N_3O_3$ 374.2; Found 374.3.

Example 2. 4-(6,7-Dimethoxyquinazoline-4-ylamino)-3-methylphenol hydrochloride (APS-2-77) (19.HCl)

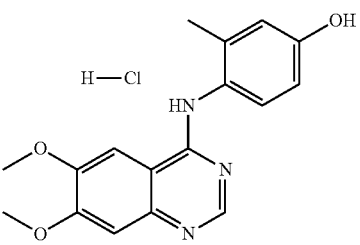 [SMILES: COc1cc2ncnc(Nc3ccc(O)cc3C)c2cc1OC ; Cl]

A 20 mL vial (with screwcap) was charged with 4-chloro-6,7-dimethoxyquinazoline (112 mg, 0.500 mmol), 4-amino-3-methylphenol (67.7 mg, 0.550 mmol) and 2-propanol (6 mL). The vial was sealed and the mixture was heated at 70-75° C. with stirring for 22 h. After the reaction mixture had cooled to room temperature, the precipitate was collected by vacuum filtration and the solid was washed with 2-propanol, EtOAc and hexanes. Air-drying yielded 151 mg (87%) of the title compound as a light-brown solid: $^1$H NMR (400 MHz, DMSO-$d_6$) δ 11.22 (br s, 1H), 9.63 (br s, 1H), 8.67 (s, 1H), 8.29 (s, 1H), 7.38 (s, 1H), 7.10 (d, J=8.6 Hz; 1H) 6.76 (d, J=2.5 Hz; 1H), 6.70 (dd, J=2.6, 8.4 Hz; 1H), 3.984 (s, 3H), 3.978 (s, 3H), 2.10 (s, 3H) ppm; $^{13}$C NMR (100 MHz, DMSO-$d_6$) δ 159.2, 156.8, 156.1, 150.1, 148.7, 136.1, 135.1, 128.5, 126.4, 117.0, 113.2, 106.7, 104.0, 99.7, 56.8, 56.4, 18.0 ppm; LC-MS (ESI+) m/z: [M+H]$^+$ Calcd for $C_{17}H_{18}N_3O_3$ 312.3, Found 312.1.

Example 3. 6,7-Dimethoxy-N-(2-methyl-4-phenoxyphenyl)quinazolin-4-amine 2,2,2-trifluoroacetate (APS-2-79) (21.TFA)

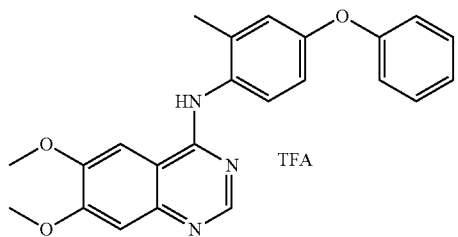 [SMILES: COc1cc2ncnc(Nc3ccc(Oc4ccccc4)cc3C)c2cc1OC ; "TFA"]

An oven-dried 8 mL vial (with sepcap), under nitrogen, was charged with copper(I) iodide (3.2 mg, 0.017 mmol, 10 mol %), picolinic acid (4.2 mg, 0.034 mmol, 20 mol %), $K_3PO_4$ (108 mg, 0.509 mmol) and dry DMSO (1 mL). After the mixture had stirred for 20 min, 4-(6,7-dimethoxyquinazoline-4-ylamino)-3-methylphenol hydrochloride (59.2 mg, 0.170 mmol) and iodobenzene (20.0 μL, 0.179 mmol) were added. The initially deep-red mixture was heated at 90° C. with stirring for 20 h. The resulting brown mixture was allowed to cool to room temperature and then filtered through neutral alumina eluting with $CH_2Cl_2$/MeOH (95:5, ca. 20 mL). The filtrate was concentrated to leave a yellow-brown semi-solid, which was purified by reverse phase chromatography using a linear gradient consisting of water (with 0.1% v/v TFA)/acetonitrile 90:10→95:5. The appropriate fractions were concentrated to yield 46.0 mg (56%) of the title compound as a yellow solid: ¹H NMR (400 MHz, DMSO-d₆) δ 11.01 (br s, 1H), 8.75 (s, 1H), 8.06 (s, 1H), 7.48-7.40 (m, 2H), 7.38-7.31 (m, 2H), 7.23-7.15 (m, 1H), 7.11-7.03 (m, 3H), 6.95 (dd, J=2.7, 8.6 Hz; 1H) 4.00 (s, 3H), 3.98 (s, 3H), 2.18 (s, 1H) ppm; ¹³C NMR (100 MHz, DMSO-d₆) δ 159.2, 158.3, 157.9, 156.3, 156.0, 150.2, 149.2, 137.2, 135.6, 130.5, 130.2, 129.2, 123.8, 120.2, 118.9, 116.3, 106.7, 103.3, 100.1, 56.5, 17.8 ppm; LC-MS (ESI+) m/z: [M+H]⁺ Calcd for C₂₃H₂₂N₃O₃ 388.4, Found 388.2.

Example 4. 6,7-Dimethoxy-N-(4-phenoxyphenyl)quinazolin-4-amine (2)

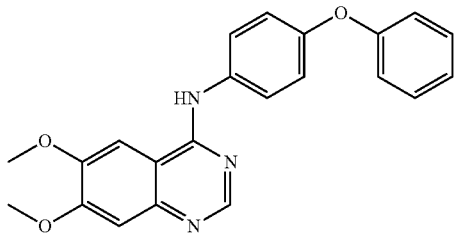 [SMILES: COc1cc2ncnc(Nc3ccc(Oc4ccccc4)cc3)c2cc1OC]

The hydrochloride salt of Example 1 (i.e., compound 2.HCl) was suspended in a mixture of water and 95:5 CH₂Cl₂/MeOH, and then the pH of the aqueous phase was adjusted to 7-8 with a saturated solution of NaHCO₃. The mixture was transferred to a separatory funnel, the layers were separated and the aqueous phase was extracted with a 95:5 mixture of CH₂Cl₂/MeOH (×2). The organic extracts were pooled, dried (Na₂SO₄), filtered and concentrated to dryness: ¹H NMR (400 MHz, DMSO-d₆) δ 9.49 (br s, 1H), 8.44 (s, 1H), 7.84 (s, 1H), 7.78 (d, J=9.0 Hz; 2H), 7.43-7.36 (m, 2H), 7.18 (s, 1H), 7.15-7.10 (m, 1H), 7.08 (d, J=9.0 Hz; 1H), 7.05-7.00 (m, 2H), 3.96 (s, 3H), 3.93 (s, 3H).

Example 5. 6,7-Dimethoxy-N-(4-methoxyphenyl)quinazolin-4-amine hydrochloride (APS-1-70-1) (3.HCl)

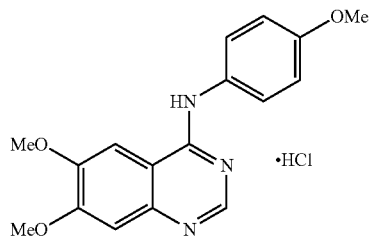 [SMILES: COc1ccc(Nc2ncnc3cc(OC)c(OC)cc23)cc1 ; Cl]

An 8 mL vial was charged with 4-chloro-6,7-dimethoxyquinazoline (56.2 mg, 0.250 mmol), 4-methoxyaniline (33.9 mg, 0.275 mmol) and 2-PrOH (2.5 mL). The mixture was stirred and heated at 70° C. for 14 h. After the reaction mixture had cooled to room temperature the solid was collected by vacuum filtration through a pipet filter (balled up piece of a Kimwipe in a 4 mL pipet) and then washed with 2-PrOH (×1) and hexanes (×2). Air-drying yielded 40.0 mg (46%) of the title compound as a pale-yellow solid: ¹H NMR (400 MHz, DMSO-d₆) δ 11.21 (br s, 1H), 8.73 (s, 1H), 8.26 (s, 1H), 7.58 (d, J=9.2 Hz; 2H), 7.33 (s, 1H), 7.04 (d, J=9.2 Hz; 2H), 4.00 (s, 3H), 3.98 (s, 3H), 3.80 (s, 3H); ¹³C NMR (100 MHz, DMSO-d₆) δ 158.0, 157.5, 156.0, 150.0, 149.0, 136.0, 129.7, 126.2, 113.9, 107.2, 103.8, 100.2, 56.8, 56.4, 55.4; LC-MS (ESI+) m/z: [M+H]⁺ Calcd for C₁₇H₁₈N₃O₃ 312.1; Found 312.3.

Example 6. 4-((6,7-Dimethoxyquinazolin-4-yl)amino)phenol hydrochloride (APS-1-82-1) (7.HCl)

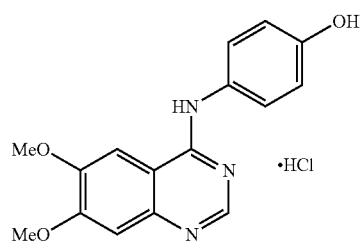 [SMILES: COc1cc2ncnc(Nc3ccc(O)cc3)c2cc1OC ; Cl]

A 20 mL vial was charged with 4-chloro-6,7-dimethoxyquinazoline (225 mg, 1.00 mmol), 4-aminophenol (120 mg, 1.10 mmol) and 2-PrOH (5 mL). The mixture was stirred rapidly and heated at 70° C. for 7 h. After the reaction mixture had cooled to room temperature the solid was collected by vacuum filtration and washed with hexanes (×2). Air-drying yielded 293 mg (88%) of the title compound as a yellow solid: ¹H NMR (400 MHz, DMSO-d₆) δ 14.83 (br s, 1H), 11.28 (br s, 1H), 9.70 (br s, 1H), 8.73 (s, 1H), 8.28 (s, 1H), 7.43 (d, J=9.0 Hz; 2H), 7.35 (s, 1H), 6.86 (d, J=9.0 Hz; 2H), 3.99 (s, 3H), 3.97 (s, 3H); ¹³C NMR (100 MHz, DMSO-d₆) δ 158.0, 156.0, 150.0, 148.6, 135.1, 127.9, 126.4, 115.2, 107.0, 104.0, 99.72, 99.70, 56.9, 56.4; LC-MS (ESI+) m/z: [M+H]⁺ Calcd for C₁₆H₁₆N₃O₃ 298.1; Found 298.3.

Example 7. N-(4-(Benzyloxy)phenyl)-6,7-dimethoxyquinazolin-4-amine 2,2,2-trifluoroacetate (APS-2-12) (10.TFA)

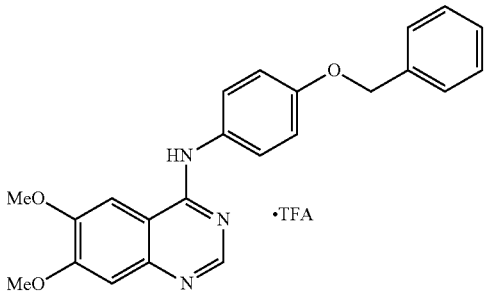 [SMILES: COc1cc2ncnc(Nc3ccc(OCc4ccccc4)cc3)c2cc1OC ; "·TFA"]

An 8 mL vial was charged with Compound 7 (see Example 6) (100 mg, 0.300 mmol), K₂CO₃ (92 mg, 0.67 mmol) and dry DMF (2 mL). To the stirred mixture was added benzyl bromide (44 µL, 0.37 mmol) dropwise (<1 min) via syringe. The reaction was blanketed with argon and the vial was sealed with a screw cap. The mixture was heated at 60° C. and stirred for 16 h. The resulting solution was allowed to cool to room temperature, then water (6 mL) was added and stirring was continued for 5 min. The precipitate that formed was isolated by vacuum filtration and washed with water (1 mL). The collected yellow solid was purified by silica gel chromatography (25 g cartridge), eluting at 20 mL/min and using a linear gradient of CH₂Cl₂/MeOH: 100:0→80:20 over 20 column volumes. The appropriate fractions were pooled and concentrated under vacuum to yield 92 mg (79%) of the freebase of Compound 10, as a white solid. The TFA salt was synthesized for direct comparison with a commercial sample: The freebase was stirred for 15 min in a mixture of MeOH and TFA (1.05 equiv) and then the solution was concentrated to dryness. The remaining residue was triturated with Et₂O, and the resulting precipitate was collected by vacuum filtration. The isolated solid was washed with Et₂O (×1) and hexanes (×1), and then air-dried. Further drying under high vacuum provided the title compound as a yellow solid: ¹H NMR (400 MHz, DMSO-d₆) δ 10.90 (br s, 1H), 8.74 (s, 1H), 8.03 (s, 1H), 7.54 (d, J=9.0 Hz; 2H), 7.50-7.45 (m, 2H), 7.44-7.38 (m, 2H), 7.38-7.32 (m, 1H), 7.30 (s, 1H), 7.13 (d, J=9.0 Hz; 1H), 5.16 (s, 2H), 3.98 (s, 3H), 3.97 (s, 3H); ¹³C NMR (100 MHz, DMSO-d₆) δ 158.3, 158.00, 157.97, 157.69, 156.5, 156.0, 150.0, 149.3, 136.9, 136.3, 129.8, 128.5, 127.9, 127.7, 126.1, 118.5, 115.6, 114.9, 107.1, 103.2, 100.6, 69.4, 56.5, 56.4; LC-MS (ESI+) m/z: [M+H]⁺ Calcd for C₂₃H₂₂N₃O₃ 388.2; Found 388.3.

Example 8. 6,7-Dimethoxy-N-(4-phenoxyphenyl) quinolin-4-amine hydrochloride (APS-2-16) (11.HCl)

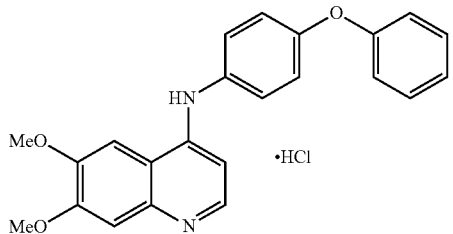 [SMILES: COc1cc2nccc(Nc3ccc(Oc4ccccc4)cc3)c2cc1OC ; Cl]

An 8 mL vial was charged with 4-chloro-6,7-dimethoxy-quinoline (50.0 mg, 0.224 mmol), 4-phenoxyaniline (45.6 mg, 0.246 mmol) and 2-propanol (1 mL). To the stirred mixture was added 1.0 M HCl (50 μL, 0.05 mmol, 22 mol %) via syringe. The vial was sealed with a screw cap and the mixture was heated at 70° C. for 16 h. The reaction was allowed to cool to room temperature and the precipitate was isolated by vacuum filtration; the collected solid was washed with hexanes (×1). Air-drying yielded 84.0 mg (92%) of the title compound as a light-yellow solid: ¹H NMR (400 MHz, DMSO-d₆) δ 14.42 (br s, 1H), 10.79 (s, 1H), 8.32 (d, J=6.8 Hz; 1H), 8.21 (s, 1H), 7.51-7.41 (m, 5H), 7.22-7.14 (m, 3H), 7.13-7.07 (m, 2H), 6.68 (d, J=6.8 Hz; 1H), 4.00 (s, 3H), 3.96 (s, 3H); ¹³C NMR (100 MHz, DMSO-d₆) δ 156.3, 155.4, 154.5, 153.4, 149.4, 139.7, 135.2, 132.6, 130.2, 127.4, 123.8, 119.6, 118.9, 111.5, 102.8, 99.8, 99.0, 56.8, 56.1; LC-MS (ESI+) m/z: [M+H]⁺ Calcd for C₂₃H₂₁N₂O₃ 373.2; Found 373.3.

Example 9. 4-(6,7-Dimethoxyquinazoline-4-ylamino)-3-methylphenol hydrochloride (APS-2-77) (19.HCl)

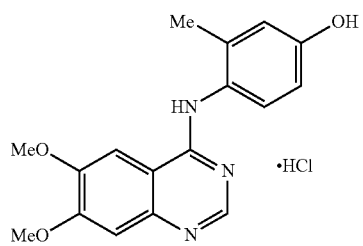 [SMILES: COc1cc2ncnc(Nc3ccc(O)cc3C)c2cc1OC ; Cl]

A 20 mL vial (with screwcap) was charged with 4-chloro-6,7-dimethoxyquinazoline (112 mg, 0.500 mmol), 4-amino-3-methylphenol (67.7 mg, 0.550 mmol) and 2-propanol (6 mL). The vial was sealed and the mixture was stirred and heated at 78° C. for 22 h. After the reaction mixture had cooled to room temperature, the precipitate was collected by vacuum filtration and the solid was washed with 2-PrOH (×1), EtOAc (×1) and hexanes (×3). Air-drying yielded 151 mg (87%) of the title compound as a light-brown solid: ¹H NMR (400 MHz, DMSO-d₆) δ 11.22 (br s, 1H), 9.63 (br s, 1H), 8.67 (s, 1H), 8.29 (s, 1H), 7.38 (s, 1H), 7.09 (d, J=8.4 Hz; 1H) 6.76 (d, J=2.4 Hz; 1H), 6.70 (dd, J=8.4, 2.4 Hz; 1H), 3.984 (s, 3H), 3.978 (s, 3H), 2.10 (s, 3H) ppm; ¹³C NMR (100 MHz, DMSO-d₆) δ 159.2, 156.8, 156.1, 150.1, 148.7, 136.1, 135.1, 128.5, 126.4, 117.0, 113.2, 106.7, 104.0, 99.7, 56.8, 56.4, 18.0 ppm; LC-MS (ESI+) m/z: [M+H]⁺ Calcd for C₁₇H₁₈N₃O₃ 312.1, Found 312.1.

Example 10. 6,7-Dimethoxy-N-(2-methyl-4-phenoxyphenyl)quinazolin-4-amine hydrochloride (APS-2-79.HCl) (21.HCl)

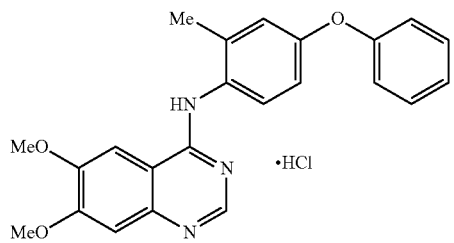 [SMILES: COc1cc2ncnc(Nc3ccc(Oc4ccccc4)cc3C)c2cc1OC ; Cl]

Step 1. 2-methyl-1-nitro-4-phenoxybenzene

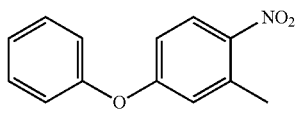 [SMILES: Cc1cc(Oc2ccccc2)ccc1[N+](=O)[O-]]

A 20 mL vial was charged with phenol (593 mg, 6.30 mmol), 4-fluoro-2-methyl-1-nitrobenzene (930 mg, 6.00 mmol), K₂CO₃ (875 mg, 6.33 mmol) and dry DMF (10 mL). The vial was sealed with a screw cap, heated at 80° C. and stirred for 10 h. After the reaction had cooled to room temperature, the mixture was partitioned between EtOAc (50 mL) and water (50 mL) in a separatory funnel. The layers were separated and the aqueous phase was extracted with EtOAc (2×50 mL). The organic extracts were pooled, washed with 1 M KOH (3×50 mL), half saturated brine (2×50 mL) and brine (50 mL), dried (MgSO$_4$) and filtered. The filtrate was concentrated under vacuum to leave 2-methyl-1-nitro-4-phenoxybenzene as an orange oil, which was used without further purification: LC-MS (ESI+) m/z: [M+H]$^+$ Calcd for C$_{13}$H$_{12}$NO$_3$ 230.1, Found 230.2.

Step 2. 2-methyl-4-phenoxyaniline

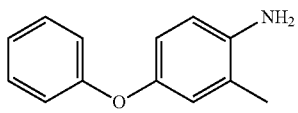

To the flask (200 mL) containing the 2-methyl-1-nitro-4-phenoxybenzene was added, Pd$^0$ (640 mg, 5% w/w on activated carbon, 0.30 mmol, 5 mol %) and then MeOH (60 mL). A stirrer bar was added to the flask and a three-way inlet-adapter (with a Teflon stopcock) was attached. The flask was evacuated (house vacuum) and backfilled with H$_2$ gas from a balloon (×5). The reaction mixture was stirred for 4 h under positive H$_2$ pressure and then filtered through a pad (3×4 cm) of Celite under vacuum; the filter-cake was washed with MeOH (×2). The combined filtrates were concentrated under vacuum to yield 1.11 g (93%) of 2-methyl-4-phenoxyaniline as a dark oil, which was used in subsequent reactions without further purification: LC-MS (ESI+) m/z: [M+H]$^+$ Calcd for C$_{13}$H$_{14}$NO 200.1; Found 200.2.

Step 3. 6,7-Dimethoxy-N-(2-methyl-4-phenoxyphenyl)quinazolin-4-amine hydrochloride (APS-2-79.HCl) (21.HCl)

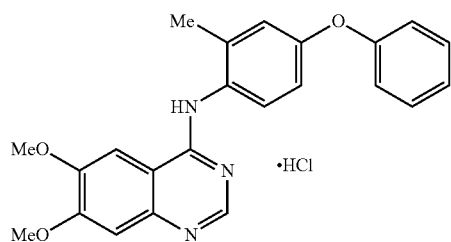 [SMILES: COc1cc2ncnc(Nc3ccc(Oc4ccccc4)cc3C)c2cc1OC ; Cl]

A portion of the above prepared 2-methyl-4-phenoxyaniline (112 mg, 0.562 mmol) was added to an 8 mL vial containing 4-chloro-6,7-dimethoxyquinazoline (105 mg, 0.467 mmol) and 2-PrOH (3 mL). The vial was sealed with a screw cap and the mixture was heated at 78° C. and stirred for 36 h. After the mixture had cooled to room temperature the precipitate was isolated by vacuum filtration (sintered glass funnel); the collected solid was washed with 2-PrOH (×2) and hexanes (×2). Air-drying yielded 170 mg (86%) of Compound 21.HCl as a white solid: $^1$H NMR (400 MHz, DMSO-d$_6$) δ 14.93 (br s, 1H), 11.43 (br s, 1H), 8.73 (s, 1H), 8.35 (s, 1H), 7.47-7.40 (m, 2H), 7.38 (s, 1H), 7.33 (d, J=8.6 Hz; 1H), 7.21-7.16 (m, 1H), 7.11-7.05 (m, 2H), 7.04 (d, J=2.7 Hz; 1H), 6.93 (dd, J=8.6, 2.7 Hz; 1H), 4.00 (s, 3H), 3.99 (s, 3H), 2.19 (s, 3H).

Example 11. (Z)—N-(6,7-Dimethoxy-1-methylquinazolin-4(1H)-ylidene)-4-phenoxyaniline (APS-3-6) (32)

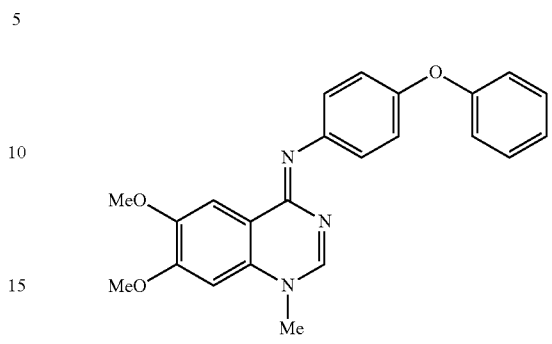

An 8 mL vial was charged with K$_2$CO$_3$ (22.1 mg, 0.160 mmol), the freebase of Compound 2 (57.1 mg, 0.153 mmol) and dry DMF (0.5 mL). To the stirred mixture was added iodomethane (0.10 mL, 10% v/v solution in DMF, 0.16 mmol) dropwise (<1 min) via syringe. The headspace of the vial was purged with Ar and the vial was sealed with a screw cap. Two additional portions (0.02 mL) of iodomethane (total: 0.14 mL, 10% solution in DMF, 0.22 mmol) were added after 14 h and 20 h. The reaction mixture was stirred under Ar for another 16 h (36 h total) and then diluted with water (0.75 mL). The mixture was stirred rapidly for 15 min and the solid was collected by vacuum filtration (sintered glass funnel); the solid was washed with 1:1 isopropanol/water (×2) and then air-dried to provide 46.5 mg of a yellow solid. The solid was recrystallized from 1:1 MeOH/water (2 mL) to yield 26.5 mg (45%) of the title compound as a yellow solid: $^1$H NMR (400 MHz, DMSO-d$_6$) δ 7.90 (s, 1H), 7.67 (s, 1H), 7.39-7.32 (m, 2H), 7.10-7.02 (m, 3H), 6.99-6.94 (m, 2H), 6.93-6.87 (m, 3H), 3.93 (s, 3H), 3.85 (s, 3H), 3.61 (s, 3H); $^{13}$C NMR (100 MHz, DMSO-d$_6$) δ 158.0, 152.6, 152.0, 150.3, 149.8, 147.5, 147.1, 133.6, 129.8, 124.2, 122.4, 119.2, 117.5, 112.9, 106.4, 98.1, 56.0, 55.6, 36.4; LC-MS (ESI+) m/z: [M+H]$^+$ Calcd for C$_{23}$H$_{22}$N$_3$O$_3$ 388.2; Found 388.3; the site of methylation was determined by NOESY analysis.

Example 12. N-(2,3-Dimethyl-4-phenoxyphenyl)-6,7-dimethoxyquinazolin-4-amine hydrochloride (APS-3-77) (50.HCl)

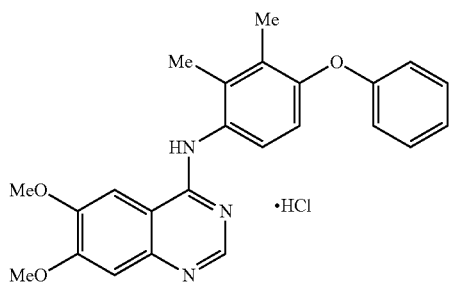 [SMILES: COc1cc2ncnc(Nc3ccc(Oc4ccccc4)c(C)c3C)c2cc1OC ; Cl]

Step 1. 2,3-Dimethyl-1-nitro-4-phenoxybenzene (APS-3-72)

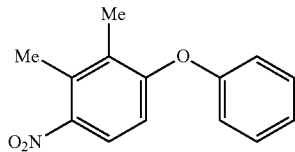

A 125 mL Erlenmeyer flask (containing a long, narrow stir bar) was charged with 2,3-dimethyl-4-nitrophenol (300 mg, 1.79 mmol), phenylboronic acid (328 mg, 2.60 mmol), copper(II) acetate (488 mg, 2.69 mmol), 4 Å molecular sieves (2 g, stored in an oven at 130° C. and finely-powdered with a mortar and pestle immediately prior to use) and $CH_2Cl_2$ (20 mL). Triethylamine (1.25 mL, 8.97 mmol) and pyridine (725 µL, 8.96 mmol) were added in a steady stream via syringe to the rapidly stirred reaction mixture. The mixture was stirred open to air for 48 h and then vacuum filtered through a pad (4×2 cm) of Celite, and the filter-cake was washed with $CH_2Cl_2$ (×2). The combined filtrates were concentrated under vacuum. The red-brown oil (377 mg) that remained was purified by silica gel chromatography (25 g cartridge), eluting at 20 mL/min and using a linear gradient of hexanes/EtOAc: 100:0→60:40 over 35 column volumes. The appropriate fractions were pooled and concentrated under vacuum to yield 127 mg (29%) of the title compound as a pink oil: LC-MS (ESI+) m/z: $[M+H]^+$ Calcd for $C_{14}H_{14}NO_3$ 244.1; Found 244.1.

Step 2. 2,3-Dimethyl-4-phenoxyaniline (APS-3-76)

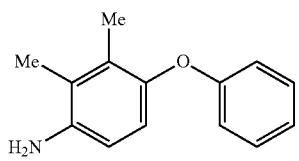 [SMILES: Cc1c(Oc2ccccc2)ccc([N+](=O)[O-])c1C]

A 50 mL flask was charged with 2,3-dimethyl-1-nitro-4-phenoxybenzene (127 mg, 0.522 mmol), $Pd^0$ (55.0 mg, 5% w/w on activated carbon, 0.026 mmol, 5 mol %) and MeOH (7 mL). A three-way inlet-adapter (with a Teflon stopcock) was attached to the flask, and the flask was evacuated and then backfilled with $H_2$ gas from a balloon (×5). The reaction mixture was stirred for 4 h under positive $H_2$ pressure and then filtered through a plug of Celite (2 cm) in a pipet (4 mL) under positive $N_2$ gas pressure; the filter-cake was washed with MeOH (×2). The combined filtrates were concentrated to yield 109 mg (98%) of the title compound as a white solid: LC-MS (ESI+) m/z: $[M+H]^+$ Calcd for $C_{14}H_{16}NO$ 214.1; Found 214.1.

Step 3. N-(2,3-Dimethyl-4-phenoxyphenyl)-6,7-dimethoxyquinazolin-4-amine hydrochloride (APS-3-77) (50.HCl)

An 8 mL vial was charged with 2,3-dimethyl-4-phenoxyaniline (109 mg, 0.511 mmol), 4-chloro-6,7-dimethoxyquinazoline (95.7 mg, 0.426 mmol) and 2-PrOH (5 mL). The vial was sealed with a screw cap and the mixture was heated at 78° C. and stirred for 18 h. After the mixture had cooled to room temperature the solid was collected by vacuum filtration (sintered glass funnel); the solid was washed with 2-PrOH, EtOAc and hexanes. Air-drying yielded 168 mg (90%) of the title compound as a white solid: $^1$H NMR (400 MHz, DMSO-$d_6$) δ 14.83 (br s, 1H), 11.41 (br s, 1H), 8.72 (s, 1H), 8.32 (s, 1H), 7.42-7.35 (m, 3H), 7.21 (d, J=8.7 Hz; 1H), 7.13-7.08 (m, 1H), 6.96-6.91 (m, 2H), 6.88 (d, J=8.7 Hz; 1H), 4.01 (s, 3H), 4.00 (s, 3H), 2.19 (s, 3H), 2.15 (s, 3H); $^{13}$C NMR (100 MHz, DMSO-$d_6$) δ 159.2, 157.4, 156.2, 152.9, 150.2, 148.91, 148.89, 136.0, 131.4, 130.0, 129.1, 126.2, 122.7, 117.4, 117.1, 106.8, 104.0, 99.8, 56.8, 56.5, 15.0, 12.7; LC-MS (ESI+) m/z: $[M+H]^+$ Calcd for $C_{24}H_{24}N_3O_3$ 402.2; Found 402.2.

Example 13. Characterization Data

Table 1 shows Compounds 1-55, which were prepared, according to one or more of the procedures provided herein, substituting the appropriate starting materials, and the corresponding characterization data.

TABLE 1

| Cmpd No. | ID # | Structure | m/z |
|---|---|---|---|
| 1·HCl | APS-1-68-1 | | 314.2[a] |

TABLE 1-continued
| Cmpd No. | ID # | Structure | m/z |
|---|---|---|---|
| 2·HCl | APS-1-68-2 | 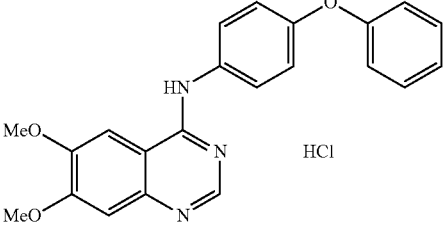 | 374.3[a] |
| 3·HCl | APS-1-70-1 | 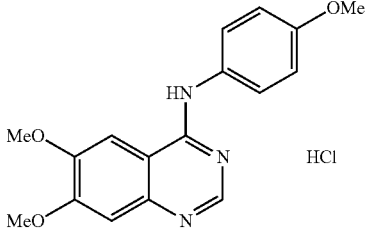 [SMILES: COc1ccc(Nc2ncnc3cc(OC)c(OC)cc23)cc1 ; Cl] | 312.3[a] |
| 4·HCl | APS-1-77-2 | 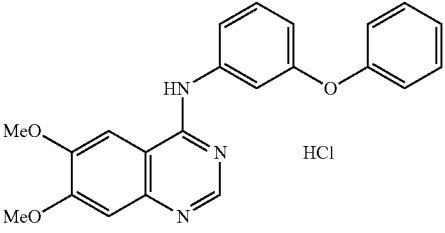 [SMILES: COc1cc2ncnc(Nc3cccc(Oc4ccccc4)c3)c2cc1OC ; Cl] | 374.2[a] |
| 5·HCl | APS-1-77-3 | 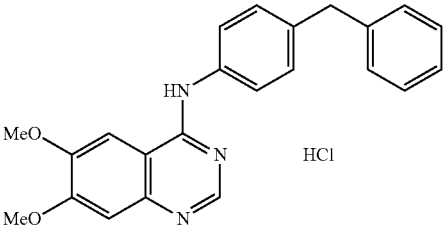 [SMILES: COc1cc2ncnc(Nc3ccc(Cc4ccccc4)cc3)c2cc1OC ; Cl] | 372.2[a] |
| 6·HCl | APS-1-77-4 | 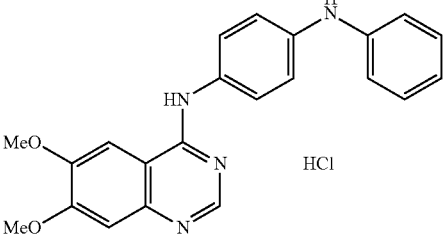 | 373.2[a] |
| 7·HCl | APS-1-82-1 | 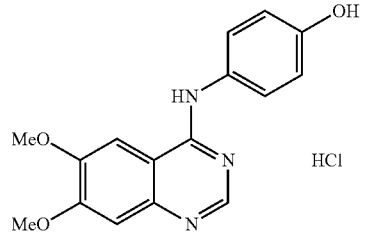 [SMILES: COc1cc2ncnc(Nc3ccc(O)cc3)c2cc1OC ; Cl] | 298.3[a] |

TABLE 1-continued
| Cmpd No. | ID # | Structure | m/z |
|---|---|---|---|
| 8·HCl | APS-1-82-2 | 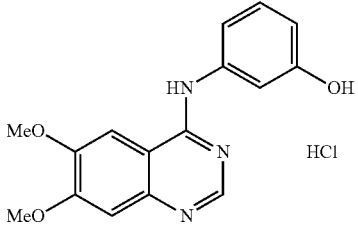 [SMILES: COc1cc2ncnc(Nc3cccc(O)c3)c2cc1OC ; Cl] | 298.3[a] |
| 9·HCl | APS-2-10 | 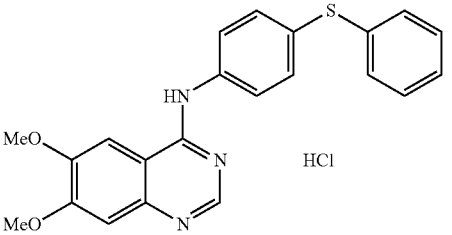 [SMILES: COc1cc2ncnc(Nc3ccc(Sc4ccccc4)cc3)c2cc1OC ; Cl] | 390.2[a] |
| 10·TFA | APS-2-12 | 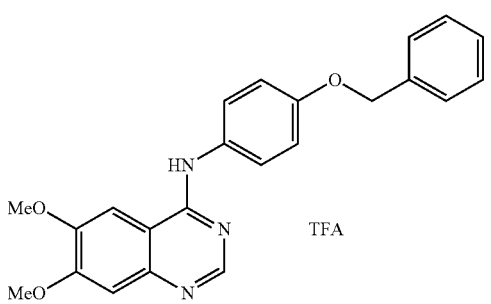 [SMILES: COc1cc2ncnc(Nc3ccc(OCc4ccccc4)cc3)c2cc1OC ; "TFA"] | 388.3[a] |
| 11·HCl | APS-2-16 | 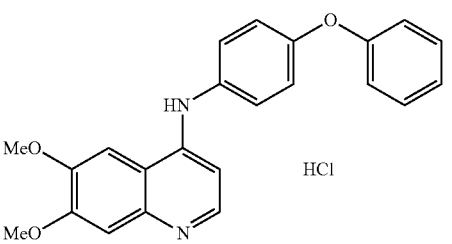 [SMILES: COc1cc2nccc(Nc3ccc(Oc4ccccc4)cc3)c2cc1OC ; Cl] | 373.3[a] |
| 12·TFA | APS-2-32-2 | 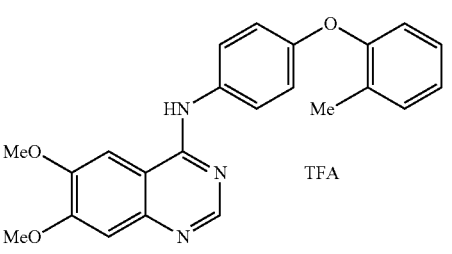 [SMILES: COc1cc2ncnc(Nc3ccc(Oc4ccccc4C)cc3)c2cc1OC ; "TFA"] | 388.3[a] |
| 13·TFA | APS-2-59-1 | 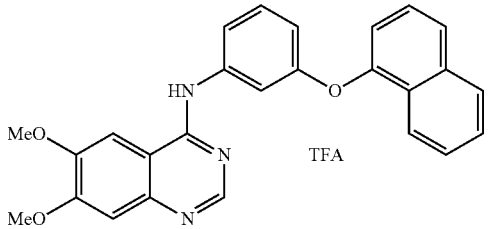 [SMILES: COc1cc2ncnc(Nc3cccc(Oc4cccc5ccccc45)c3)c2cc1OC ; "TFA"] | 424.2[a] |

TABLE 1-continued
| Cmpd No. | ID # | Structure | m/z |
|---|---|---|---|
| 14·TFA | APS-2-59-2 | 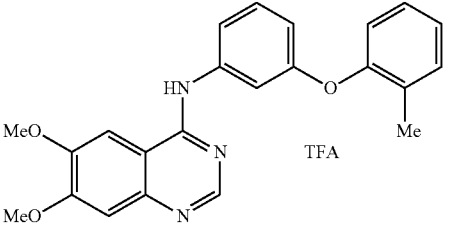 [SMILES: COc1cc2ncnc(Nc3cccc(Oc4ccccc4C)c3)c2cc1OC ; "TFA"] | 388.1[a] |
| 15·TFA | APS-2-59-3A | 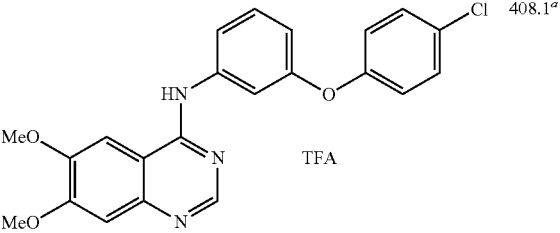 | 408.1[a] |
| 16·TFA | APS-2-59-4 | 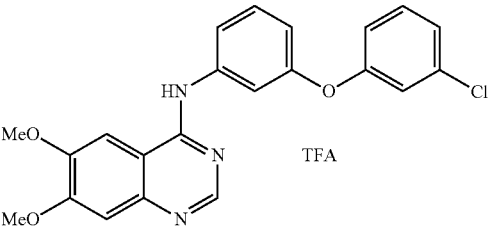 [SMILES: COc1cc2ncnc(Nc3cccc(Oc4cccc(Cl)c4)c3)c2cc1OC ; "TFA"] | 408.1[a] |
| 17·TFA | APS-2-59-5 | 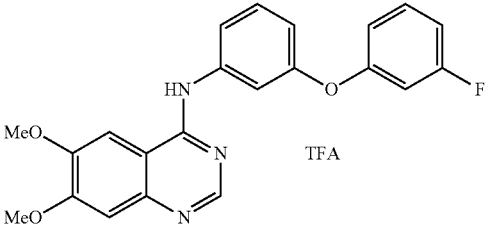 [SMILES: COc1cc2ncnc(Nc3cccc(Oc4cccc(F)c4)c3)c2cc1OC ; "TFA"] | 392.1[a] |
| 18·TFA | APS-2-60-1A | 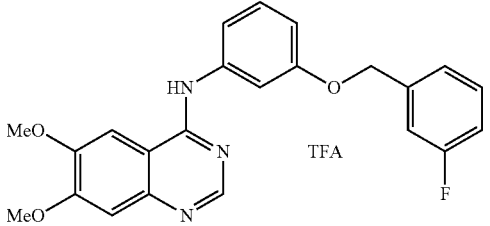 [SMILES: COc1cc2ncnc(Nc3cccc(OCc4cccc(F)c4)c3)c2cc1OC ; "TFA"] | 406.1[a] |
| 19·HCl | APS-2-77 | 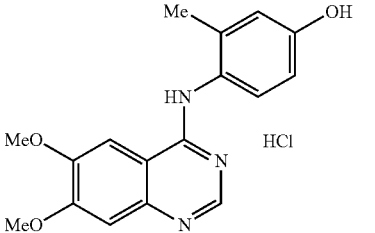 [SMILES: COc1cc2ncnc(Nc3ccc(O)cc3C)c2cc1OC ; Cl] | 312.1[a] |

TABLE 1-continued

| Cmpd No. | ID # | Structure | m/z |
|---|---|---|---|
| 20·HCl | APS-2-78 | | 348.2[a] |
| 21·HCl | APS-2-79 | | 388.3[a] |
| 21·TFA | APS-2-79 | | 388.2[a] |
| 22·HCl | APS-2-84 | | 312.1[a] |
| 23 | APS-2-85 | | 424.3 |

TABLE 1-continued

| Cmpd No. | ID # | Structure | m/z |
|---|---|---|---|
| 24 | APS-2-86 | (6,7-dimethoxyquinazolin-4-yl)-NH-(3-methyl-4-phenoxyphenyl) | 388.3 |
| 25·HCl | APS-2-87-1 | (6,7-dimethoxyquinazolin-4-yl)-NH-(2-chloro-5-hydroxyphenyl)·HCl | 332.2[a] |
| 26·HCl | APS-2-87-2 | (6,7-dimethoxyquinazolin-4-yl)-NH-(4-methyl-3-hydroxyphenyl)·HCl | 312.2[a] |
| 27·HCl | APS-2-88 | (6,7-dimethoxyquinazolin-4-yl)-NH-(2-fluoro-4-hydroxyphenyl)·HCl | 316.1[a] |
| 28 | APS-2-90 | (6,7-dimethoxyquinazolin-4-yl)-O-(4-phenoxyphenyl) | 375.2 |
| 29·HCl | APS-2-92 | (6,7-dimethoxyquinazolin-4-yl)-NH-CH2-(4-phenoxyphenyl)·HCl | 388.3[a] |

TABLE 1-continued

| Cmpd No. | ID # | Structure | m/z |
|---|---|---|---|
| 30·HCl | APS-2-95 | 6,7-dimethoxyquinazolin-4-yl-NH-(4-methyl-3-hydroxyphenyl), HCl | 312.2[a] |
| 31 | APS-3-5 | 6,7-dimethoxyquinazolin-4-yl-S-(4-phenoxyphenyl) | 391.3 |
| 32 | APS-3-6 | 6,7-dimethoxy-1-methylquinazolin-4(1H)-ylidene-N-(4-phenoxyphenyl) | 388.3 |
| 33·HCl | APS-3-15 | 6,7-dimethoxyquinazolin-4-yl-NH-(3-methyl-5-hydroxyphenyl), HCl | 312.2[a] |
| 34 | APS-3-17-2 | 6,7-dimethoxyquinazolin-4-yl-NH-(4-methyl-3-phenoxyphenyl) | 388.3 |
| 35 | APS-3-17-4 | 6,7-dimethoxyquinazolin-4-yl-NH-(2-methyl-5-phenoxyphenyl) | 388.3 |

TABLE 1-continued
| Cmpd No. | ID # | Structure | m/z |
|---|---|---|---|
| 36 | APS-3-17-5 | 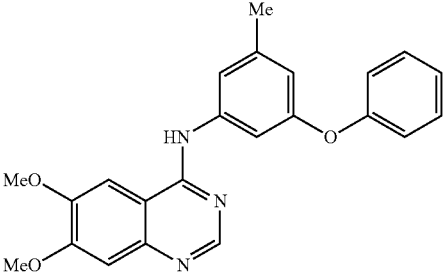 [SMILES: COc1cc2ncnc(Nc3cc(C)cc(Oc4ccccc4)c3)c2cc1OC] | 388.3 |
| 37 | APS-3-26-1 | 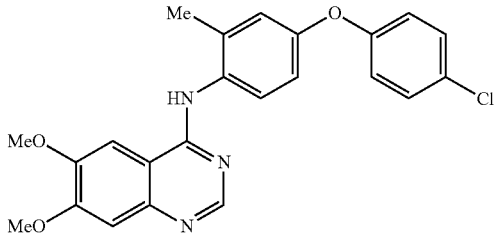 [SMILES: COc1cc2ncnc(Nc3ccc(Oc4ccc(Cl)cc4)cc3C)c2cc1OC] | 422.3 |
| 38 | APS-3-26-2 | 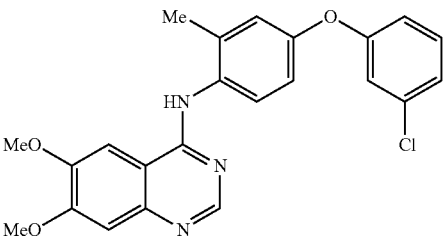 [SMILES: COc1cc2ncnc(Nc3ccc(Oc4cccc(Cl)c4)cc3C)c2cc1OC] | 422.3 |
| 39 | APS-3-26-3 | 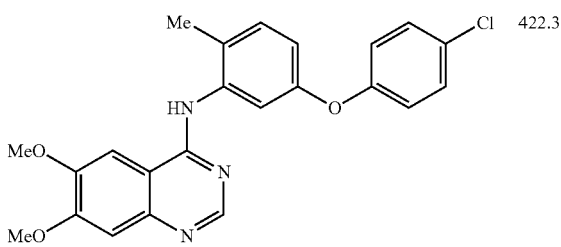 | 422.3 |
| 40 | APS-3-26-4 | 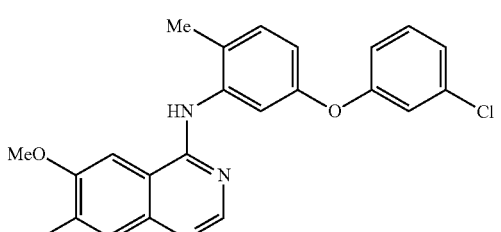 | 422.3 |
| 41 | APS-3-26-5 | 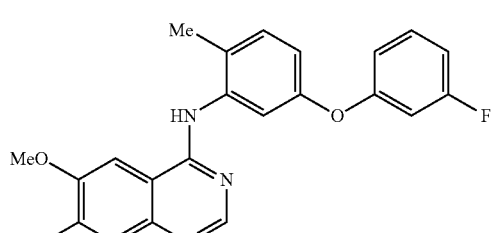 | 406.4 |

TABLE 1-continued

| Cmpd No. | ID # | Structure | m/z |
|---|---|---|---|
| 42 | APS-3-29 | 6,7-dimethoxy-N-(2-bromo-5-phenoxyphenyl)quinazolin-4-amine | 452.2 |
| 43 | APS-3-31 | 6,7-dimethoxy-4-(4-phenoxybenzyl)quinazoline | 373.3 |
| 44 | APS-3-44-1 | 6,7-dimethoxy-N-(2-fluoro-4-phenoxyphenyl)quinazolin-4-amine | 392.3 |
| 45·HCl | APS-3-44-2 | 6,7-dimethoxy-N-(2-chloro-4-phenoxyphenyl)quinazolin-4-amine·HCl | 408.3[a] |
| 46·HCl | APS-3-44-3 | 6,7-dimethoxy-N-(3-fluoro-4-phenoxyphenyl)quinazolin-4-amine·HCl | 392.3[a] |
| 47·HCl | APS-3-44-4 | 6,7-dimethoxy-N-(3-chloro-4-phenoxyphenyl)quinazolin-4-amine·HCl | 408.3[a] |

TABLE 1-continued
| Cmpd No. | ID # | Structure | m/z |
|---|---|---|---|
| 48·HCl | APS-3-63 | 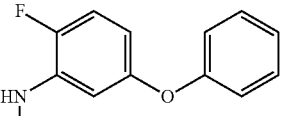 | 392.2[a] |
| 49·HCl | APS-3-74-1 | 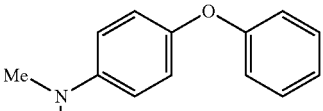 | 388.2[a] |
| 50·HCl | APS-3-77 | 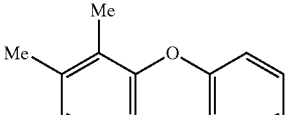 | 402.2[a] |
| 51·HCl | APS-3-85 | 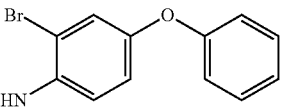 | 452.1[a] |
| 52·HCl | APS-3-95 | 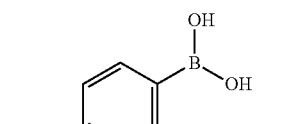 | 326.1[a] |
| 53 | APS-3-99 | 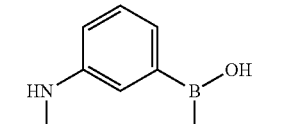 | 326.1 |

TABLE 1-continued

| Cmpd No. | ID # | Structure | m/z |
|---|---|---|---|
| 54•HCl | APS-4-15 | 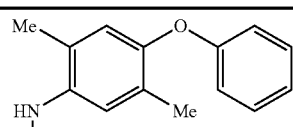 6,7-dimethoxyquinazolin-4-amine with N-H linked to 2-methyl-4-phenoxy-5-methylphenyl, HCl salt | 402.2[a] |
| 55•HCl | APS-4-16 | 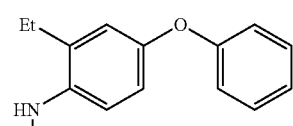 6,7-dimethoxyquinazolin-4-amine with N-H linked to 2-ethyl-4-phenoxyphenyl, HCl salt | 402.2[a] |

[a] m/z corresponds to free base form.

Example 14. Expression and Purification of hKSR2-rMEK1

Human KSR2 (residues 634-950) and rabbit MEK1 (residues 1 to 393) were codon optimized for insect cell expression by DNA 2.0. Inserts were expressed with TEV cleavable 6x-His tags from the pFastBac Dual expression vector. Bacmids were used to transfect adherent SF21 cells and viruses were subsequently titred to high levels through serial infections of SF21 cells. Large-scale infections (1 L of 2×106 cells/mL) were infected at a M.O.I. of approximately 1 and typically yielded 2-4 mg of final purified KSR2-MEK1 complexes. Briefly, following infections, cells were harvested, lysed, and affinity purified using Co2+ sepharose resin (GoldBio). Elutes from the first affinity step were dialysed and cleaved with the TEV protease at 4 degree C. for approximately 8 hours in buffer containing 25 mM Tris pH 7.5, 200 mM NaCl, and 5 mM DTT. Dialysis retentate was diluted 3 fold and then applied to a Resourse S ion exchange column. This step removed excess MEK1, which binds weakly to the S column. One-to-one hKSR2-MEK1 complexes were captured in late fractions from an increasing salt gradient. Complexes were later applied to a 120 mL Superdex 200 gel filtration column and finally concentrated to approximately 10 mg/mL before flash freezing for biochemical assays.

Example 15. ATP-Biotin Probe Labeling and Inhibitor Competition

Figure 2:
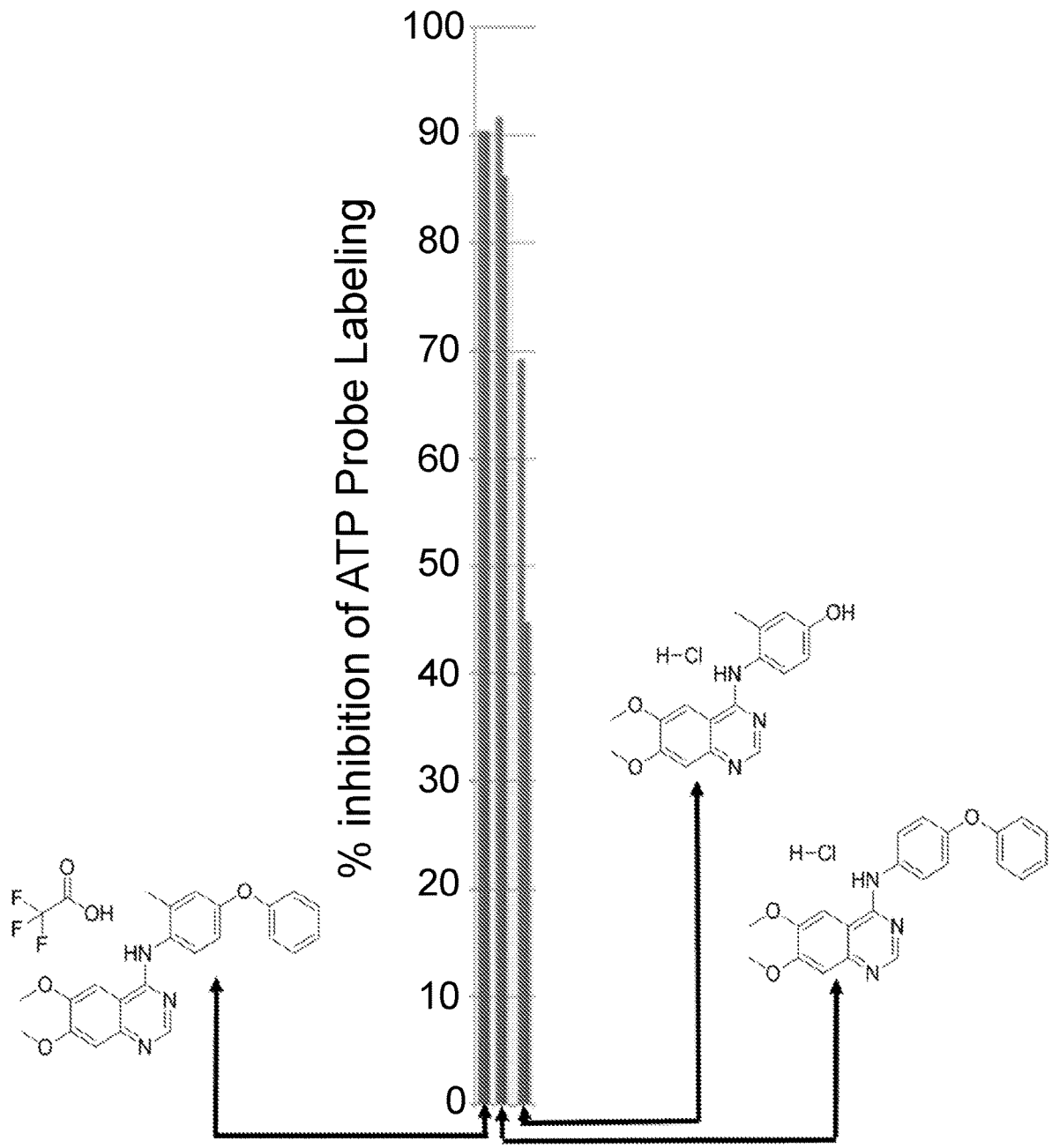
FIG. 2 shows % inhibition of ATP probe labeling for the compounds of Examples 1-3. Left grey bars=MEK; Right grey bars=KSR.

The ATP-biotin assay was performed in buffer containing 25 mM Tris pH 7.5, 150 mM NaCl, 10 mM MgCl$_2$, and 2% DMSO. Purified hKSR2-rMEK1 was assayed at 0.5 µM. In particular, hKSR2-rMEK1 was pre-incubated with 20 µM of the indicated compounds for 15 minutes. Then, ATP-biotin (Pierce Cat. #88310) was added to a final concentration of 2 µM. Reactions were incubated at room temperature for 5 minutes before being stopped by the addition of 6×SDS loading dye. Samples were then electrophoresed on a 4-15% Tris-HCl SDS gradient gel, transferred to nitrocellulose membranes and blotted with Strepdavidin-HRP. Enhanced chemiluminescence signals corresponding to labeling on KSR2 and MEK1 were visualized and quantified using the Biodoc system (Biorad). Relative signals of Streptavidin HRP on bands corresponding to KSR2 and MEK1 in the presence of compounds relative to DMSO controls were used to determine 'Percent Inhibition of ATP Probe Labeling'. Control experiments using ATP as a competitor were used to determine that the ATP-biotin probe specifically labels the active-site of KSR2 and MEK1. Representative results of the ATP-biotin assay are shown in FIGS. 1-2.

Figure 3:
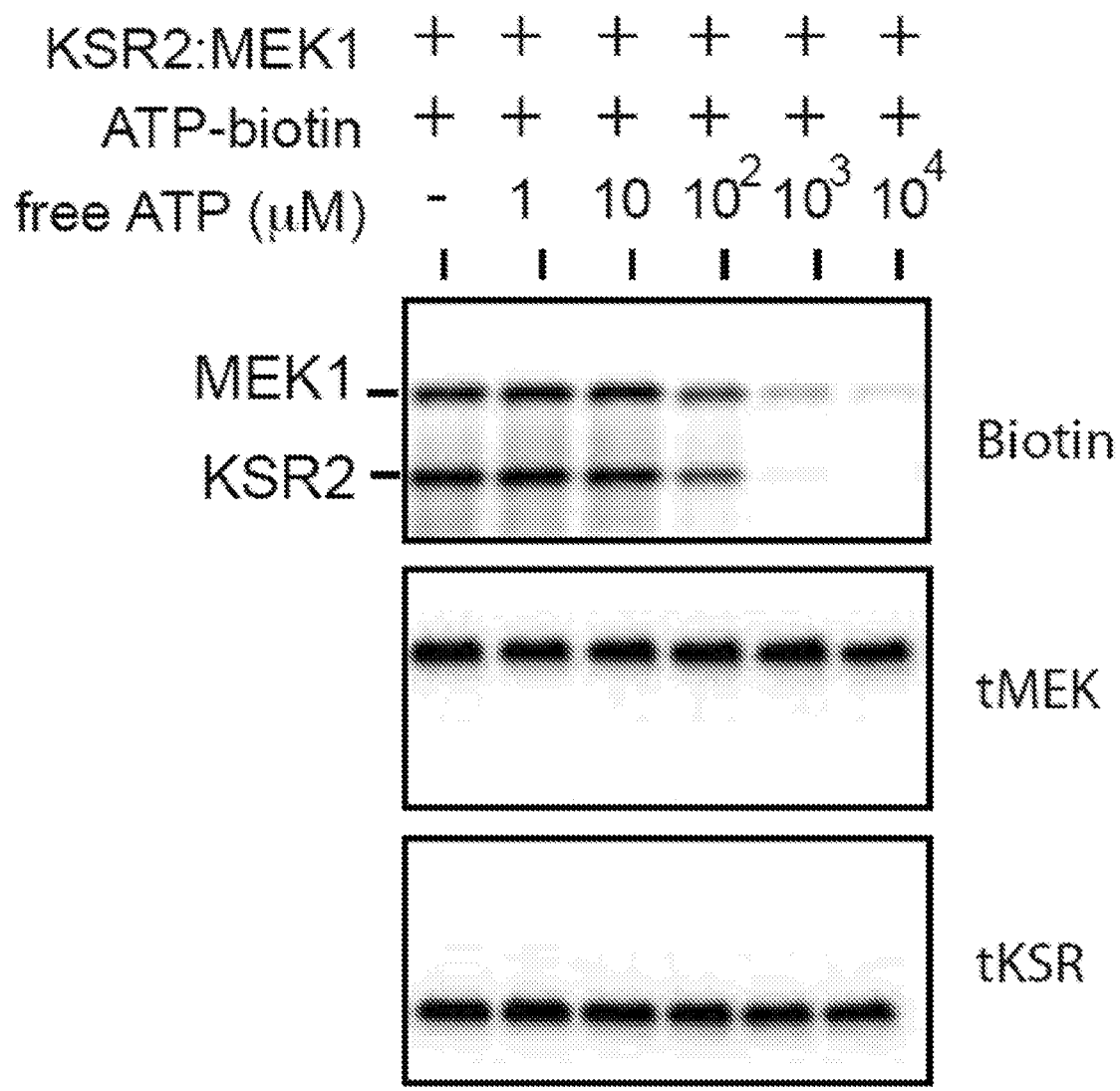
FIG. 3 shows labeling of ATP-binding pockets of purified KSR2:MEK1 complexes using an activity based probe (ATPbiotin).
Figure 4:
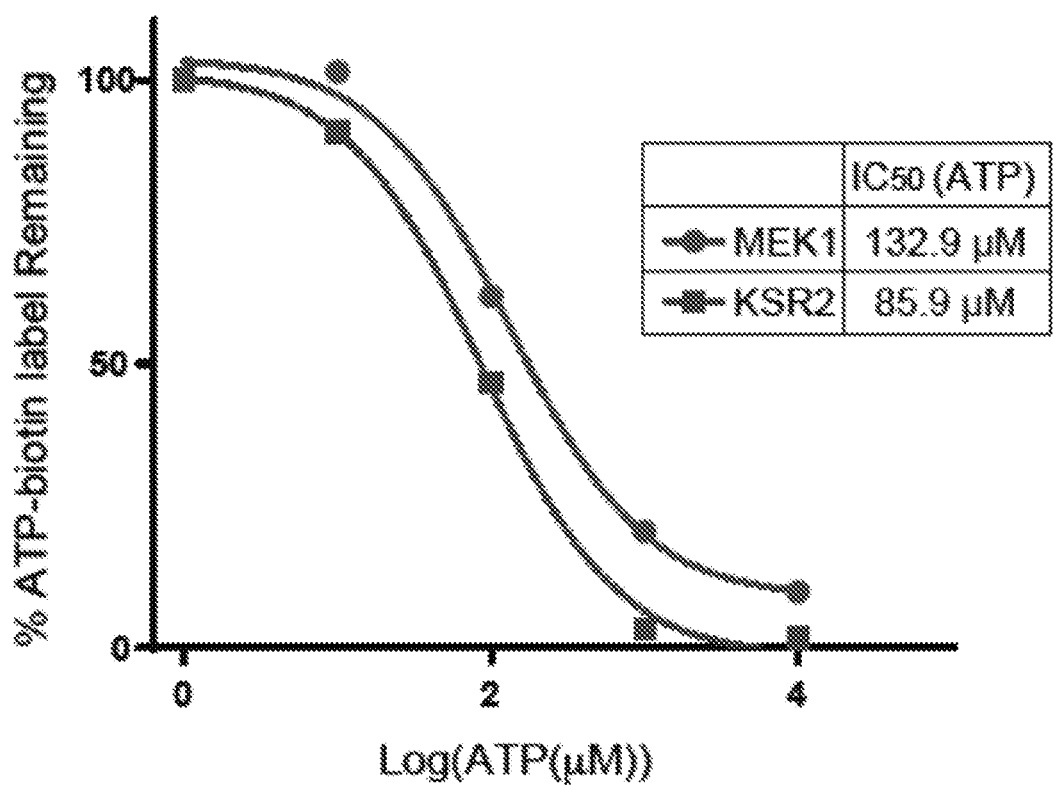
FIG. 4 shows a graphical representation for ATPbiotin probe labeling of KSR2-MEK1 complexes in the presence of increasing free ATP as shown in FIG. 3. Corresponding $IC_{50}$ values are listed for both KSR2 and MEK1.

ATP$^{biotin}$ transfers a desthio-biotin group via a reactive acyl-phosphate linkage onto active-site lysines when bound to either KSR2 or MEK1 (Patricelli et al, *Biochemistry*, 2007, 46:350-358). It was confirmed that this label leads to a covalent attachment of desthiobiotin on KSR through detection with Streptavidin-HRP and intact mass spectrometry, the latter of which confirmed the addition of a two or one desthiobiotin groups (equivalent to a mass increase of 196.1 Da per desthiobiotin group) onto both KSR2 and MEK1, respectively, under non-saturating conditions. Without being bound by theory, competition experiments with free ATP suggested that ATP$^{biotin}$ labeling occurred within the active sites of both KSR2 and MEK1, as shown in FIG. 3, and free ATP IC$_{50}$ values of 86 µM and 133 µM, respectively, were measured as shown in FIG. 4. Results of the ATP based competition experiments support the utility of this assay for identifying direct binders of KSR2, MEK1, or both kinases within purified complexes.

For the ATP$^{biotin}$ labeling competition screen, samples were applied to a 4-20% Tris-HCl gel, separated, and then transferred to a nitrocellulose membrane. The membrane was blocked with 5% bovine serum albumin diluted in TBS-T for 30 minutes and subsequently probed with the Pierce™ High Sensitivity Streptavidin-HRP. After several washes, the membranes were visualized using enhanced chemiluminescence on a Biodoc (Biorad). IC$_{50}$ values were determined under similar assay conditions with slight modifications: 0.1 µM KSR2:MEK1 was pre-incubated with a dose-range of compounds (27 nM to 20 µM in three-fold dilutions prior to the addition of ATP$^{biotin}$. Assays were quenched and analysed similarly to as described above.

Sigmoidal dose response curves were used to derive $IC_{50}$ values in Prism 6.0 (Graphpad). Assays were completed in triplicate.

Figure 5:
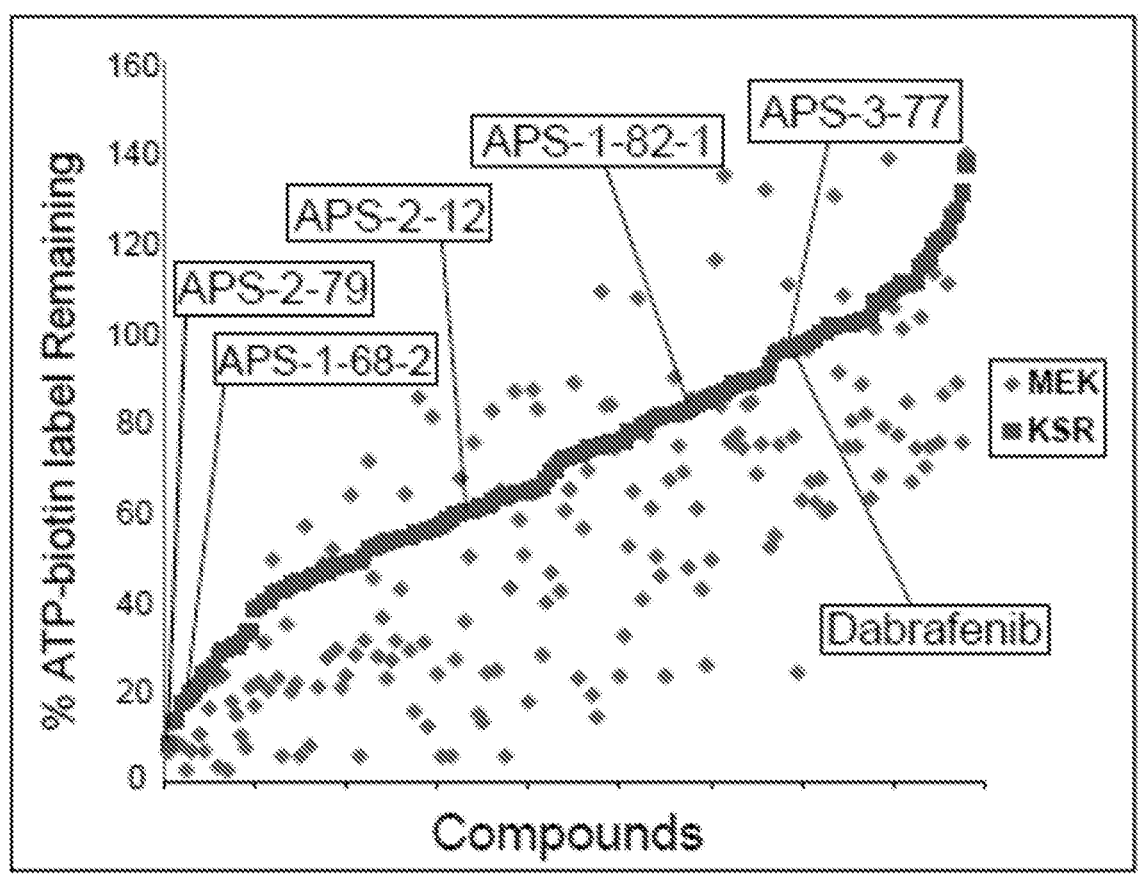
FIG. 5 shows results of a screen for direct competitors of ATP-biotin probe labeling of MEK and KSR.

A collection of 176 structurally diverse commercially available and in-house synthesized kinase inhibitors were screened for direct competition of $ATP^{biotin}$ probe labeling, as shown in FIG. 5. From this analysis, Compound 2 was identified as a competitor of probe labeling in KSR2:MEK1 complexes. This quinazoline biphenyl ether compound has previously been described as both a Src and EGFR family kinase inhibitor. Synthetic modification of Compound 2, generated variable structure activity relationships (SAR). KSR2 $IC_{50}$ data for representative compounds are shown below in Table 2.

TABLE 2

| Compound No. | ID No. | KSR2 $IC_{50}$ (μM) |
|---|---|---|
| 2•TFA | APS-1-68-2 | 0.602 ± 0.205 |
| 21•TFA | APS-2-79 | 0.120 ± 0.023 |
| 50•TFA | APS-3-77 | >10 |
| 7•TFA | APS-1-82-1 | >10 |
| 10•TFA | APS-2-12 | 1.5 ± 0.2 |
| 3•TFA | APS-1-70-1 | >10 |
| 11•TFA | APS-2-16 | 2.5 ± 0.2 |
| 32•TFA | APS-3-6 | >10 |

Example 16. Identification of Ras-MAPK Pathway Antagonists

To assess the biological function of lead compounds as Ras-MAPK pathway antagonists, a simplified cell-based reconstitution system was developed to directly monitor KSR-driven MAPK signaling. This system, in which cellular MAPK signaling is dependent on KSR expression, was found to be sensitive to known Ras suppressor mutations in KSR. Likewise, Compound 21 also suppressed KSR-stimulated MEK and ERK phosphorylation. The suppression of MAPK signaling by Compound 21 was dependent on direct targeting of KSR as an active site mutant ($KSR^{A690F}$), which has previously been demonstrated to stimulate KSR-based MAPK outputs independent of ATP-binding (see e.g., Hu et al, Cell, 2013, 154:1036-1046), greatly diminished the activity of Compound 21. Notably, a negative control for KSR-binding (Compound 50) was inactive whereas a positive control RAF inhibitor, dabrafenib, was active irrespective of the KSR-mutational status. Based on similarity in phenotype and direct-binding activity, Compound 21 was identified as a small molecule mimic of KSR alleles that suppress oncogenic Ras mutations.

Example 17. Crystallization of KSR2(KD):MEK1 Complexed with Compound 21.TFA

For crystallization studies, the final size exclusion chromatography step of the human KSR2 kinase domain (KSR2 (KD)):MEK1(35-393) purification was performed in buffer containing 15 mM Bis-Tris pH 6.5, 150 NaCl, 1 mM TCEP, and 5 mM DTT. The KSR2(KD):MEK1(35-393) complex was concentrated to 10 mg/mL and incubated with 500 μM Compound 21.TFA. Aggregates were removed through centrifugation at 14,000 g for 10 minutes. Over a thousand conditions were screen using in-house and sparse matrix screens via sitting-drop methods at 4, 10, and 22° C. Multiple conditions resulted in crystal formation, but ultimately the highest quality diffracting crystals arose from a condition containing 12% PEG-3350, 100 mM Bis-Tris pH 6.25, 200 mM sodium citrate, and 10 mM Magnesium Acetate. Crystals were flash-frozen following step-wise soaking in mother liquor spiked with increasing concentrations of ethylene glycol (25% maximum). A 3.5 Å data set was collected at the Advanced Photon Source (Argonne National Laboratory). Diffraction images were indexed and scaled using XDS. The structure of KSR2(KD):MEK1 in complex with Compound 21 was solved by molecular replacement using Phaser based on searches of the KSR2 (KD) and MEK1 models derived from the KSR2(KD): MEK1:ATP crystal structure (PDB code: 2Y4I). Model building and refinement was performed with Coot and Phenix (see e.g., Emsley et al, Acta crystallographica. Section D, Biological crystallography, 2010, 66:486-501; and Adams et al, Acta crystallographica. Section D, Biological crystallography, 2010, 66:213-221). Crystals for the ATP and Compound 21 bound KSR2:MEK1 complexes share similar unit cell dimensions, space group symmetry, and X-ray diffraction properties.

Figure 6:
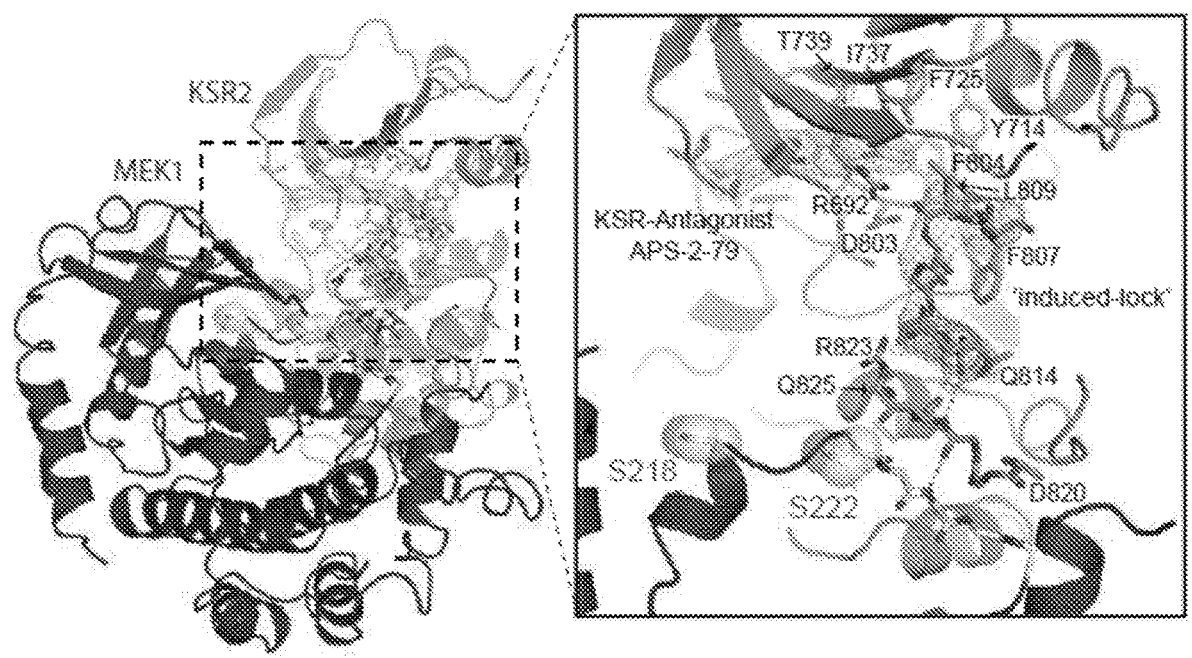
FIG. 6 shows a crystal structure of KSR2:MEK1, assembled via a face-to-face interaction. Within this arrangement, two key phospho-regulatory residues in MEK1, Ser218 and Ser222, are buried and protected from the action of RAF. Inset includes a magnified view of interactions between KSR2, MEK1, and Compound 21. Compound 21 and an extended segment that reinforces negative-regulatory interactions of KSR2 on MEK1 are shown within 2|Fo|−|Fc| electron density maps contoured at 1.5σ.

Previous studies established that genetic suppressors in KSR may impede RAF-induced conformational changes in KSR required for MEK activation or destabilize KSR-MEK and KSR-RAF complexes (see e.g., Rajakulendran et al, Nature, 2009:542-545; Roy et al, Genes & Development, 2002, 16:427-438; Stewart et al, Molecular and Cellular Biology, 1999, 19:5523-5534; and Lavoie et al, Nature Chemical Biology, 2013, 9:428-436). To distinguish between these, and other possibilities, an X-ray crystal structure of the KSR2:MEK1 complex bound to Compound 21 was determined, as shown in FIG. 6. In the Compound 21 bound state, KSR2 binds MEK1 in a 1:1 fashion within a quaternary arrangement that is nearly identical to the ATP-bound state of KSR2:MEK1 complexes (see e.g., Brennan et al, Nature, 2011, 472:366-369). Within both states, KSR2 and MEK1 bind via a face-to-face arrangement mediated in large part through reciprocal helix αG and activation segment interactions, and KSR2 homo-dimerizes through the N-lobe along a crystallographic 2-fold symmetry axis producing a hetero-tetramer of KSR2:MEK1 dimers. Differences between the ATP- and Compound 21 bound states include variations in ligand occupancy and conformational changes at the level of secondary structural elements that are localized to KSR2.

In the ATP-bound state, both KSR2 and MEK1 were modeled bound to ATP. However, in the Compound 21 bound state, only KSR2 was found to possess strong electron density that could be assigned to Compound 21. Two segments of Compound 21 engage distinct regions in KSR2. First, the biphenyl ether extends to a sub-pocket within KSR2 defined by Thr739, Arg692, Asp803, and a hydrophobic shell composed of Phe725, Tyr714, Phe804, and Leu806. Stacking interactions between the terminal phenyl in Compound 21 and Phe725, Tyr714, and Phe804 in particular are expected to provide strong interactions between KSR2 and Compound 21 through the arrangement of a four-member aromatic pair network. Within proteins, such networks are energetically favorable and increasing the number of pairs can dramatically increase stability (see e.g., Burley et al, Science, 1985, 229:23-28). The existence of this network is substantiated by removal of the terminal phenyl in Compound 21-like compounds, which greatly diminished competition of $ATP^{biotin}$ probe labeling in KSR2. Second, an H-bond between the N1 in the quinazoline core of Compound 21 and the backbone at Cys742 further mediates Compound 21:KSR2 interactions. Notably, substitution of the N1 with a methyl group (Compound 32) greatly diminishes KSR2:MEK1 activity, whereas replacement of the N3 with —CH (Compound 11) was moderately tolerated. Therefore, based on crystallographic analysis and SAR data, it was determined that Compound 21 binds directly to KSR2 within the KSR2:MEK1 complex.

In the ATP-bound KSR2:MEK1 structure, the MEK1 activation segment, containing two phospho-regulatory sites (Ser218 and Ser222) necessary for MEK1 activation, is buried within the KSR2:MEK1 interaction interface. Biochemical experiments revealed that KSR2:B-RAF dimerization can release this inhibitory interaction to promote MEK1 phosphorylation (see e.g., Brennan et al, Nature, 2011, 472:366-369). The KSR2:MEK1:Compound 21 structure revealed electron density for a portion of KSR2 that was not previously modeled, and therefore disordered in the ATP-bound complex, as shown in FIG. 6. This region, encompassing residues Leu809 to Gln814, forms an extension of the activation segment C-terminal to the conserved DFG motif, and forms an anti-parallel beta-strand with residues Asp820 to Gln825 in KSR2. In both the Compound 21 and ATP-bound states of KSR2:MEK1, Asp820 through to Gln825 directly engages the activation segment of MEK1 burying the Ser218-Ser222 region, presumably shielding this segment of MEK from promiscuous phosphorylation. Additionally, the ordering of residues Leu809 to Gln814 in KSR2 occurs at the expense of disorder of residues Lys674 to Arg676 in the P-loop, which in the ATP-bound state directly coordinates beta and gamma phosphates. The two modes by which ATP and Compound 21 impact KSR-based interactions on MEK appear mutually exclusive as both ligands induce conformations that would otherwise compete with one another. Without being bound by theory, these structures were interpreted to suggest that the ATP-bound state represents a transition conformation in the MEK activation pathway, whereas Compound 21 stabilizes an inactive state of KSR2 characterized by reinforcement of negative regulatory interactions. The model suggests that Compound 21 behaves as a KSR-dependent antagonist of MEK phosphorylation by RAF by shifting the equilibrium of KSR-MEK complexes so as to populate the OFF state.

Example 18. RAF Phosphorylation Assay

B-RAF was purified as previously described with slight modification (see e.g., Tsai et al, *Proceedings of the National Academy of Sciences of the United States of America*, 2008, 105:3041-3046). In particular, a variant of B-RAF was identified that could be expressed in high yield from *E. Coli* and which also retained near wild-type levels of kinase activity towards MEK1. For in vitro kinase assays, indicated concentrations of B-RAF and 1 μM KSR2-MEK1 or 1 μM MEK1 proteins were pre-incubated with 10 μM of indicated compounds for 15 minutes in buffer containing 25 mM Tris pH 7.5, 150 mM NaCl, 10 mM $MgCl_2$, and 2% DMSO. Kinase reactions were initiated by the addition of 100 μM ATP and halted at the indicated times by the addition of 6×SDS loading dye. Samples were examined by western blotting as described for the ATP-biotin experiments and by probing overnight with a MEK1/2 Ser218-Ser222 phospho-specific antibody (Cell signaling). Membranes were visualized using enhanced chemiluminescence on a Biodoc (Biorad) for quantification purposes.

RAF can function as both an allosteric regulator of KSR and catalytic enzyme responsible for MEK phosphorylation (see e.g., Farrar et al, *Nature*, 1996, 383:178-181; Brennan et al, *Nature*, 2011, 472:366-369; Huang et al, *Proceedings of the National Academy of Sciences of the United States of America*, 1993, 90:10947-10951; and Michaud et al, *Proceedings of the National Academy of Sciences of the United States of America*, 1997, 94:12792-12796). Without being bound by theory, comparison of the ATP- and Compound 21 bound states of KSR2:MEK1 suggested that Compound 21 antagonizes RAF phosphorylation on MEK indirectly by impeding KSR-RAF heterodimers. Indeed, coincident with Compound 21 binding, the dimer interface of KSR2, including residues Trp685 and His686, demonstrates perturbations relative to the ATP bound conformation. Mutations within this interface, including R718H in KSR2 and analogous R509H in B-RAF have been demonstrated to impede signaling by RAF dimers (see e.g., Rajakulendran et al, *Nature*, 2009, 461:542-545; Brennan et al, *Nature*, 2011, 472:366-369; and Poulikakos et al, *Nature*, 2011, 480:387-390). To directly investigate the impact of Compound 21 on KSR2:B-RAF dimerization, bio-layer inferometry (BLI) was utilized to monitor real-time association and dissociation of KSR2:MEK1 or free MEK1 to a sensor tethered with immobilized B-RAF.

Figure 7A:
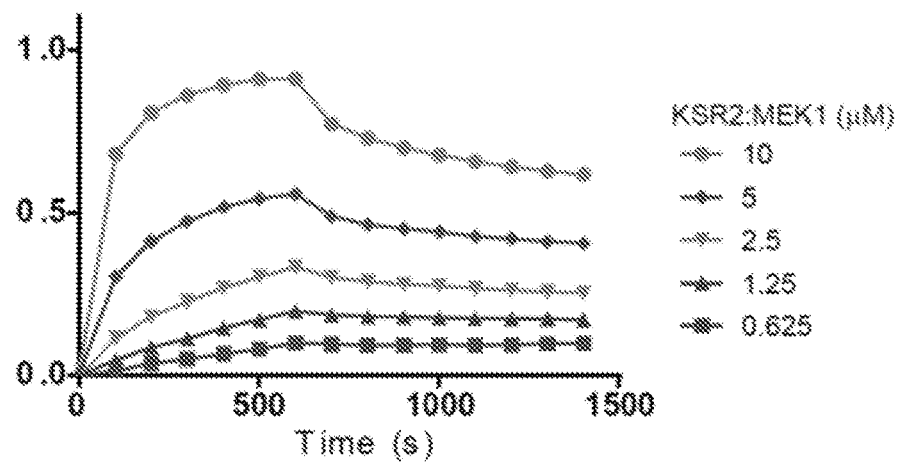
FIGS. 7A-7G shows results of a biolayer inferometry assay. B-RAF and B-RAF mutants (F667E+/−R509H) were immobilized on sensor-heads and KSR2:MEK1 or MEK1 assembly was monitored. Curves indicate dose ranges of KSR2:MEK1 or MEK1 from 625 nM to 10 µM. In all plots, association occurred from 0 to 660 seconds, and dissociation was monitored thereafter up to 1500 seconds. Compound 21 and trametinib were added in the presence of KSR2:MEK1 at a concentration of 25 µM each.
Figure 7B:
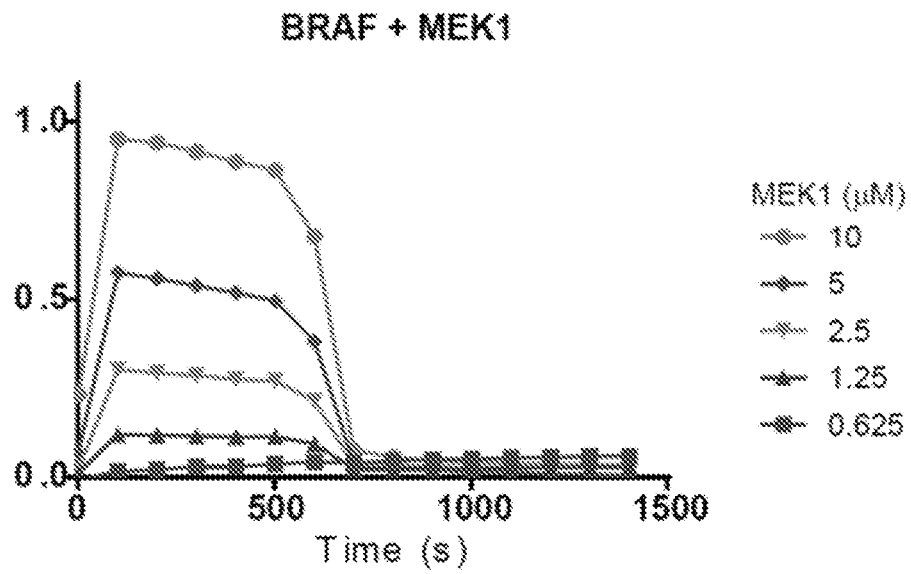

In control experiments, KSR2:MEK1 complexes were found to associate with immobilized B-RAF in a non 1:1 fashion, as shown in FIG. 7A. Without being bound by theory, this association is due to the formation of higher-order B-RAF:KSR2:MEK1 complexes. In contrast, B-RAF bound to free MEK1 in a 1:1 fashion with a $K_D$=51+/−3.8 nM, as shown in FIG. 7B.

Figure 7C:
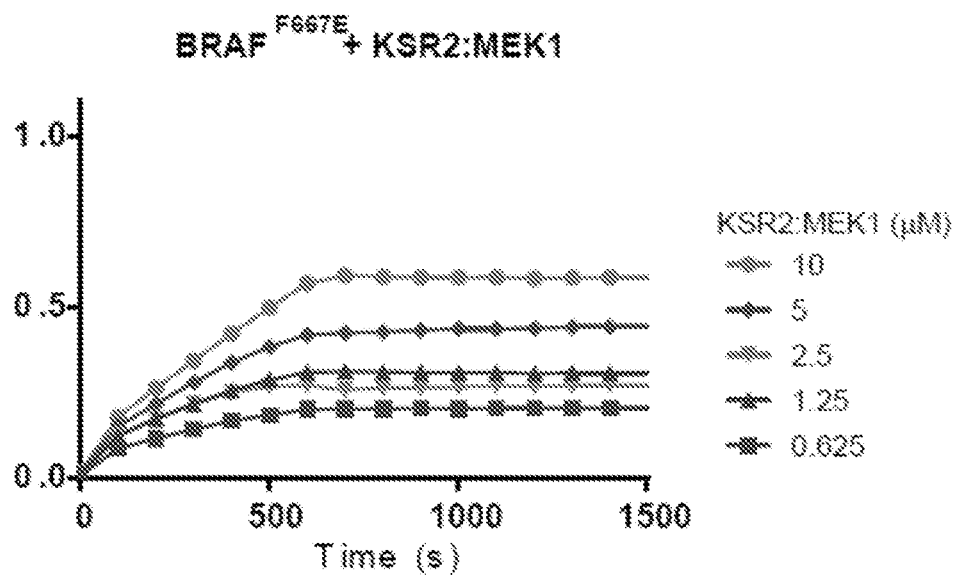
Figure 7D:
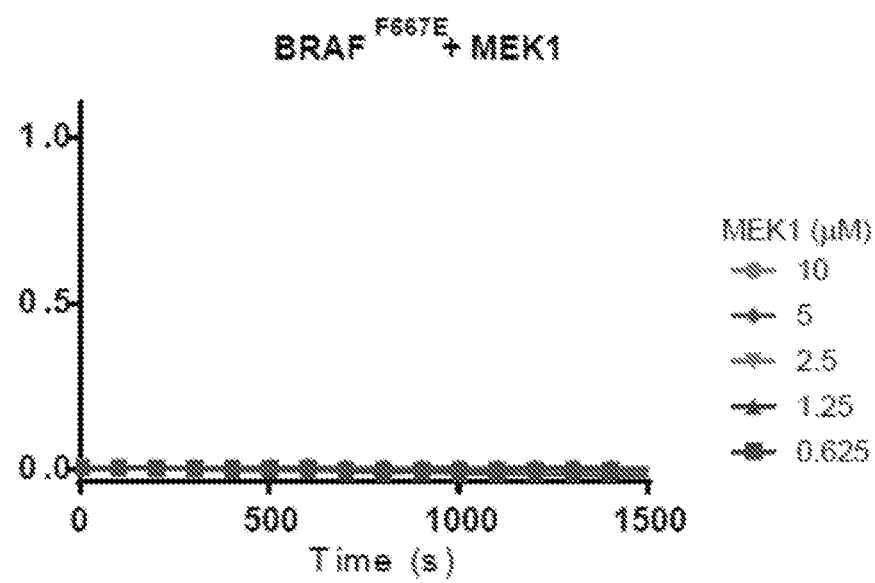
Figure 7E:
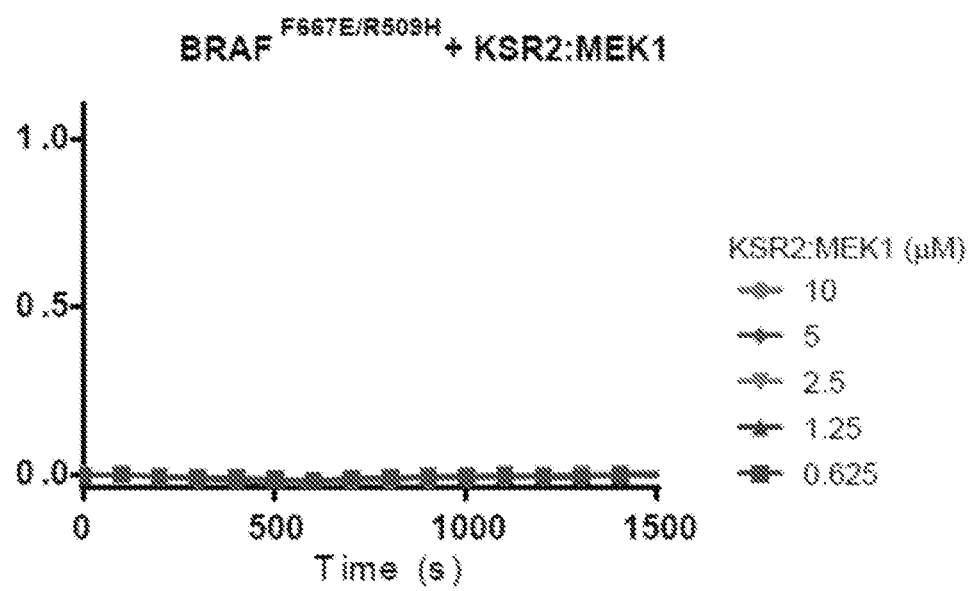

To specifically monitor KSR2:B-RAF dimerization relative to other possible interactions, a mutation in B-RAF$^{F667E}$ was identified that eliminates binding to free MEK but not KSR2-MEK1 complexes, as shown in FIGS. 7C-7D. KSR2:MEK1 interacted in a 1:1 fashion with the B-RAF$^{F667E}$ mutant with a $K_D$ of 1.99+/−0.09 μM. Without being bound by theory, this binding constant represents the dimerization constant for KSR2:B-RAF as it nearly matches previously published B-RAF:B-RAF dimerization values (see e.g., Rajakulendran et al, Nature, 2009, 461:542-545). Notably, the addition of a secondary mutation, known to perturb KSR2:B-RAF dimers (B-RAF$^{F667E/R509H}$), completely abrogated any binding signal between KSR2-MEK1 and B-RAF, as shown in FIG. 7E.

Figure 7F:
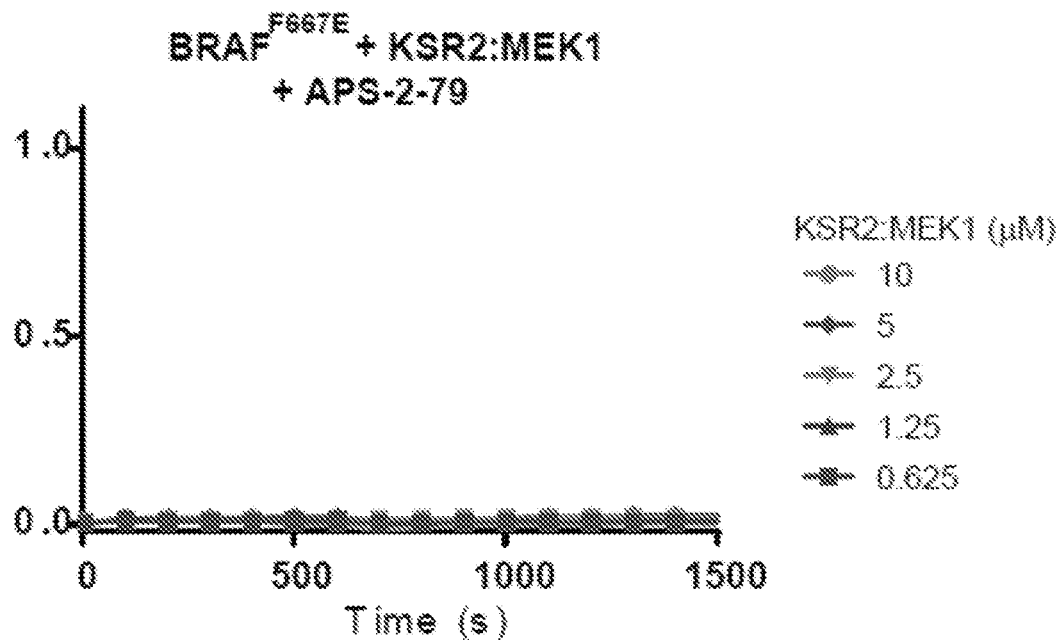
Figure 7G:
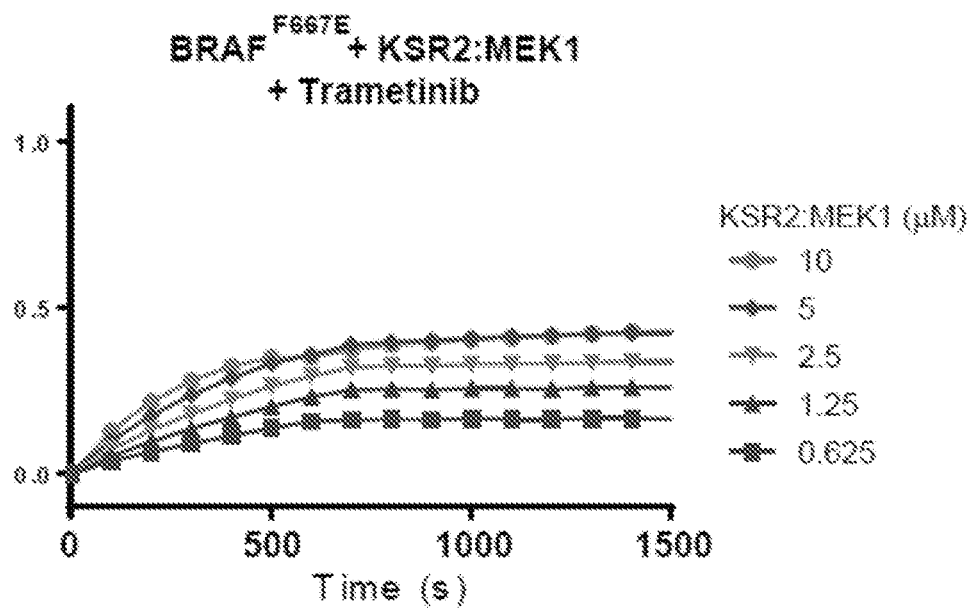

In the presence of Compound 21, the KSR2:B-RAF$^{F667E}$ dimers did not associate, as shown in FIG. 7F, consistent with the prediction of the crystal structure suggesting that Compound 21 may impede RAF-KSR dimers. Furthermore, the MEK inhibitor trametinib did not impede KSR2:B-RAF interactions, but rather reproducibly enhanced dimerization almost 2-fold, as shown in FIG. 7G. Therefore, it was concluded that B-RAF can dimerize with KSR2:MEK1 complexes directly via KSR2, and this interaction is antagonized by Compound 21. Without being bound by theory, it was hypothesized that stabilization of the KSR inactive state (KSRi) via Compound 21 potentiates the effect of MEK inhibitors by limiting feedback in Ras-mutant models, due to KSR's specific function in Ras-mutant, as opposed to RAF-mutant signaling[27] and the ability of Compound 21 to impede RAF-KSR dimers. The synergy of Compound 21 with trametinib was tested in Ras-mutant cell lines, and RAF-mutant cell lines were used as controls.

Example 19. Cell Studies

A. KSR Selectivity

Figure 8:
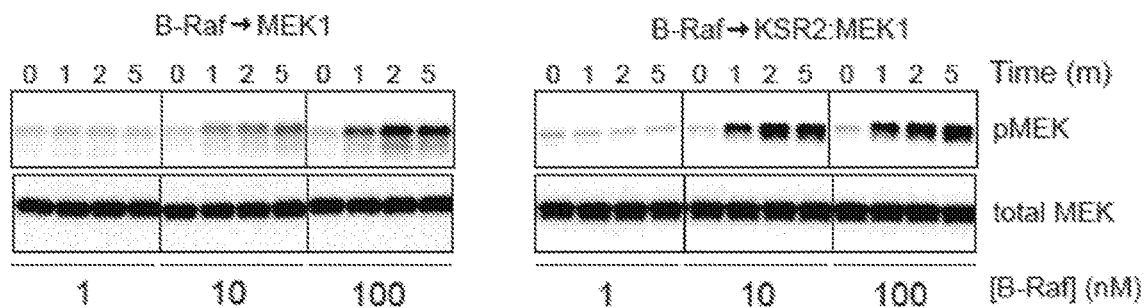
FIG. 8 shows phosphorylation of MEK1 and KSR2:MEK1 with increasing amounts of B-RAF kinase over time. Reactions were initiated by the addition of 100 µM ATP and halted at the indicated times. Each reaction was then immunoblotted and probed for pMEK and tMEK to detect RAF-mediated MEK phosphorylation.
Figure 9A:
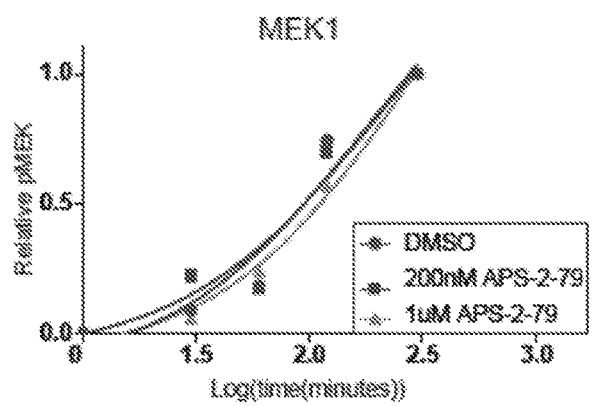
FIGS. 9A-9C show phosphorylation of MEK1, KSR2:MEK1, and KSR2$^{A690F}$:MEK1 by B-RAF over time in the presence of Compound 21. Relative pMEK was determined by quantification of band intensities from western blots using Image Lab Software 4.1.
Figure 9B:
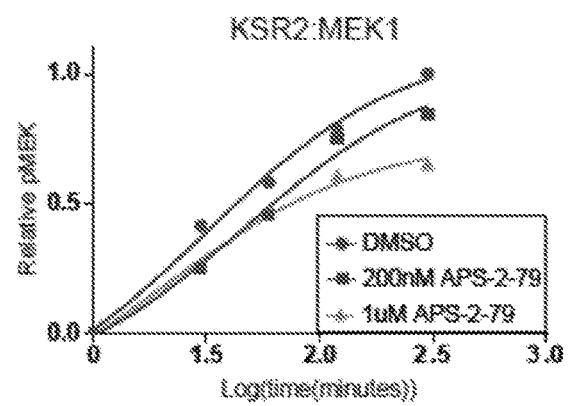
Figure 9C:
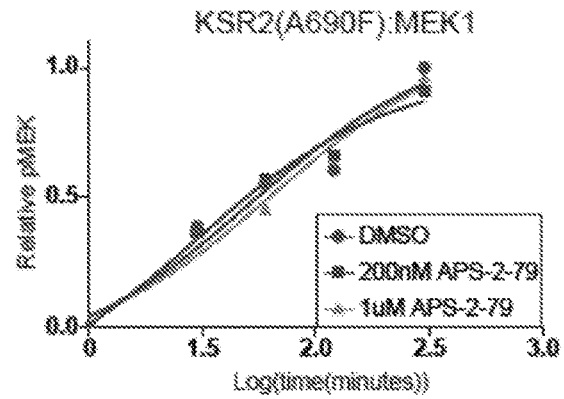
Figure 10A:
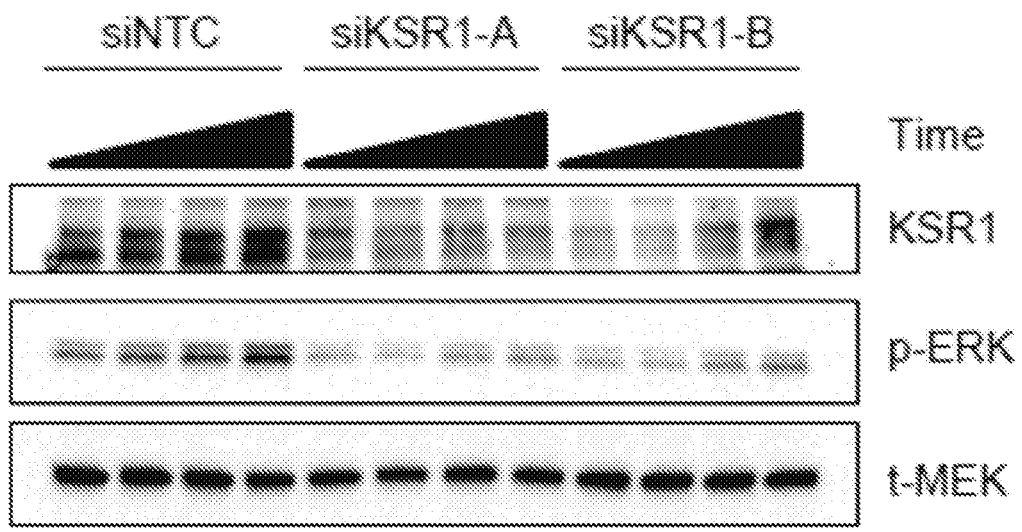
FIGS. 10A-10B show KSR1 knockdown and Compound 21 treatment similarly block FBS-induced ERK activation.
Figure 10B:
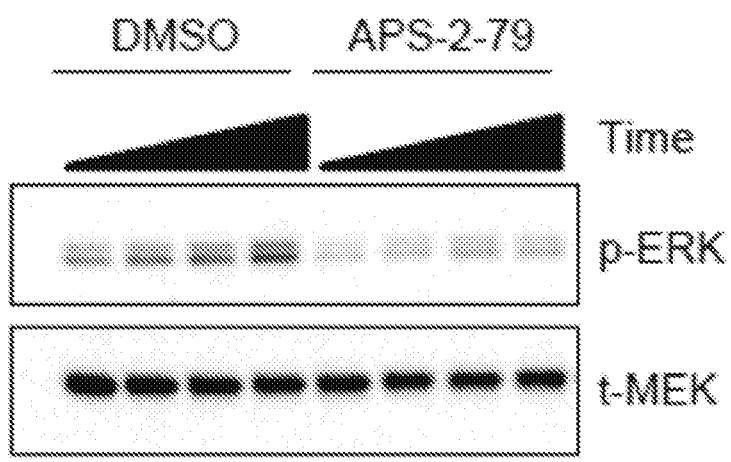

KSR-based selectivity of Compound 21 within the MAPK cascade was further evaluated using in vitro assays. Dose dependent phosphorylation of MEK on Ser218/Ser222 by RAF could be enhanced at least 10-fold in the presence of KSR, as shown in FIG. 8. KSR-stimulated MEK phosphorylation by RAF was significantly reduced by addition of Compound 21, as shown in FIGS. 9A-9C. However, Compound 21 was essentially inactive when KSR was absent or when the KSR2$^{A690F}$ mutant was used for in vitro assays. Furthermore, Compound 21 lacked detectable inhibitory activity against purified forms of RAF, MEK, or ERK. Finally, Compound 21 was found to mimic the effects of RNAi based knockdown of KSR1 in growth-factor stimulated cells, as shown in FIGS. 10A-10B.

B. Combination Treatment with MEK Inhibitor

Figure 11:
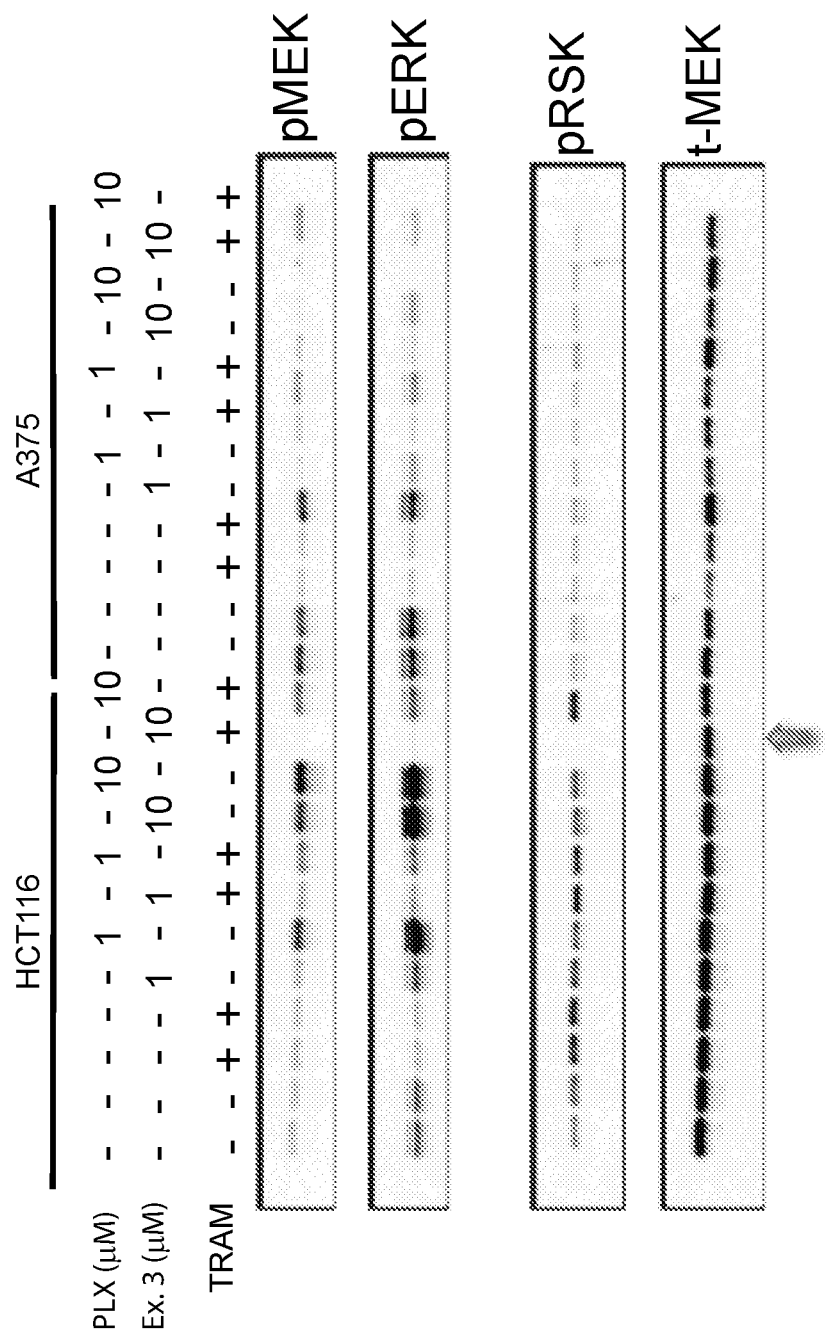
FIG. 11 shows a western blot analysis of the treatment of cells with the Compound 21 in combination with a MEK inhibitor, trametinib. The arrow indicates effective pathway knockdown by combination inhibitors.

Model cell lines A375 (BRAF$^{V600E}$ positive) and HCT-116 (KRas$^{G12D}$ positive) were treated with the Compound 21 in combination with a MEK inhibitor, trametinib. A reduction in MAPK pathway readouts based on phospho-antibodies was observed when trametinib was combined with the Compound 21, as shown in FIG. 11. Trametinib alone, Compound 21, or combinations of trametinib with the RAF inhibitor PLX4720 did not display the same pathway inhibition (pERK, pMEK, and pRSK) as the 6,7-dimethoxy-N-(2-methyl-4-phenoxyphenyl)quinazolin-4-amine 2,2,2-trifluoroacetate+trametinib co-treatment. The same level of pathway inhibition was not observed when trametinib was combined with any of a panel of known kinase inhibitors that have been assessed as non-KSR binders (including staurosporine, sutent, dasatinib, erlotinib, and lapatinib).

Figure 12:
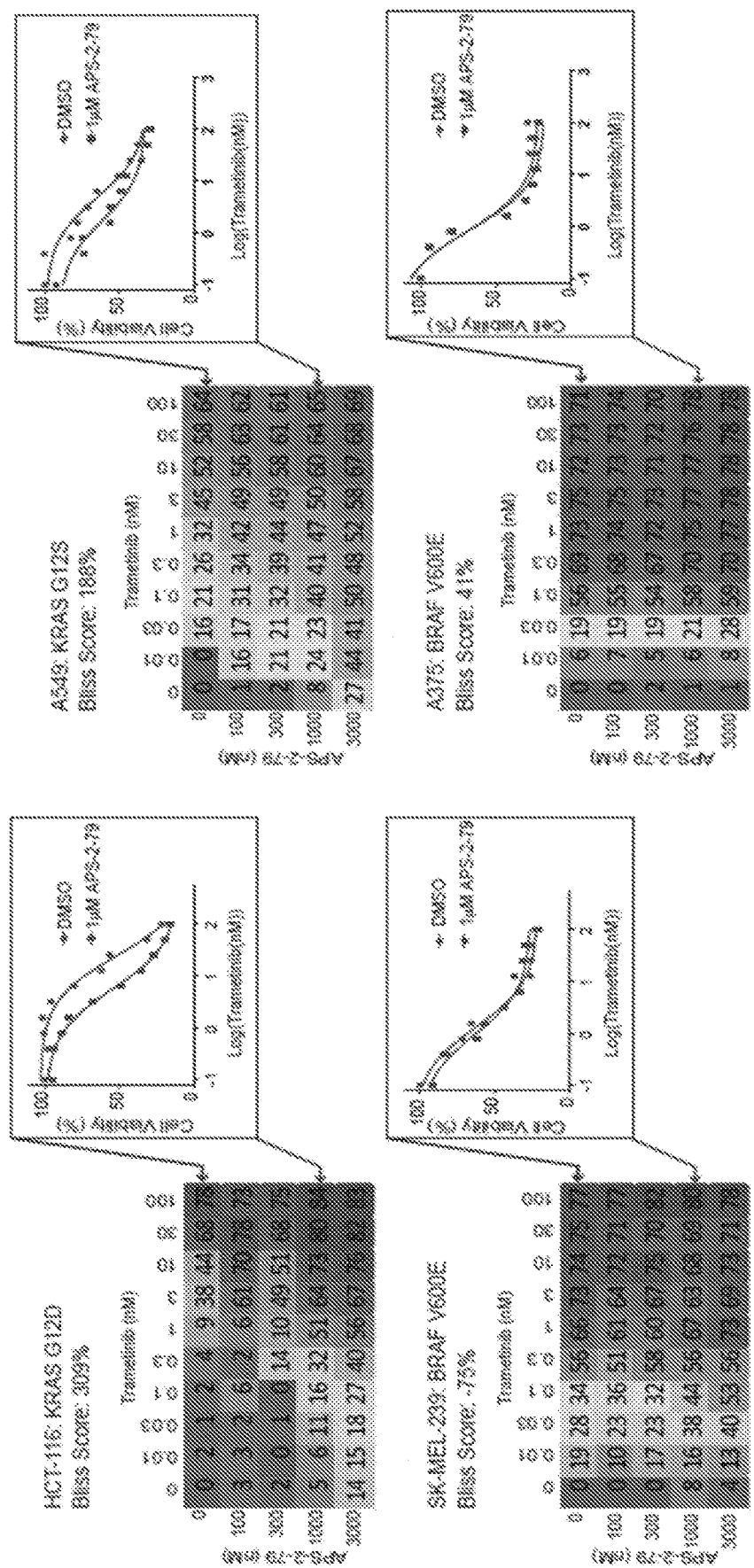
FIG. 12 shows Compound 21 enhancing the efficacy of the clinical MEK inhibitor trametinib within cancer cell lines containing K-Ras mutations. Dose responses of Compound 21 and trametinib (MEKi) on viability of K-Ras mutant (HCT-116, A549) and B-RAF mutant (A375, SK-MEL-239) cell lines. High BLISS scores indicate statistically significant synergy between Compound 21 and trametinib specifically within K-Ras mutant cells. Numbers listed within synergy matrices, representing % growth inhibition relative to DMSO controls, are mean of two replicates. Insets highlight dose responses of trametinib in the absence or presence of 1 µM Compound 21.
Figures 13A, 13B, 13C, 13D:
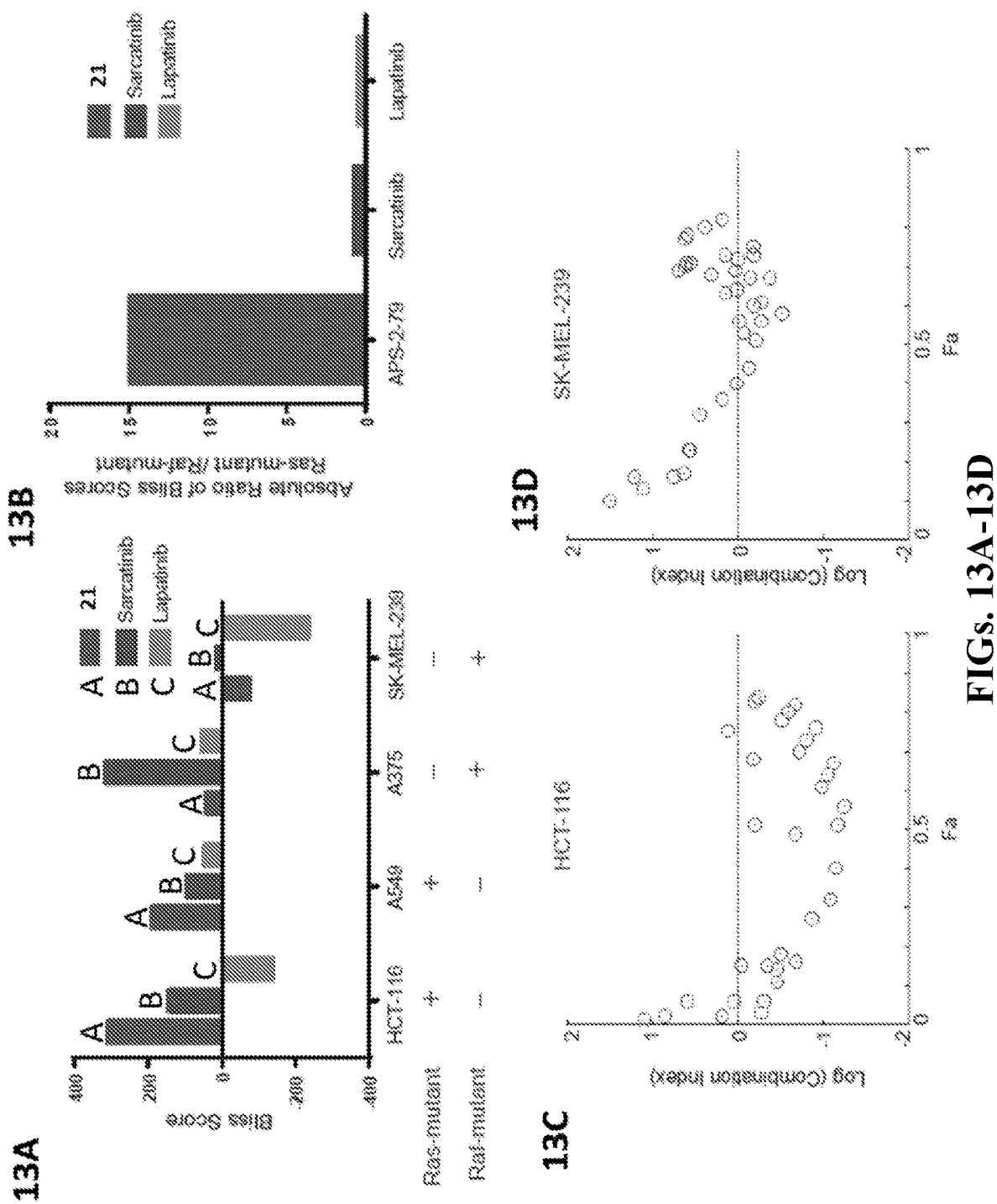
FIGS. 13A-13D show data validating that Compound 21 is synergistic with trametinib in Ras-mutant cells.
Figures 14A, 14B:
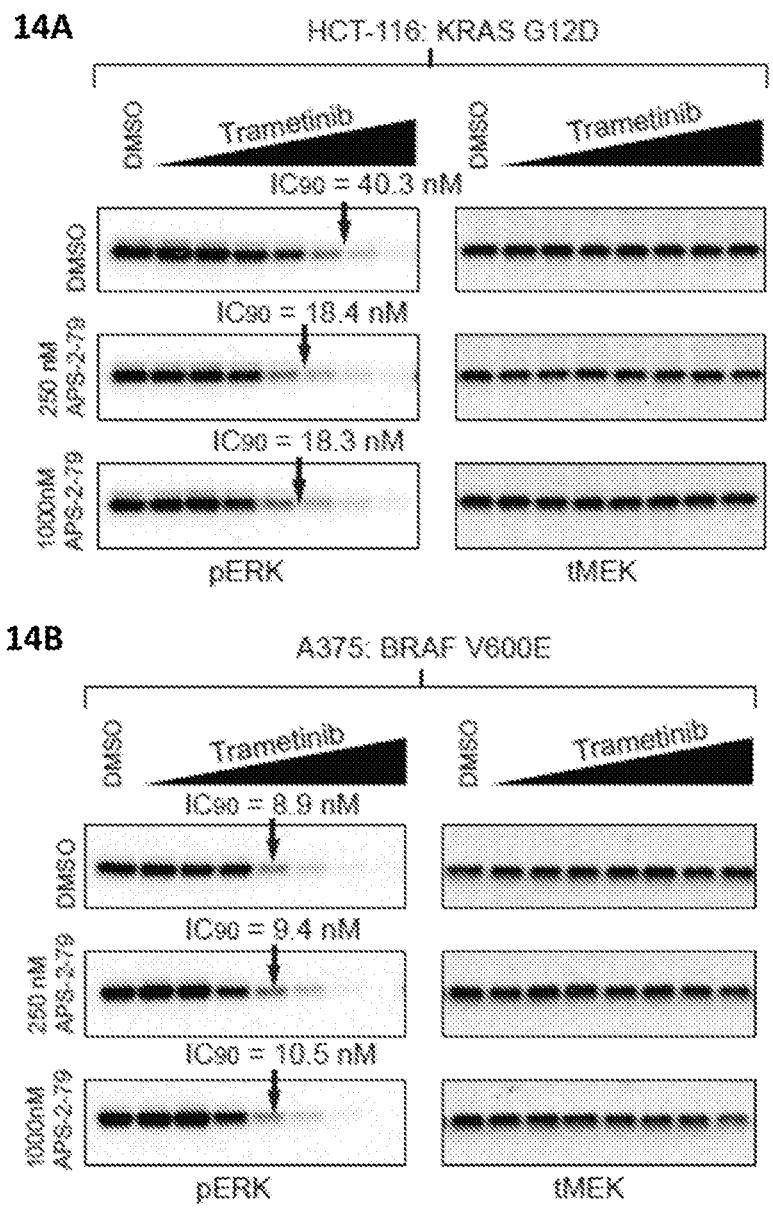
FIGS. 14A-14B shows the increased potency of trametinib in the presence of Compound 21 within HCT-116 cells relative to the control cell line A375, which occurs through enhanced down-regulation of Ras-MAPK signaling (as measured by ERK1/2$^{pT202/pY204}$).

Further, it was found that Compound 21 shifted the cell viability dose response to trametinib in the Ras-mutant cell lines HCT-116 and A549, as shown in FIG. 12. BLISS independence analysis over a full concentration matrix revealed that KSRi significantly increases trametinib potency in K-Ras mutant cell lines, but not B-RAF mutant cell lines SK-MEL-239 and A375. Control compounds that are likely to share similar off-targets with Compound 21, but lack significant KSR-directed activity, did not demonstrate Ras-mutant specific synergy, suggesting that the enhanced activity of trametinib when combined with Compound 21 occurs through modulation of KSR, as shown in FIG. 13. To determine the possible mechanism for Compound 21/trametinib synergy, MAPK signaling was examined and found that Compound 21 treatment caused a 2-fold enhancement in the IC$_{90}$ of trametinib on ERK phosphorylation in the Ras-mutant HCT-116 cell line but not the RAF-mutant SK-MEL-239 cell line, as shown in FIGS. 14A-14B.

C. In Vitro Assays Using Model Cell Lines

Figure 15A:
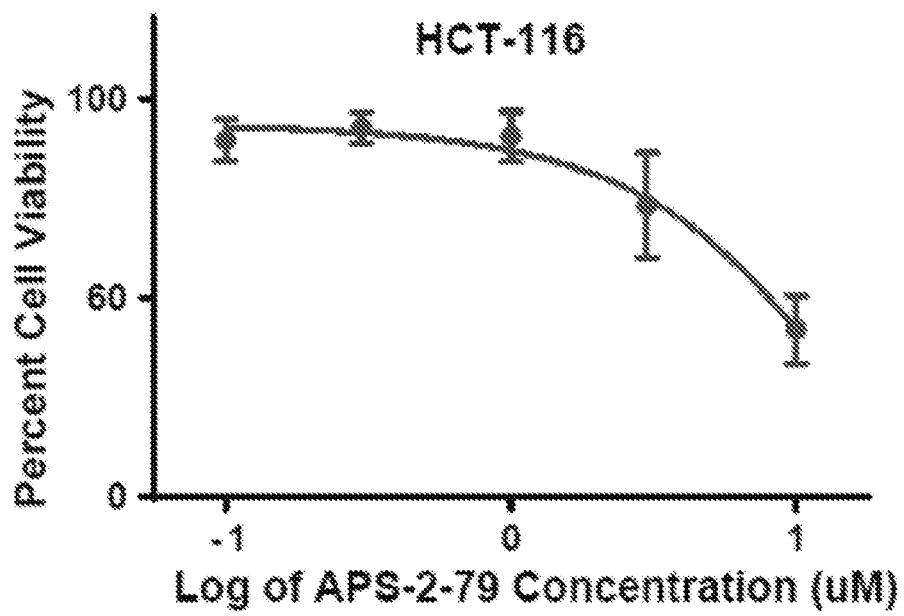
FIGS. 15A-15C show the results of in vitro cell assays using Compound 21 and HTC-116 cells (FIG. 15A), A549 cells (FIG. 15B), and LOVO cells (FIG. 15C).
Figure 15B:
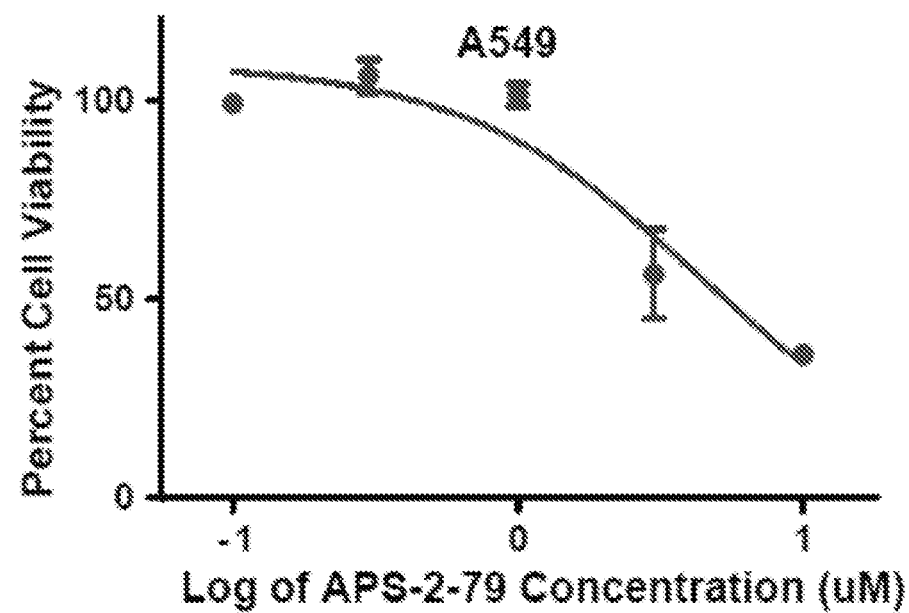
Figure 15C:
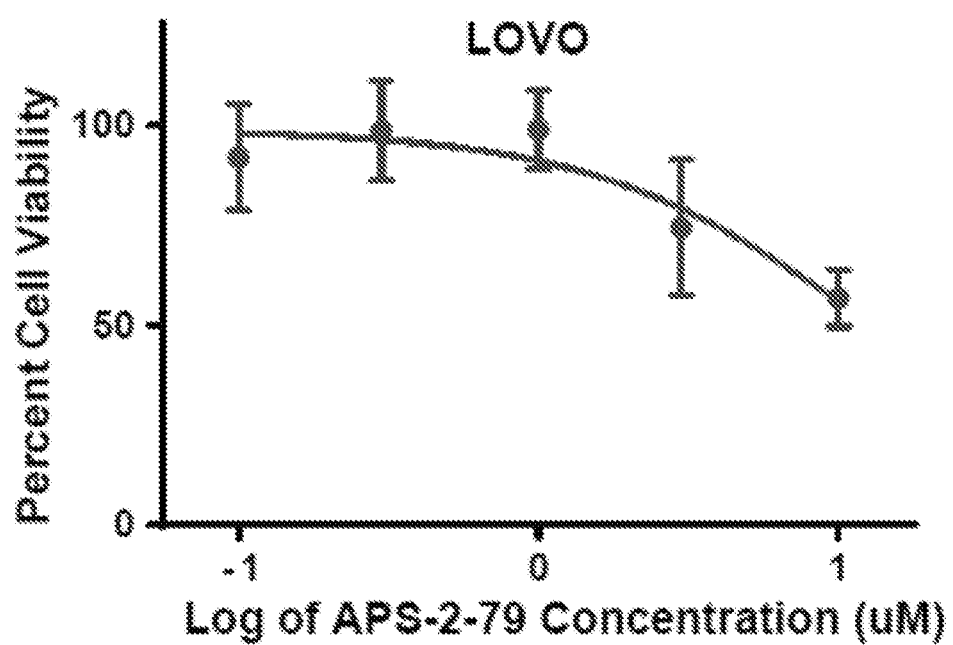

Model cell lines HCT-116, A549, and LOVO were plated at a density of 500 cells per well in a 96 well plate. Cell were then treated with increasing concentrations (0.1 μM, 0.3 μM, 1 μM, 3 μM, 10 μM) of Compound 21 (i.e., APS-2-79) for 72 hours. Cell viability was analyzed using the fluorescent resazurin assay. Resazurin was added to each well to a final concentration of 0.02 mg/mL. After 3 h of incubation at 37° C., cell viability was determined by measuring fluorescence with an excitation 560 nM/590 nM emission filter set. FIGS. 15A-15C show the results of the in vitro cell assays using Compound 21.

Example 20. Synergy Analysis and Scoring

The BLISS independence model was used to evaluate synergism between the indicated inhibitors (see e.g., Zhao et al, *Journal of Biomolecular Screening*, 2014, 19:817-821). BLISS index was calculated by determining the difference between the expected combination value (the product of the viability ratio of drug1 alone and drug2 alone) and the observed combination value (the viability ratio observed from combination treatment with drug1 and drug2). The viability ratio represented the viability observed for treated (inhibitors) relative to controls (DMSO). The sum of these values across each 8×5 concentration matrix is presented in FIG. 12. Combination indexes (see e.g., Chou et al, *Advances in Enzyme Regulation*, 1984, 22:27-55) were separately calculated using the Compusyn Software developed by Combosyn Inc.

Example 21. Biolayer Inferometry Using Octet Red 96

Interactions between purified B-RAF and the KSR2:MEK1 complex were measured using biolayer inferometry on the Octet Red96 system (Forte Bio). Binding experiments were performed at 30° C. in a buffer containing 10 mM phosphate-buffered saline pH 7.2, 1% BSA, and 0.01% Tween. Briefly, B-RAF and B-RAF mutant proteins were biotinylated overnight accordingly to manufacturer instructions (Thermo Fisher) and subsequently purified. For these studies, 300 nM of biotinylated B-Raf was captured on pre-immobilized streptavidin sensor heads. The RAF-immobilized sensor heads were incubated with 5 different concentrations of purified KSR2:MEK1 complex (range: 625 nM to 10 μM in two-fold dilutions). Association and dissociation was monitored over 660 and 840 seconds, respectively. Data sets were normalized and analysed using global fit binding models (Fortebio software). K$_{on}$ and K$_{off}$ were used to derive the K$_D$ values in FIGS. 7A-7G.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I:

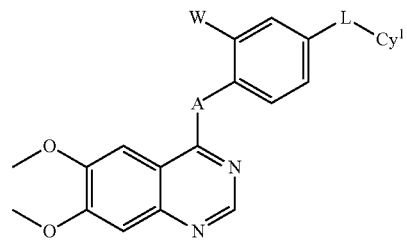

or a pharmaceutically acceptable salt thereof, wherein:

A is selected from the group consisting of NH, N(CH$_3$), S, O, and CH$_2$;

L is selected from the group consisting of O, NH, S, and CH$_2$;

W is independently selected from the group consisting of halo and C$_{1-4}$ alkyl;

Cy¹ is selected from the group consisting of:

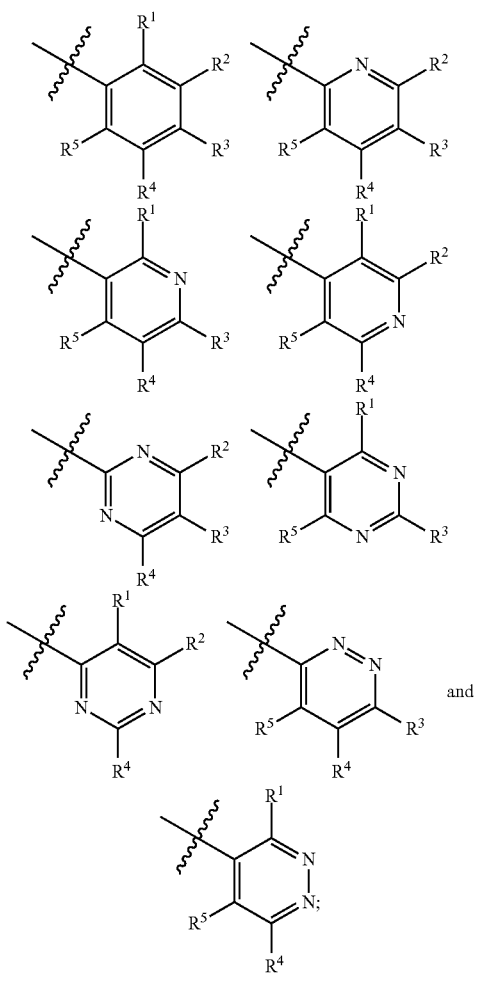

R¹ and R⁵ are each independently selected from the group consisting of H, halo, OH, $C_{1-4}$ alkyl, and $C_{1-4}$ haloalkyl;
R³ is selected from the group consisting of H and halo; and
R² and R⁴ are each independently selected from the group consisting of H and halo.

2. The compound of claim 1, wherein the compound is a compound of Formula Ib:

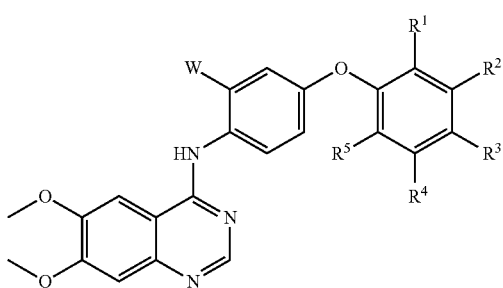

or a pharmaceutically acceptable salt thereof.

3. The compound of claim 1, wherein the compound is selected from the group consisting of:

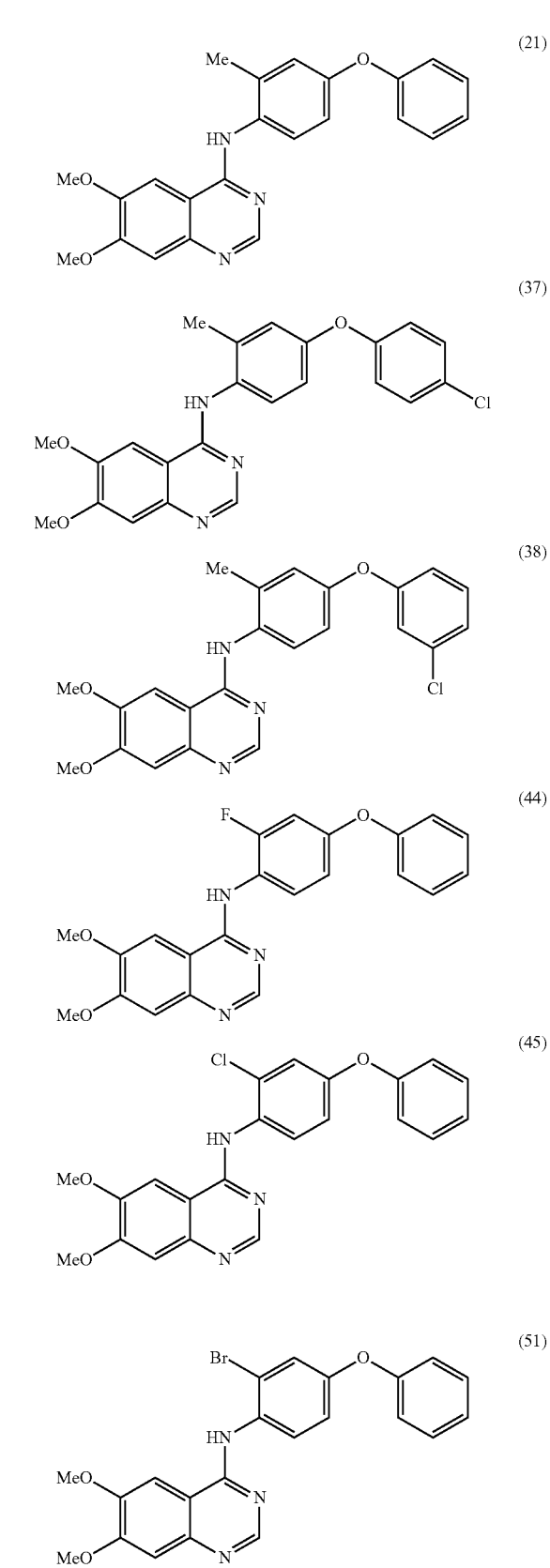

-continued

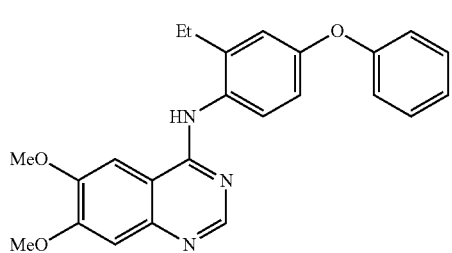
(55)

or a pharmaceutically acceptable salt thereof.

4. The compound of claim 1, wherein the compound is

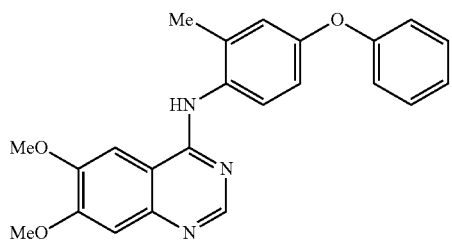 [SMILES: COc1cc2ncnc(Nc3ccc(Oc4ccccc4)cc3F)c2cc1OC]
(21)

or a pharmaceutically acceptable salt thereof.

5. A pharmaceutical composition comprising a compound of claim 1, or a pharmaceutically acceptable salt thereof, and at least one pharmaceutically acceptable carrier.

6. A method of treating a disease associated with KSR in a patient in need thereof, comprising administering to the patient a therapeutically effective amount of a compound of claim 1, or a pharmaceutically acceptable salt thereof, wherein the patient has colon cancer.

7. The method of claim 6, further comprising administering a therapeutically effective amount of an MEK inhibitor to the patient, wherein the MEK inhibitor is selected from the group consisting of trametinib, selumetinib, binimetinib, refametinib, pimasertib, cobimetinib, AZD8330, RO4987655, RO5126766, WX-554, E6201, PD-325901, CI-1040, GDC-0623, G-573, TAK-733, PD318088, PD98059, PD334581, 6-methoxy-7-(3-morpholin-4-yl-propoxy)-4-(4-phenoxy-phenylamino)quinoline-3-carbonitrile, and 4-[3-Chloro-4-(1-methyl-1H-imidazol-2-ylsulfanyl)phenylamino]-6-methoxy-7-(3-morpholin-4-yl-propoxy)-quinoline-3-carbonitrile.

* * * * *